(12) United States Patent
Lambeth et al.

(10) Patent No.: US 7,119,249 B2
(45) Date of Patent: Oct. 10, 2006

US007119249B2

(54) METHODS AND TRANSGENIC MOUSE MODEL FOR IDENTIFYING AND MODULATING FACTORS INVOLVED IN THE PRODUCTION OF REACTIVE OXYGEN INTERMEDIATES

(75) Inventors: J. David Lambeth, Atlanta, GA (US); Guangjie Cheng, Atlanta, GA (US); James McCoy, Atlanta, GA (US)

(73) Assignee: Emory University, Atlanta, GA (US)

( * ) Notice: Subject to any disclaimer, the term of this patent is extended or adjusted under 35 U.S.C. 154(b) by 203 days.

(21) Appl. No.: 10/618,839

(22) Filed: Jul. 14, 2003

(65) Prior Publication Data

US 2004/0093628 A1 May 13, 2004

Related U.S. Application Data

(60) Provisional application No. 60/395,498, filed on Jul. 12, 2002.

(51) Int. Cl.
*A01K 67/027* (2006.01)
*A01K 67/00* (2006.01)
*A01K 67/033* (2006.01)
*G01N 33/00* (2006.01)

(52) U.S. Cl. ................................ 800/18; 800/3; 800/8; 800/9; 435/325

(58) Field of Classification Search ................ 800/3, 800/8, 9, 18; 435/325
See application file for complete search history.

(56) References Cited

PUBLICATIONS

Dupuy et al., "Purification of a novel flavoprotein involved in the thyroid NADPH oxidase," Journal of Biological Chemistry 275(52): 37265–37269, 1999.*

Capecchi MR, "The new mouse genetics: altering the genome by gene targeting," Trends in Genetics 5(3): 70–76, 1989.*
Suh et al., "Cell transformation by the superoxide–generating oxidase Mox1," Nature 401:79–82, 1999.*
Cowan et al, "Targeting gene expression to endothelium in transgenic animals: a comparison of the human ICAM–2, PECAM–1 and endoglin promoters," Xenotransplanation 10:223–231, 2003.*
Hammer et al., "Spontaneous inflammatory disease in transgenic rats expressing HLA–B27 and human B2m: an animal model of HLA–B27–associated human disorders," Cell 63:1099–1112, 1990.□□
Cheng et al., "Homologs of gp91phox: cloning and tissue expression of Nox3, Nox4, Nox5," Gene 269: 131–140, 2001.
Edens et al., "Tyrosine cross–linking of extracellular matrix is catalyzed by Duox, a multidomain oxidase/peroxidase with homology to the phagocyte oxidase subunit gp91phox," Journal of Cell Biology 154(4): 879–891, 2001.
Weber et al., "The activity of highly promiscuous AP–1 element can be confined to neurons by a tissue–selective repressive element," Journal of Neuroscience 18(14): 5264–5274, 1998.

* cited by examiner

*Primary Examiner*—Joseph Woitach
*Assistant Examiner*—Thaian N. Ton
(74) *Attorney, Agent, or Firm*—Klarquist Sparkman LLP

(57) ABSTRACT

The present invention provides a transgenic non-human animal, in particular a transgenic mouse encoding the NOX and Duox family of proteins, which generate reactive oxygen intermediates (ROI). The present invention additionally comprises cells and cell lines containing transgenes encoding for members of the NOX and Duox family of proteins. The present invention further comprises methods and compositions for evaluating regulators of abnormal cell growth and in the development of compounds that effect ROI expression.

11 Claims, 5 Drawing Sheets

(5 of 5 Drawing Sheet(s) Filed in Color)

SEQUENCE LISTING

```
<160> NUMBER OF SEQ ID NOS: 19

<210> SEQ ID NO 1
<211> LENGTH: 2609
<212> TYPE: DNA
<213> ORGANISM: Homo sapiens
<220> FEATURE:
<221> NAME/KEY: CDS
<222> LOCATION: (207)..(1901)
<220> FEATURE:
<221> NAME/KEY: misc_feature
<222> LOCATION: (2025)..(2025)
<223> OTHER INFORMATION: "n" = any nucleotide
<220> FEATURE:
<221> NAME/KEY: misc_feature
<222> LOCATION: (2036)..(2036)
<223> OTHER INFORMATION: "n" = any nucleotide
<220> FEATURE:
<221> NAME/KEY: misc_feature
<222> LOCATION: (2164)..(2164)
<223> OTHER INFORMATION: "n" = any nucleotide
<220> FEATURE:
<221> NAME/KEY: misc_feature
<222> LOCATION: (2264)..(2264)
<223> OTHER INFORMATION: "n" = any nucleotide

<400> SEQUENCE: 1
gctgatagca cagttctgtc cagagaagga aggcggaata aacttattca ttcccaggaa      60
ctcttggggt aggtgtgtgt ttttcacatc ttaaaggctc acagacsctg cgctggacaa     120
atgttccatt cctgaaggac ctctccagaa tccggattgc tgaatcttcc ctgttgccta     180
gaagggctcc aaaccacctc ttgaca atg gga aac tgg gtg gtt aac cac tgg      233
                              Met Gly Asn Trp Val Val Asn His Trp
                              1               5 ttt tca gtt ttg ttt ctg gtt gtt tgg tta ggg ctg aat gtt ttc ctg       281
Phe Ser Val Leu Phe Leu Val Val Trp Leu Gly Leu Asn Val Phe Leu
 10              15                  20                  25 ttt gtg gat gcc ttc ctg aaa tat gag aag gcc gac aaa tac tac tac       329
Phe Val Asp Ala Phe Leu Lys Tyr Glu Lys Ala Asp Lys Tyr Tyr Tyr
                 30                  35                  40 aca aga aaa atc ctt ggg tca aca ttg gcc tgt gcc cga gcg tct gct       377
Thr Arg Lys Ile Leu Gly Ser Thr Leu Ala Cys Ala Arg Ala Ser Ala
             45                  50                  55 ctc tgc ttg aat ttt aac agc acg ctg atc ctg ctt cct gtg tgt cgc       425
Leu Cys Leu Asn Phe Asn Ser Thr Leu Ile Leu Leu Pro Val Cys Arg
         60                  65                  70 aat ctg ctg tcc ttc ctg agg ggc acc tgc tca ttt tgc agc cgc aca       473
Asn Leu Leu Ser Phe Leu Arg Gly Thr Cys Ser Phe Cys Ser Arg Thr
     75                  80                  85 ctg aga aag caa ttg gat cac aac ctc acc ttc cac aag ctg gtg gcc       521
Leu Arg Lys Gln Leu Asp His Asn Leu Thr Phe His Lys Leu Val Ala
 90                  95                 100                 105 tat atg atc tgc cta cat aca gct att cac atc att gca cac ctg ttt       569
Tyr Met Ile Cys Leu His Thr Ala Ile His Ile Ile Ala His Leu Phe
                110                 115                 120 aac ttt gac tgc tat agc aga agc cga cag gcc aca gat ggc tcc ctt       617
Asn Phe Asp Cys Tyr Ser Arg Ser Arg Gln Ala Thr Asp Gly Ser Leu
            125                 130                 135 gcc tcc att ctc tcc agc cta tct cat gat gag aaa aag ggg ggt tct       665
Ala Ser Ile Leu Ser Ser Leu Ser His Asp Glu Lys Lys Gly Gly Ser
        140                 145                 150 tgg cta aat ccc atc cag tcc cga aac acg aca gtg gag tat gtg aca       713
Trp Leu Asn Pro Ile Gln Ser Arg Asn Thr Thr Val Glu Tyr Val Thr
```

-continued

|     |     | 155 |     |     |     |     | 160 |     |     |     |     | 165 |     |     |      |
|-----|-----|-----|-----|-----|-----|-----|-----|-----|-----|-----|-----|-----|-----|-----|------|
| ttc | acc | agc | gtt | gct | ggt | ctc | act | gga | gtg | atc | atg | aca | ata | gcc | ttg  | 761 |
| Phe | Thr | Ser | Val | Ala | Gly | Leu | Thr | Gly | Val | Ile | Met | Thr | Ile | Ala | Leu |
| 170 |     |     |     |     | 175 |     |     |     |     | 180 |     |     |     |     | 185 |

```
ttc acc agc gtt gct ggt ctc act gga gtg atc atg aca ata gcc ttg      761
Phe Thr Ser Val Ala Gly Leu Thr Gly Val Ile Met Thr Ile Ala Leu
170             175                 180                 185 att ctc atg gta act tca gct act gag ttc atc cgg agg agt tat ttt      809
Ile Leu Met Val Thr Ser Ala Thr Glu Phe Ile Arg Arg Ser Tyr Phe
                190                 195                 200 gaa gtc ttc tgg tat act cac cac ctt ttt atc ttc tat atc ctt ggc      857
Glu Val Phe Trp Tyr Thr His His Leu Phe Ile Phe Tyr Ile Leu Gly
            205                 210                 215 tta ggg att cac ggc att ggt gga att gtc cgg ggt caa aca gag gag      905
Leu Gly Ile His Gly Ile Gly Gly Ile Val Arg Gly Gln Thr Glu Glu
        220                 225                 230 agc atg aat gag agt cat cct cgc aag tgt gca gag tct ttt gag atg      953
Ser Met Asn Glu Ser His Pro Arg Lys Cys Ala Glu Ser Phe Glu Met
    235                 240                 245 tgg gat gat cgt gac tcc cac tgt agg cgc cct aag ttt gaa ggg cat     1001
Trp Asp Asp Arg Asp Ser His Cys Arg Arg Pro Lys Phe Glu Gly His
250                 255                 260                 265 ccc cct gag tct tgg aag tgg atc ctt gca ccg gtc att ctt tat atc     1049
Pro Pro Glu Ser Trp Lys Trp Ile Leu Ala Pro Val Ile Leu Tyr Ile
            270                 275                 280 tgt gaa agg atc ctc cgg ttt tac cgc tcc cag cag aag gtt gtg att     1097
Cys Glu Arg Ile Leu Arg Phe Tyr Arg Ser Gln Gln Lys Val Val Ile
        285                 290                 295 acc aag gtt gtt atg cac cca tcc aaa gtt ttg gaa ttg cag atg aac     1145
Thr Lys Val Val Met His Pro Ser Lys Val Leu Glu Leu Gln Met Asn
    300                 305                 310 aag cgt ggc ttc agc atg gaa gtg ggg cag tat atc ttt gtt aat tgc     1193
Lys Arg Gly Phe Ser Met Glu Val Gly Gln Tyr Ile Phe Val Asn Cys
315                 320                 325 ccc tca atc tct ctc ctg gaa tgg cat cct ttt act ttg acc tct gct     1241
Pro Ser Ile Ser Leu Leu Glu Trp His Pro Phe Thr Leu Thr Ser Ala
330                 335                 340                 345 cca gag gaa gat ttc ttc tcc att cat atc cga gca gca ggg gac tgg     1289
Pro Glu Glu Asp Phe Phe Ser Ile His Ile Arg Ala Ala Gly Asp Trp
            350                 355                 360 aca gaa aat ctc ata agg gct ttc gaa caa caa tat tca cca att ccc     1337
Thr Glu Asn Leu Ile Arg Ala Phe Glu Gln Gln Tyr Ser Pro Ile Pro
        365                 370                 375 agg att gaa gtg gat ggt ccc ttt ggc aca gcc agt gag gat gtt ttc     1385
Arg Ile Glu Val Asp Gly Pro Phe Gly Thr Ala Ser Glu Asp Val Phe
    380                 385                 390 cag tat gaa gtg gct gtg ctg gtt gga gca gga att ggg gtc acc ccc     1433
Gln Tyr Glu Val Ala Val Leu Val Gly Ala Gly Ile Gly Val Thr Pro
395                 400                 405 ttt gct tct atc ttg aaa tcc atc tgg tac aaa ttc cag tgt gca gac     1481
Phe Ala Ser Ile Leu Lys Ser Ile Trp Tyr Lys Phe Gln Cys Ala Asp
410                 415                 420                 425 cac aac ctc aaa aca aaa aag atc tat ttc tac tgg atc tgc agg gag     1529
His Asn Leu Lys Thr Lys Lys Ile Tyr Phe Tyr Trp Ile Cys Arg Glu
            430                 435                 440 aca ggt gcc ttt tcc tgg ttc aac aac ctg ttg act tcc ctg gaa cag     1577
Thr Gly Ala Phe Ser Trp Phe Asn Asn Leu Leu Thr Ser Leu Glu Gln
        445                 450                 455 gag atg gag gaa tta ggc aaa gtg ggt ttt cta aac tac cgt ctc ttc     1625
Glu Met Glu Glu Leu Gly Lys Val Gly Phe Leu Asn Tyr Arg Leu Phe
    460                 465                 470 ctc acc gga tgg gac agc aat att gtt ggt cat gca gca tta aac ttt     1673
```

```
                Leu Thr Gly Trp Asp Ser Asn Ile Val Gly His Ala Ala Leu Asn Phe
                    475                 480                 485 gac aag gcc act gac atc gtg aca ggt ctg aaa cag aaa acc tcc ttt           1721
Asp Lys Ala Thr Asp Ile Val Thr Gly Leu Lys Gln Lys Thr Ser Phe
490                 495                 500                 505 ggg aga cca atg tgg gac aat gag ttt tct aca ata gct acc tcc cac           1769
Gly Arg Pro Met Trp Asp Asn Glu Phe Ser Thr Ile Ala Thr Ser His
                510                 515                 520 ccc aag tct gta gtg gga gtt ttc tta tgt ggc cct cgg act ttg gca           1817
Pro Lys Ser Val Val Gly Val Phe Leu Cys Gly Pro Arg Thr Leu Ala
            525                 530                 535 aag agc ctg cgc aaa tgc tgt cac cga tat tcc agt ctg gat cct aga           1865
Lys Ser Leu Arg Lys Cys Cys His Arg Tyr Ser Ser Leu Asp Pro Arg
        540                 545                 550 aag gtt caa ttc tac ttc aac aaa gaa aat ttt tga gttataggaa                1911
Lys Val Gln Phe Tyr Phe Asn Lys Glu Asn Phe
    555                 560 taaggacggt aatctgcatt ttgtctcttt gtatcttcag taattgagtt ataggaataa         1971
ggacggtaat ctgcatttg tctctttgta tcttcagtaa tttacttggt ctcntcaggt          2031
ttgancagtc actttaggat aagaatgtgc ctctcaagcc ttgactccct ggtattcttt         2091
ttttgattgc attcaacttc gttacttgag cttcagcaac ttaagaactt ctgaagttct         2151
taaagttctg aanttcttaa agcccatgga tcctttctca gaaaaataac tgtaaatctt         2211
tctggacagc catgactgta gcaaggcttg atagcagaag tttggtggtt canaattata         2271
caactaatcc caggtgattt tatcaattcc agtgttacca tctcctgagt tttggtttgt         2331
aatcttttgt ccctcccacc cccacagaag attttaagta gggtgacttt ttaaataaaa         2391
atttattgaa taattaatga taaaacataa taataaacat aaataataaa caaaattacc         2451 gagaaccca tccccatata acaccaacag tgtacatgtt tactgtcact tttgatatgg         2511
tttatccagt gtgaacagca atttattatt tttgctcatc aaaaaataaa ggatttttt         2571 tcacttgaaa aaaaaaaaaa aaaaaaaaaa aaaaaaa                                  2609

<210> SEQ ID NO 2
<211> LENGTH: 564
<212> TYPE: PRT
<213> ORGANISM: Homo sapiens

<400> SEQUENCE: 2

Met Gly Asn Trp Val Val Asn His Trp Phe Ser Val Leu Phe Leu Val
1               5                   10                  15

Val Trp Leu Gly Leu Asn Val Phe Leu Phe Val Asp Ala Phe Leu Lys
            20                  25                  30

Tyr Glu Lys Ala Asp Lys Tyr Tyr Thr Arg Lys Ile Leu Gly Ser
        35                  40                  45

Thr Leu Ala Cys Ala Arg Ala Ser Ala Leu Cys Leu Asn Phe Asn Ser
    50                  55                  60

Thr Leu Ile Leu Leu Pro Val Cys Arg Asn Leu Leu Ser Phe Leu Arg
65                  70                  75                  80

Gly Thr Cys Ser Phe Cys Ser Arg Thr Leu Arg Lys Gln Leu Asp His
                85                  90                  95

Asn Leu Thr Phe His Lys Leu Val Ala Tyr Met Ile Cys Leu His Thr
            100                 105                 110

Ala Ile His Ile Ile Ala His Leu Phe Asn Phe Asp Cys Tyr Ser Arg
        115                 120                 125
```

-continued

```
Ser Arg Gln Ala Thr Asp Gly Ser Leu Ala Ser Ile Leu Ser Ser Leu
    130                 135                 140
Ser His Asp Glu Lys Lys Gly Gly Ser Trp Leu Asn Pro Ile Gln Ser
145                 150                 155                 160
Arg Asn Thr Thr Val Glu Tyr Val Thr Phe Thr Ser Val Ala Gly Leu
                165                 170                 175
Thr Gly Val Ile Met Thr Ile Ala Leu Ile Leu Met Val Thr Ser Ala
            180                 185                 190
Thr Glu Phe Ile Arg Arg Ser Tyr Phe Glu Val Phe Trp Tyr Thr His
        195                 200                 205
His Leu Phe Ile Phe Tyr Ile Leu Gly Leu Gly Ile His Gly Ile Gly
    210                 215                 220
Gly Ile Val Arg Gly Gln Thr Glu Glu Ser Met Asn Glu Ser His Pro
225                 230                 235                 240
Arg Lys Cys Ala Glu Ser Phe Glu Met Trp Asp Asp Arg Asp Ser His
                245                 250                 255
Cys Arg Arg Pro Lys Phe Glu Gly His Pro Pro Glu Ser Trp Lys Trp
            260                 265                 270
Ile Leu Ala Pro Val Ile Leu Tyr Ile Cys Glu Arg Ile Leu Arg Phe
        275                 280                 285
Tyr Arg Ser Gln Gln Lys Val Val Ile Thr Lys Val Val Met His Pro
    290                 295                 300
Ser Lys Val Leu Glu Leu Gln Met Asn Lys Arg Gly Phe Ser Met Glu
305                 310                 315                 320
Val Gly Gln Tyr Ile Phe Val Asn Cys Pro Ser Ile Ser Leu Leu Glu
                325                 330                 335
Trp His Pro Phe Thr Leu Thr Ser Ala Pro Glu Glu Asp Phe Phe Ser
            340                 345                 350
Ile His Ile Arg Ala Ala Gly Asp Trp Thr Glu Asn Leu Ile Arg Ala
        355                 360                 365
Phe Glu Gln Gln Tyr Ser Pro Ile Pro Arg Ile Glu Val Asp Gly Pro
    370                 375                 380
Phe Gly Thr Ala Ser Glu Asp Val Phe Gln Tyr Glu Val Ala Val Leu
385                 390                 395                 400
Val Gly Ala Gly Ile Gly Val Thr Pro Phe Ala Ser Ile Leu Lys Ser
                405                 410                 415
Ile Trp Tyr Lys Phe Gln Cys Ala Asp His Asn Leu Lys Thr Lys Lys
            420                 425                 430
Ile Tyr Phe Tyr Trp Ile Cys Arg Glu Thr Gly Ala Phe Ser Trp Phe
        435                 440                 445
Asn Asn Leu Leu Thr Ser Leu Glu Gln Glu Met Glu Glu Leu Gly Lys
    450                 455                 460
Val Gly Phe Leu Asn Tyr Arg Leu Phe Leu Thr Gly Trp Asp Ser Asn
465                 470                 475                 480
Ile Val Gly His Ala Ala Leu Asn Phe Asp Lys Ala Thr Asp Ile Val
                485                 490                 495
Thr Gly Leu Lys Gln Lys Thr Ser Phe Gly Arg Pro Met Trp Asp Asn
            500                 505                 510
Glu Phe Ser Thr Ile Ala Thr Ser His Pro Lys Ser Val Val Gly Val
        515                 520                 525
Phe Leu Cys Gly Pro Arg Thr Leu Ala Lys Ser Leu Arg Lys Cys Cys
    530                 535                 540
His Arg Tyr Ser Ser Leu Asp Pro Arg Lys Val Gln Phe Tyr Phe Asn
```

-continued

```
             545                 550                 555                 560

Lys Glu Asn Phe

<210> SEQ ID NO 3
<211> LENGTH: 2044
<212> TYPE: DNA
<213> ORGANISM: Homo sapiens
<220> FEATURE:
<221> NAME/KEY: CDS
<222> LOCATION: (104)..(1810)

<400> SEQUENCE: 3
caaagacaaa ataatttact agggaagccc ttactaacga cccaacatcc agacacaggt         60
gagggagaag aaatttcctg acagccgaag agcaacaagt atc atg atg ggg tgc         115
                                             Met Met Gly Cys
                                               1 tgg att ttg aat gag ggt ctc tcc acc ata tta gta ctc tca tgg ctg         163
Trp Ile Leu Asn Glu Gly Leu Ser Thr Ile Leu Val Leu Ser Trp Leu
  5                  10                  15                  20 gga ata aat ttt tat ctg ttt att gac acg ttc tac tgg tat gaa gag         211
Gly Ile Asn Phe Tyr Leu Phe Ile Asp Thr Phe Tyr Trp Tyr Glu Glu
                 25                  30                  35 gag gag tct ttc cat tac aca cga gtt att ttg ggt tca aca ctg gct         259
Glu Glu Ser Phe His Tyr Thr Arg Val Ile Leu Gly Ser Thr Leu Ala
             40                  45                  50 tgg gca cga gca tcc gca ctg tgc ctg aat ttt aac tgc atg cta att         307
Trp Ala Arg Ala Ser Ala Leu Cys Leu Asn Phe Asn Cys Met Leu Ile
         55                  60                  65 cta ata cct gtc agt cga aac ctt att tca ttc ata aga gga aca agt         355
Leu Ile Pro Val Ser Arg Asn Leu Ile Ser Phe Ile Arg Gly Thr Ser
     70                  75                  80 att tgc tgc aga gga ccg tgg agg agg caa tta gac aaa aac ctc aga         403
Ile Cys Cys Arg Gly Pro Trp Arg Arg Gln Leu Asp Lys Asn Leu Arg
 85                  90                  95                 100 ttt cac aaa ctg gtc gcc tat ggg ata gct gtt aat gca acc atc cac         451
Phe His Lys Leu Val Ala Tyr Gly Ile Ala Val Asn Ala Thr Ile His
                105                 110                 115 atc gtg gcg cat ttc ttc aac ctg gaa cgc tac cac tgg agc cag tcc         499
Ile Val Ala His Phe Phe Asn Leu Glu Arg Tyr His Trp Ser Gln Ser
            120                 125                 130 gag gag gcc cag gga ctt ctg gcc gca ctt tcc aag ctg ggc aac acc         547
Glu Glu Ala Gln Gly Leu Leu Ala Ala Leu Ser Lys Leu Gly Asn Thr
        135                 140                 145 cct aac gag agc tac ctc aac cct gtc cgg acc ttc ccc aca aac aca         595
Pro Asn Glu Ser Tyr Leu Asn Pro Val Arg Thr Phe Pro Thr Asn Thr
    150                 155                 160 acc act gaa ttg cta agg aca ata gca ggc gtc acc ggt ctg gtg atc         643
Thr Thr Glu Leu Leu Arg Thr Ile Ala Gly Val Thr Gly Leu Val Ile
165                 170                 175                 180 tct ctg gct tta gtc ttg atc atg acc tcg tca act gag ttc atc aga         691
Ser Leu Ala Leu Val Leu Ile Met Thr Ser Ser Thr Glu Phe Ile Arg
                185                 190                 195 cag gcc tcc tat gag ttg ttc tgg tac aca cac cat gtt ttc atc gtc         739
Gln Ala Ser Tyr Glu Leu Phe Trp Tyr Thr His His Val Phe Ile Val
            200                 205                 210 ttc ttt ctc agc ctg gcc atc cat ggg acg ggt cgg att gtt cga ggc         787
Phe Phe Leu Ser Leu Ala Ile His Gly Thr Gly Arg Ile Val Arg Gly
        215                 220                 225 caa acc caa gac agt ctc tct ctg cac aac atc acc ttc tgt aga gac         835
Gln Thr Gln Asp Ser Leu Ser Leu His Asn Ile Thr Phe Cys Arg Asp
```

```
                        230                 235                 240
cgc tat gca gaa tgg cag aca gtg gcc caa tgc ccc gtg cct caa ttt      883
Arg Tyr Ala Glu Trp Gln Thr Val Ala Gln Cys Pro Val Pro Gln Phe
245                 250                 255                 260 tct ggc aag gaa ccc tcg gct tgg aaa tgg att tta ggc cct gtg gtc      931
Ser Gly Lys Glu Pro Ser Ala Trp Lys Trp Ile Leu Gly Pro Val Val
                265                 270                 275 ttg tat gca tgt gaa aga ata att agg ttc tgg cga ttt caa caa gaa      979
Leu Tyr Ala Cys Glu Arg Ile Ile Arg Phe Trp Arg Phe Gln Gln Glu
            280                 285                 290 gtt gtc att acc aag gtg gta agc cac ccc tct gga gtc ctg gaa ctt     1027
Val Val Ile Thr Lys Val Val Ser His Pro Ser Gly Val Leu Glu Leu
        295                 300                 305 cac atg aaa aag cgt ggc ttt aaa atg gcg cca ggg cag tac atc ttg     1075
His Met Lys Lys Arg Gly Phe Lys Met Ala Pro Gly Gln Tyr Ile Leu
    310                 315                 320 gtg cag tgc cca gcc ata tct tcg ctg gag tgg cac ccc ttc acc ctt     1123
Val Gln Cys Pro Ala Ile Ser Ser Leu Glu Trp His Pro Phe Thr Leu
325                 330                 335                 340 acc tct gcc ccc cag gaa gac ttt ttc agc gtg cac atc cgg gca gca     1171
Thr Ser Ala Pro Gln Glu Asp Phe Phe Ser Val His Ile Arg Ala Ala
                345                 350                 355 gga gac tgg aca gca gcg cta ctg gag gcc ttt ggg gca gag gga cag     1219
Gly Asp Trp Thr Ala Ala Leu Leu Glu Ala Phe Gly Ala Glu Gly Gln
            360                 365                 370 gcc ctc cag gag ccc tgg agc ctg cca agg ctg gca gtg gac ggg ccc     1267
Ala Leu Gln Glu Pro Trp Ser Leu Pro Arg Leu Ala Val Asp Gly Pro
        375                 380                 385 ttt gga act gcc ctg aca gat gta ttt cac tac cca gtg tgt gtg tgc     1315
Phe Gly Thr Ala Leu Thr Asp Val Phe His Tyr Pro Val Cys Val Cys
    390                 395                 400 gtt gcc gcg ggg atc gga gtc act ccc ttc gct gct ctt ctg aaa tct     1363
Val Ala Ala Gly Ile Gly Val Thr Pro Phe Ala Ala Leu Leu Lys Ser
405                 410                 415                 420 ata tgg tac aaa tgc agt gag gca cag acc cca ctg aag ctg agc aag     1411
Ile Trp Tyr Lys Cys Ser Glu Ala Gln Thr Pro Leu Lys Leu Ser Lys
                425                 430                 435 gtg tat ttc tac tgg att tgc cgg gat gca aga gct ttt gag tgg ttt     1459
Val Tyr Phe Tyr Trp Ile Cys Arg Asp Ala Arg Ala Phe Glu Trp Phe
            440                 445                 450 gct gat ctc tta ctc tcc ctg gaa aca cgg atg agt gag cag ggg aaa     1507
Ala Asp Leu Leu Leu Ser Leu Glu Thr Arg Met Ser Glu Gln Gly Lys
        455                 460                 465 act cac ttt ctg agt tat cat ata ttt ctt acc ggc tgg gat gaa aat     1555
Thr His Phe Leu Ser Tyr His Ile Phe Leu Thr Gly Trp Asp Glu Asn
    470                 475                 480 cag gct ctt cac ata gct tta cac tgg gac gaa aat act gac gtg att     1603
Gln Ala Leu His Ile Ala Leu His Trp Asp Glu Asn Thr Asp Val Ile
485                 490                 495                 500 aca ggc tta aag cag aag acc ttc tat ggg agg ccc aac tgg aac aat     1651
Thr Gly Leu Lys Gln Lys Thr Phe Tyr Gly Arg Pro Asn Trp Asn Asn
                505                 510                 515 gag ttc aag cag att gcc tac aat cac ccc agc agc agt att ggc gtg     1699
Glu Phe Lys Gln Ile Ala Tyr Asn His Pro Ser Ser Ser Ile Gly Val
            520                 525                 530 ttc ttc tgt gga cct aaa gct ctc tcg agg aca ctt caa aag atg tgc     1747
Phe Phe Cys Gly Pro Lys Ala Leu Ser Arg Thr Leu Gln Lys Met Cys
        535                 540                 545 cac ttg tat tca tca gct gac ccc aga ggt gtt cat ttc tat tac aac     1795
```

-continued

His Leu Tyr Ser Ser Ala Asp Pro Arg Gly Val His Phe Tyr Tyr Asn
        550                 555                 560 aag gag agc ttc tag actttggagg tcaagtccag gcattgtgtt ttcaatcaag      1850
Lys Glu Ser Phe
565 ttattgattc caaagaactc caccaggaat tcctgtgacg gcctgttgat atgagctccc    1910 agttgggaac tggtgaataa taattaacta ttgtgaacag tacactatac catacttcct    1970 tagcttataa ataacatgtc atatacaaca gaacaaaaac atttactgaa attaaaatat    2030 attatgtttc tcca                                                      2044

<210> SEQ ID NO 4
<211> LENGTH: 568
<212> TYPE: PRT
<213> ORGANISM: Homo sapiens

<400> SEQUENCE: 4

Met Met Gly Cys Trp Ile Leu Asn Glu Gly Leu Ser Thr Ile Leu Val
1               5                   10                  15

Leu Ser Trp Leu Gly Ile Asn Phe Tyr Leu Phe Ile Asp Thr Phe Tyr
            20                  25                  30

Trp Tyr Glu Glu Glu Ser Phe His Tyr Thr Arg Val Ile Leu Gly
        35                  40                  45

Ser Thr Leu Ala Trp Ala Arg Ala Ser Ala Leu Cys Leu Asn Phe Asn
    50                  55                  60

Cys Met Leu Ile Leu Ile Pro Val Ser Arg Asn Leu Ile Ser Phe Ile
65                  70                  75                  80

Arg Gly Thr Ser Ile Cys Cys Arg Gly Pro Trp Arg Arg Gln Leu Asp
                85                  90                  95

Lys Asn Leu Arg Phe His Lys Leu Val Ala Tyr Gly Ile Ala Val Asn
            100                 105                 110

Ala Thr Ile His Ile Val Ala His Phe Phe Asn Leu Glu Arg Tyr His
        115                 120                 125

Trp Ser Gln Ser Glu Glu Ala Gln Gly Leu Leu Ala Ala Leu Ser Lys
    130                 135                 140

Leu Gly Asn Thr Pro Asn Glu Ser Tyr Leu Asn Pro Val Arg Thr Phe
145                 150                 155                 160

Pro Thr Asn Thr Thr Glu Leu Leu Arg Thr Ile Ala Gly Val Thr
                165                 170                 175

Gly Leu Val Ile Ser Leu Ala Leu Val Leu Ile Met Thr Ser Ser Thr
            180                 185                 190

Glu Phe Ile Arg Gln Ala Ser Tyr Glu Leu Phe Trp Tyr Thr His His
        195                 200                 205

Val Phe Ile Val Phe Phe Leu Ser Leu Ala Ile His Gly Thr Gly Arg
    210                 215                 220

Ile Val Arg Gly Gln Thr Gln Asp Ser Leu Ser Leu His Asn Ile Thr
225                 230                 235                 240

Phe Cys Arg Asp Arg Tyr Ala Glu Trp Gln Thr Val Ala Gln Cys Pro
                245                 250                 255

Val Pro Gln Phe Ser Gly Lys Glu Pro Ser Ala Trp Lys Trp Ile Leu
            260                 265                 270

Gly Pro Val Val Leu Tyr Ala Cys Glu Arg Ile Ile Arg Phe Trp Arg
        275                 280                 285

Phe Gln Gln Glu Val Val Ile Thr Lys Val Val Ser His Pro Ser Gly
    290                 295                 300

```
Val Leu Glu Leu His Met Lys Lys Arg Gly Phe Lys Met Ala Pro Gly
305                 310                 315                 320

Gln Tyr Ile Leu Val Gln Cys Pro Ala Ile Ser Ser Leu Glu Trp His
                325                 330                 335

Pro Phe Thr Leu Thr Ser Ala Pro Gln Glu Asp Phe Phe Ser Val His
            340                 345                 350

Ile Arg Ala Ala Gly Asp Trp Thr Ala Ala Leu Leu Glu Ala Phe Gly
        355                 360                 365

Ala Glu Gly Gln Ala Leu Gln Glu Pro Trp Ser Leu Pro Arg Leu Ala
370                 375                 380

Val Asp Gly Pro Phe Gly Thr Ala Leu Thr Asp Val Phe His Tyr Pro
385                 390                 395                 400

Val Cys Val Cys Val Ala Ala Gly Ile Gly Val Thr Pro Phe Ala Ala
                405                 410                 415

Leu Leu Lys Ser Ile Trp Tyr Lys Cys Ser Glu Ala Gln Thr Pro Leu
            420                 425                 430

Lys Leu Ser Lys Val Tyr Phe Tyr Trp Ile Cys Arg Asp Ala Arg Ala
        435                 440                 445

Phe Glu Trp Phe Ala Asp Leu Leu Ser Leu Glu Thr Arg Met Ser
450                 455                 460

Glu Gln Gly Lys Thr His Phe Leu Ser Tyr His Ile Phe Leu Thr Gly
465                 470                 475                 480

Trp Asp Glu Asn Gln Ala Leu His Ile Ala Leu His Trp Asp Glu Asn
                485                 490                 495

Thr Asp Val Ile Thr Gly Leu Lys Gln Lys Thr Phe Tyr Gly Arg Pro
            500                 505                 510

Asn Trp Asn Asn Glu Phe Lys Gln Ile Ala Tyr Asn His Pro Ser Ser
        515                 520                 525

Ser Ile Gly Val Phe Phe Cys Gly Pro Lys Ala Leu Ser Arg Thr Leu
    530                 535                 540

Gln Lys Met Cys His Leu Tyr Ser Ser Ala Asp Pro Arg Gly Val His
545                 550                 555                 560

Phe Tyr Tyr Asn Lys Glu Ser Phe
                565

<210> SEQ ID NO 5
<211> LENGTH: 2044
<212> TYPE: DNA
<213> ORGANISM: Homo sapiens
<220> FEATURE:
<221> NAME/KEY: CDS
<222> LOCATION: (104)..(1810)

<400> SEQUENCE: 5
caaagacaaa ataatttact agggaagccc ttactaacga cccaacatcc agacacaggt      60
gagggagaag aaatttcctg acagccgaag agcaacaagt atc atg atg ggg tgc     115
                                             Met Met Gly Cys
                                               1 tgg att ttg aat gag ggt ctc tcc acc ata tta gta ctc tca tgg ctg     163
Trp Ile Leu Asn Glu Gly Leu Ser Thr Ile Leu Val Leu Ser Trp Leu
  5              10                  15                  20 gga ata aat ttt tat ctg ttt att gac acg ttc tac tgg tat gaa gag     211
Gly Ile Asn Phe Tyr Leu Phe Ile Asp Thr Phe Tyr Trp Tyr Glu Glu
             25                  30                  35 gag gag tct ttc cat tac aca cga gtt att ttg ggt tca aca ctg gct     259
Glu Glu Ser Phe His Tyr Thr Arg Val Ile Leu Gly Ser Thr Leu Ala
```

-continued

```
           40                  45                  50
tgg gca cga gca tcc gca ctg tgc ctg aat ttt aac tgc atg cta att       307
Trp Ala Arg Ala Ser Ala Leu Cys Leu Asn Phe Asn Cys Met Leu Ile
         55                  60                  65 cta ata cct gtc agt cga aac ctt att tca ttc ata aga gga aca agt       355
Leu Ile Pro Val Ser Arg Asn Leu Ile Ser Phe Ile Arg Gly Thr Ser
 70                  75                  80 att tgc tgc aga gga ccg tgg agg agg caa tta gac aaa aac ctc aga       403
Ile Cys Cys Arg Gly Pro Trp Arg Arg Gln Leu Asp Lys Asn Leu Arg
 85                  90                  95                 100 ttt cac aaa ctg gtc gcc tat ggg ata gct gtt aat gca acc atc cac       451
Phe His Lys Leu Val Ala Tyr Gly Ile Ala Val Asn Ala Thr Ile His
                105                 110                 115 atc gtg gcg cat ttc ttc aac ctg gaa cgc tac cac tgg agc cag tcc       499
Ile Val Ala His Phe Phe Asn Leu Glu Arg Tyr His Trp Ser Gln Ser
                120                 125                 130 gag gag gcc cag gga ctt ctg gcc gca ctt tcc aag ctg ggc aac acc       547
Glu Glu Ala Gln Gly Leu Leu Ala Ala Leu Ser Lys Leu Gly Asn Thr
                135                 140                 145 cct aac gag agc tac ctc aac cct gtc cgg acc ttc ccc aca aac aca       595
Pro Asn Glu Ser Tyr Leu Asn Pro Val Arg Thr Phe Pro Thr Asn Thr
    150                 155                 160 acc act gaa ttg cta agg aca ata gca ggc gtc acc ggt ctg gtg atc       643
Thr Thr Glu Leu Leu Arg Thr Ile Ala Gly Val Thr Gly Leu Val Ile
165                 170                 175                 180 tct ctg gct tta gtc ttg atc atg acc tcg tca act gag ttc atc aga       691
Ser Leu Ala Leu Val Leu Ile Met Thr Ser Ser Thr Glu Phe Ile Arg
                185                 190                 195 cag gcc tcc tat gag ttg ttc tgg tac aca cac cat gtt ttc atc gtc       739
Gln Ala Ser Tyr Glu Leu Phe Trp Tyr Thr His His Val Phe Ile Val
        200                 205                 210 ttc ttt ctc agc ctg gcc atc cat ggg acg ggt cgg att gtt cga ggc       787
Phe Phe Leu Ser Leu Ala Ile His Gly Thr Gly Arg Ile Val Arg Gly
            215                 220                 225 caa acc caa gac agt ctc tct ctg cac aac atc acc ttc tgt aga gac       835
Gln Thr Gln Asp Ser Leu Ser Leu His Asn Ile Thr Phe Cys Arg Asp
        230                 235                 240 cgc tat gca gaa tgg cag aca gtg gcc caa tgc ccc gtg cct caa ttt       883
Arg Tyr Ala Glu Trp Gln Thr Val Ala Gln Cys Pro Val Pro Gln Phe
245                 250                 255                 260 tct ggc aag gaa ccc tcg gct tgg aaa tgg att tta ggc cct gtg gtc       931
Ser Gly Lys Glu Pro Ser Ala Trp Lys Trp Ile Leu Gly Pro Val Val
                265                 270                 275 ttg tat gca tgt gaa aga ata att agg ttc tgg cga ttt caa caa gaa       979
Leu Tyr Ala Cys Glu Arg Ile Ile Arg Phe Trp Arg Phe Gln Gln Glu
            280                 285                 290 gtt gtc att acc aag gtg gta agc cac ccc tct gga gtc ctg gaa ctt      1027
Val Val Ile Thr Lys Val Val Ser His Pro Ser Gly Val Leu Glu Leu
            295                 300                 305 cac atg aaa aag cgt ggc ttt aaa atg gcg cca ggg cag tac atc ttg      1075
His Met Lys Lys Arg Gly Phe Lys Met Ala Pro Gly Gln Tyr Ile Leu
    310                 315                 320 gtg cag tgc cca gcc ata tct tcg ctg gag tgg cac ccc ttc acc ctt      1123
Val Gln Cys Pro Ala Ile Ser Ser Leu Glu Trp His Pro Phe Thr Leu
325                 330                 335                 340 acc tct gcc ccc cag gaa gac ttt ttc agc gtg cac atc cgg gca gca      1171
Thr Ser Ala Pro Gln Glu Asp Phe Phe Ser Val His Ile Arg Ala Ala
                345                 350                 355 gga gac tgg aca gca gcg cta ctg gag gcc ttt ggg gca gag gga cag      1219
```

```
                    Gly Asp Trp Thr Ala Ala Leu Leu Glu Ala Phe Gly Ala Glu Gly Gln
                                    360                 365                 370 gcc ctc cag gag ccc tgg agc ctg cca agg ctg gca gtg gac ggg ccc         1267
Ala Leu Gln Glu Pro Trp Ser Leu Pro Arg Leu Ala Val Asp Gly Pro
            375                 380                 385 ttt gga act gcc ctg aca gat gta ttt cac tac cca gtg tgt gtg tgc         1315
Phe Gly Thr Ala Leu Thr Asp Val Phe His Tyr Pro Val Cys Val Cys
        390                 395                 400 gtt gcc gcg ggg atc gga gtc act ccc ttc gct gct ctt ctg aaa tct         1363
Val Ala Ala Gly Ile Gly Val Thr Pro Phe Ala Ala Leu Leu Lys Ser
405                 410                 415                 420 ata tgg tac aaa tgc agt gag gca cag acc cca ctg aag ctg agc aag         1411
Ile Trp Tyr Lys Cys Ser Glu Ala Gln Thr Pro Leu Lys Leu Ser Lys
                425                 430                 435 gtg tat ttc tac tgg att tgc cgg gat gca aga gct ttt gag tgg ttt         1459
Val Tyr Phe Tyr Trp Ile Cys Arg Asp Ala Arg Ala Phe Glu Trp Phe
            440                 445                 450 gct gat ctc tta ctc tcc ctg gaa aca cgg atg agt gag cag ggg aaa         1507
Ala Asp Leu Leu Leu Ser Leu Glu Thr Arg Met Ser Glu Gln Gly Lys
        455                 460                 465 act cac ttt ctg agt tat cat ata ttt ctt acc ggc tgg gat gaa aat         1555
Thr His Phe Leu Ser Tyr His Ile Phe Leu Thr Gly Trp Asp Glu Asn
    470                 475                 480 cag gct ctt cac ata gct tta cac tgg gac gaa aat act gac gtg att         1603
Gln Ala Leu His Ile Ala Leu His Trp Asp Glu Asn Thr Asp Val Ile
485                 490                 495                 500 aca ggc tta aag cag aag acc ttc tat ggg agg ccc aac tgg aac aat         1651
Thr Gly Leu Lys Gln Lys Thr Phe Tyr Gly Arg Pro Asn Trp Asn Asn
                505                 510                 515 gag ttc aag cag att gcc tac aat cac ccc agc agc agt att ggc gtg         1699
Glu Phe Lys Gln Ile Ala Tyr Asn His Pro Ser Ser Ser Ile Gly Val
            520                 525                 530 ttc ttc tgt gga cct aaa gct ctc tcg agg aca ctt caa aag atg tgc         1747
Phe Phe Cys Gly Pro Lys Ala Leu Ser Arg Thr Leu Gln Lys Met Cys
        535                 540                 545 cac ttg tat tca tca gct gac ccc aga ggt gtt cat ttc tat tac aac         1795
His Leu Tyr Ser Ser Ala Asp Pro Arg Gly Val His Phe Tyr Tyr Asn
    550                 555                 560 aag gag agc ttc tag actttggagg tcaagtccag gcattgtgtt ttcaatcaag         1850
Lys Glu Ser Phe
565 ttattgattc caaagaactc caccaggaat tcctgtgacg gcctgttgat atgagctccc       1910 agttgggaac tggtgaataa taattaacta ttgtgaacag tacactatac catacttcct       1970 tagcttataa ataacatgtc atatacaaca gaacaaaaac atttactgaa attaaaatat       2030 attatgtttc tcca                                                         2044

<210> SEQ ID NO 6
<211> LENGTH: 568
<212> TYPE: PRT
<213> ORGANISM: Homo sapiens

<400> SEQUENCE: 6

Met Met Gly Cys Trp Ile Leu Asn Glu Gly Leu Ser Thr Ile Leu Val
1               5                   10                  15

Leu Ser Trp Leu Gly Ile Asn Phe Tyr Leu Phe Ile Asp Thr Phe Tyr
            20                  25                  30

Trp Tyr Glu Glu Glu Ser Phe His Tyr Thr Arg Val Ile Leu Gly
        35                  40                  45
```

```
Ser Thr Leu Ala Trp Ala Arg Ala Ser Ala Leu Cys Leu Asn Phe Asn
    50                  55                  60

Cys Met Leu Ile Leu Ile Pro Val Ser Arg Asn Leu Ile Ser Phe Ile
65                  70                  75                  80

Arg Gly Thr Ser Ile Cys Cys Arg Gly Pro Trp Arg Gln Leu Asp
                85                  90                  95

Lys Asn Leu Arg Phe His Lys Leu Val Ala Tyr Gly Ile Ala Val Asn
                100                 105                 110

Ala Thr Ile His Ile Val Ala His Phe Phe Asn Leu Glu Arg Tyr His
            115                 120                 125

Trp Ser Gln Ser Glu Glu Ala Gln Gly Leu Leu Ala Ala Leu Ser Lys
    130                 135                 140

Leu Gly Asn Thr Pro Asn Glu Ser Tyr Leu Asn Pro Val Arg Thr Phe
145                 150                 155                 160

Pro Thr Asn Thr Thr Thr Glu Leu Leu Arg Thr Ile Ala Gly Val Thr
                165                 170                 175

Gly Leu Val Ile Ser Leu Ala Leu Val Leu Ile Met Thr Ser Ser Thr
                180                 185                 190

Glu Phe Ile Arg Gln Ala Ser Tyr Glu Leu Phe Trp Tyr Thr His His
            195                 200                 205

Val Phe Ile Val Phe Phe Leu Ser Leu Ala Ile His Gly Thr Gly Arg
210                 215                 220

Ile Val Arg Gly Gln Thr Gln Asp Ser Leu Ser Leu His Asn Ile Thr
225                 230                 235                 240

Phe Cys Arg Asp Arg Tyr Ala Glu Trp Gln Thr Val Ala Gln Cys Pro
                245                 250                 255

Val Pro Gln Phe Ser Gly Lys Glu Pro Ser Ala Trp Lys Trp Ile Leu
            260                 265                 270

Gly Pro Val Val Leu Tyr Ala Cys Glu Arg Ile Ile Arg Phe Trp Arg
        275                 280                 285

Phe Gln Gln Glu Val Val Ile Thr Lys Val Val Ser His Pro Ser Gly
290                 295                 300

Val Leu Glu Leu His Met Lys Lys Arg Gly Phe Lys Met Ala Pro Gly
305                 310                 315                 320

Gln Tyr Ile Leu Val Gln Cys Pro Ala Ile Ser Ser Leu Glu Trp His
                325                 330                 335

Pro Phe Thr Leu Thr Ser Ala Pro Gln Glu Asp Phe Phe Ser Val His
            340                 345                 350

Ile Arg Ala Ala Gly Asp Trp Thr Ala Ala Leu Leu Glu Ala Phe Gly
        355                 360                 365

Ala Glu Gly Gln Ala Leu Gln Glu Pro Trp Ser Leu Pro Arg Leu Ala
    370                 375                 380

Val Asp Gly Pro Phe Gly Thr Ala Leu Thr Asp Val Phe His Tyr Pro
385                 390                 395                 400

Val Cys Val Cys Val Ala Ala Gly Ile Gly Val Thr Pro Phe Ala Ala
                405                 410                 415

Leu Leu Lys Ser Ile Trp Tyr Lys Cys Ser Glu Ala Gln Thr Pro Leu
            420                 425                 430

Lys Leu Ser Lys Val Tyr Phe Tyr Trp Ile Cys Arg Asp Ala Arg Ala
        435                 440                 445

Phe Glu Trp Phe Ala Asp Leu Leu Leu Ser Leu Glu Thr Arg Met Ser
450                 455                 460
```

-continued

| | | | | | | | | | | | | | | | |
|---|---|---|---|---|---|---|---|---|---|---|---|---|---|---|---|
|Glu|Gln|Gly|Lys|Thr|His|Phe|Leu|Ser|Tyr|His|Ile|Phe|Leu|Thr|Gly|
|465| | | | |470| | | | |475| | | | |480|

| | | | | | | | | | | | | | | | |
|---|---|---|---|---|---|---|---|---|---|---|---|---|---|---|---|
|Trp|Asp|Glu|Asn|Gln|Ala|Leu|His|Ile|Ala|Leu|His|Trp|Asp|Glu|Asn|
| | | | |485| | | | |490| | | | |495| |

| | | | | | | | | | | | | | | | |
|---|---|---|---|---|---|---|---|---|---|---|---|---|---|---|---|
|Thr|Asp|Val|Ile|Thr|Gly|Leu|Lys|Gln|Lys|Thr|Phe|Tyr|Gly|Arg|Pro|
| | | |500| | | | |505| | | | |510| | |

| | | | | | | | | | | | | | | | |
|---|---|---|---|---|---|---|---|---|---|---|---|---|---|---|---|
|Asn|Trp|Asn|Asn|Glu|Phe|Lys|Gln|Ile|Ala|Tyr|Asn|His|Pro|Ser|Ser|
| | |515| | | | |520| | | | |525| | | |

| | | | | | | | | | | | | | | | |
|---|---|---|---|---|---|---|---|---|---|---|---|---|---|---|---|
|Ser|Ile|Gly|Val|Phe|Phe|Cys|Gly|Pro|Lys|Ala|Leu|Ser|Arg|Thr|Leu|
| |530| | | | |535| | | | |540| | | | |

| | | | | | | | | | | | | | | | |
|---|---|---|---|---|---|---|---|---|---|---|---|---|---|---|---|
|Gln|Lys|Met|Cys|His|Leu|Tyr|Ser|Ser|Ala|Asp|Pro|Arg|Gly|Val|His|
|545| | | | |550| | | | |555| | | | |560|

| | | | | | |
|---|---|---|---|---|---|
|Phe|Tyr|Tyr|Asn|Lys|Glu|Ser|Phe|
| | | | |565| | | |

<210> SEQ ID NO 7
<211> LENGTH: 2232
<212> TYPE: DNA
<213> ORGANISM: Homo sapiens
<220> FEATURE:
<221> NAME/KEY: CDS
<222> LOCATION: (87)..(1823)

<400> SEQUENCE: 7

```
ccgcacaact gtaaccgctg ccccggccgc cgcccgctcc ttctcgggcc ggcgggcaca        60
gagcgcagcg cggcggggcc ggcggc atg gct gtg tcc tgg agg agc tgg ctc       113
                              Met Ala Val Ser Trp Arg Ser Trp Leu
                                1               5 gcc aac gaa ggg gtt aaa cac ctc tgc ctg ttc atc tgg ctc tcc atg        161
Ala Asn Glu Gly Val Lys His Leu Cys Leu Phe Ile Trp Leu Ser Met
 10                  15                  20                  25 aat gtc ctg ctt ttc tgg aaa acc ttc ttg ctg tat aac caa ggg cca        209
Asn Val Leu Leu Phe Trp Lys Thr Phe Leu Leu Tyr Asn Gln Gly Pro
                 30                  35                  40 gag tat cac tac ctc cac cag atg ttg ggg cta gga ttg tgt cta agc        257
Glu Tyr His Tyr Leu His Gln Met Leu Gly Leu Gly Leu Cys Leu Ser
             45                  50                  55 aga gcc tca gca tct gtt ctt aac ctc aac tgc agc ctt atc ctt tta        305
Arg Ala Ser Ala Ser Val Leu Asn Leu Asn Cys Ser Leu Ile Leu Leu
         60                  65                  70 ccc atg tgc cga aca ctc ttg gct tac ctc cga gga tca cag aag gtt        353
Pro Met Cys Arg Thr Leu Leu Ala Tyr Leu Arg Gly Ser Gln Lys Val
 75                  80                  85 cca agc agg aga acc agg aga ttg ttg gat aaa agc aga aca ttc cat        401
Pro Ser Arg Arg Thr Arg Arg Leu Leu Asp Lys Ser Arg Thr Phe His
 90                  95                 100                 105 att acc tgt ggt gtt act atc tgt att ttc tca ggc gtg cat gtg gct        449
Ile Thr Cys Gly Val Thr Ile Cys Ile Phe Ser Gly Val His Val Ala
                110                 115                 120 gcc cat ctg gtg aat gcc ctc aac ttc tca gtg aat tac agt gaa gac        497
Ala His Leu Val Asn Ala Leu Asn Phe Ser Val Asn Tyr Ser Glu Asp
            125                 130                 135 ttt gtt gaa ctg aat gca gca aga tac cga gat gag gat cct aga aaa        545
Phe Val Glu Leu Asn Ala Ala Arg Tyr Arg Asp Glu Asp Pro Arg Lys
        140                 145                 150 ctt ctc ttc aca act gtt cct ggc ctg aca ggg gtc tgc atg gtg gtg        593
Leu Leu Phe Thr Thr Val Pro Gly Leu Thr Gly Val Cys Met Val Val
    155                 160                 165 gtg cta ttc ctc atg atc aca gcc tct aca tat gca ata aga gtt tct        641
```

```
        Val Leu Phe Leu Met Ile Thr Ala Ser Thr Tyr Ala Ile Arg Val Ser
        170                 175                 180                 185 aac tat gat atc ttc tgg tat act cat aac ctc ttt gtc ttc tac              689
Asn Tyr Asp Ile Phe Trp Tyr Thr His Asn Leu Phe Val Phe Tyr
                190                 195                 200 atg ctg ctg acg ttg cat gtt tca gga ggg ctg ctg aag tat caa act          737
Met Leu Leu Thr Leu His Val Ser Gly Gly Leu Leu Lys Tyr Gln Thr
            205                 210                 215 aat tta gat acc cac cct ccc ggc tgc atc agt ctt aac cga acc agc          785
Asn Leu Asp Thr His Pro Pro Gly Cys Ile Ser Leu Asn Arg Thr Ser
        220                 225                 230 tct cag aat att tcc tta cca gag tat ttc tca gaa cat ttt cat gaa          833
Ser Gln Asn Ile Ser Leu Pro Glu Tyr Phe Ser Glu His Phe His Glu
    235                 240                 245 cct ttc cct gaa gga ttt tca aaa ccg gca gag ttt acc cag cac aaa          881
Pro Phe Pro Glu Gly Phe Ser Lys Pro Ala Glu Phe Thr Gln His Lys
250                 255                 260                 265 ttt gtg aag att tgt atg gaa gag ccc aga ttc caa gct aat ttt cca          929
Phe Val Lys Ile Cys Met Glu Glu Pro Arg Phe Gln Ala Asn Phe Pro
                270                 275                 280 cag act tgg ctt tgg att tct gga cct ttg tgc ctg tac tgt gcc gaa          977
Gln Thr Trp Leu Trp Ile Ser Gly Pro Leu Cys Leu Tyr Cys Ala Glu
            285                 290                 295 aga ctt tac agg tat atc cgg agc aat aag cca gtc acc atc att tcg         1025
Arg Leu Tyr Arg Tyr Ile Arg Ser Asn Lys Pro Val Thr Ile Ile Ser
        300                 305                 310 gtc ata agt cat ccc tca gat gtc atg gaa atc cga atg gtc aaa gaa         1073
Val Ile Ser His Pro Ser Asp Val Met Glu Ile Arg Met Val Lys Glu
    315                 320                 325 aat ttt aaa gca aga cct ggt cag tat att act cta cat tgt ccc agt         1121
Asn Phe Lys Ala Arg Pro Gly Gln Tyr Ile Thr Leu His Cys Pro Ser
330                 335                 340                 345 gta tct gca tta gaa aat cat cca ttt acc ctc aca atg tgt cca act         1169
Val Ser Ala Leu Glu Asn His Pro Phe Thr Leu Thr Met Cys Pro Thr
                350                 355                 360 gaa acc aaa gca aca ttt ggg gtt cat ctt aaa ata gta gga gac tgg         1217
Glu Thr Lys Ala Thr Phe Gly Val His Leu Lys Ile Val Gly Asp Trp
            365                 370                 375 aca gaa cga ttt cga gat tta cta ctg cct cca tct agt caa gac tcc         1265
Thr Glu Arg Phe Arg Asp Leu Leu Leu Pro Pro Ser Ser Gln Asp Ser
        380                 385                 390 gaa att ctg ccc ttc att caa tct aga aat tat ccc aag ctg tat att         1313
Glu Ile Leu Pro Phe Ile Gln Ser Arg Asn Tyr Pro Lys Leu Tyr Ile
    395                 400                 405 gat ggt cct ttt gga agt cca ttt gag gaa tca ctg aac tat gag gtc         1361
Asp Gly Pro Phe Gly Ser Pro Phe Glu Glu Ser Leu Asn Tyr Glu Val
410                 415                 420                 425 agc ctc tgc gtg gct gga ggc att gga gta act cca ttt gca tca ata         1409
Ser Leu Cys Val Ala Gly Gly Ile Gly Val Thr Pro Phe Ala Ser Ile
                430                 435                 440 ctc aac acc ctg ttg gat gac tgg aaa cca tac aag ctt aga aga cta         1457
Leu Asn Thr Leu Leu Asp Asp Trp Lys Pro Tyr Lys Leu Arg Arg Leu
            445                 450                 455 tac ttt att tgg gta tgc aga gat atc cag tcc ttc cgt tgg ttt gca         1505
Tyr Phe Ile Trp Val Cys Arg Asp Ile Gln Ser Phe Arg Trp Phe Ala
        460                 465                 470 gat tta ctc tgt atg ttg cat aac aag ttt tgg caa gag aac aga cct         1553
Asp Leu Leu Cys Met Leu His Asn Lys Phe Trp Gln Glu Asn Arg Pro
    475                 480                 485
```

-continued

```
gac tat gtc aac atc cag ctg tac ctc agt caa aca gat ggg ata cag    1601
Asp Tyr Val Asn Ile Gln Leu Tyr Leu Ser Gln Thr Asp Gly Ile Gln
490             495                 500                 505 aag ata att gga gaa aaa tat cat gca ctg aat tca aga ctg ttt ata    1649
Lys Ile Ile Gly Glu Lys Tyr His Ala Leu Asn Ser Arg Leu Phe Ile
        510                 515                 520 gga cgt cct cgg tgg aaa ctt ttg ttt gat gaa ata gca aaa tat aac    1697
Gly Arg Pro Arg Trp Lys Leu Leu Phe Asp Glu Ile Ala Lys Tyr Asn
525                 530                 535 aga gga aaa aca gtt ggt gtt ttc tgt tgt gga ccc aat tca cta tcc    1745
Arg Gly Lys Thr Val Gly Val Phe Cys Cys Gly Pro Asn Ser Leu Ser
        540                 545                 550 aag act ctt cat aaa ctg agt aac cag aac aac tca tat ggg aca aga    1793
Lys Thr Leu His Lys Leu Ser Asn Gln Asn Asn Ser Tyr Gly Thr Arg
555                 560                 565 ttt gaa tac aat aaa gag tct ttc agc tga aaacttttgc catgaagcag     1843
Phe Glu Tyr Asn Lys Glu Ser Phe Ser
570                 575 gactctaaag aaggaatgag tgcaatttct aagactttga aactcagcgg aatcaatcag   1903
ctgtgttatg ccaaagaata gtaaggtttt cttatttatg attatttgaa aatggaaatg   1963
tgagaatgtg gcaacatgac cgtcacatta catgtttaat ctggaaacca agagaccct   2023 gaagaatatt tgatgtgatg attcattttc agttctcaaa ttaaagaaa actgttagat    2083 gcacactgtt gattttcatg gtggattcaa gaactcccta gtgaggagct gaacttgctc   2143
aatctaaggc tgattgtcgt gttcctcttt aaattgtttt tggttgaaca aatgcaagat   2203
tgaacaaaat taaaaattca ttgaagctg                                    2232
```

<210> SEQ ID NO 8
<211> LENGTH: 578
<212> TYPE: PRT
<213> ORGANISM: Homo sapiens

<400> SEQUENCE: 8

```
Met Ala Val Ser Trp Arg Ser Trp Leu Ala Asn Glu Gly Val Lys His
1               5                   10                  15

Leu Cys Leu Phe Ile Trp Leu Ser Met Asn Val Leu Leu Phe Trp Lys
            20                  25                  30

Thr Phe Leu Leu Tyr Asn Gln Gly Pro Glu Tyr His Tyr Leu His Gln
        35                  40                  45

Met Leu Gly Leu Gly Leu Cys Leu Ser Arg Ala Ser Ala Ser Val Leu
    50                  55                  60

Asn Leu Asn Cys Ser Leu Ile Leu Pro Met Cys Arg Thr Leu Leu
65                  70                  75                  80

Ala Tyr Leu Arg Gly Ser Gln Lys Val Pro Ser Arg Thr Arg Arg
                85                  90                  95

Leu Leu Asp Lys Ser Arg Thr Phe His Ile Thr Cys Gly Val Thr Ile
            100                 105                 110

Cys Ile Phe Ser Gly Val His Val Ala Ala His Leu Val Asn Ala Leu
        115                 120                 125

Asn Phe Ser Val Asn Tyr Ser Glu Asp Phe Val Glu Leu Asn Ala Ala
    130                 135                 140

Arg Tyr Arg Asp Glu Asp Pro Arg Lys Leu Leu Phe Thr Thr Val Pro
145                 150                 155                 160

Gly Leu Thr Gly Val Cys Met Val Val Leu Phe Leu Met Ile Thr
                165                 170                 175
```

```
Ala Ser Thr Tyr Ala Ile Arg Val Ser Asn Tyr Asp Ile Phe Trp Tyr
            180                 185                 190
Thr His Asn Leu Phe Phe Val Phe Tyr Met Leu Leu Thr Leu His Val
        195                 200                 205
Ser Gly Gly Leu Leu Lys Tyr Gln Thr Asn Leu Asp Thr His Pro Pro
    210                 215                 220
Gly Cys Ile Ser Leu Asn Arg Thr Ser Ser Gln Asn Ile Ser Leu Pro
225                 230                 235                 240
Glu Tyr Phe Ser Glu His Phe His Glu Pro Phe Pro Glu Gly Phe Ser
                245                 250                 255
Lys Pro Ala Glu Phe Thr Gln His Lys Phe Val Lys Ile Cys Met Glu
            260                 265                 270
Glu Pro Arg Phe Gln Ala Asn Phe Pro Gln Thr Trp Leu Trp Ile Ser
        275                 280                 285
Gly Pro Leu Cys Leu Tyr Cys Ala Glu Arg Leu Tyr Arg Tyr Ile Arg
    290                 295                 300
Ser Asn Lys Pro Val Thr Ile Ile Ser Val Ile Ser His Pro Ser Asp
305                 310                 315                 320
Val Met Glu Ile Arg Met Val Lys Glu Asn Phe Lys Ala Arg Pro Gly
                325                 330                 335
Gln Tyr Ile Thr Leu His Cys Pro Ser Val Ser Ala Leu Glu Asn His
            340                 345                 350
Pro Phe Thr Leu Thr Met Cys Pro Thr Glu Thr Lys Ala Thr Phe Gly
        355                 360                 365
Val His Leu Lys Ile Val Gly Asp Trp Thr Glu Arg Phe Arg Asp Leu
    370                 375                 380
Leu Leu Pro Pro Ser Ser Gln Asp Ser Glu Ile Leu Pro Phe Ile Gln
385                 390                 395                 400
Ser Arg Asn Tyr Pro Lys Leu Tyr Ile Asp Gly Pro Phe Gly Ser Pro
                405                 410                 415
Phe Glu Glu Ser Leu Asn Tyr Glu Val Ser Leu Cys Val Ala Gly Gly
            420                 425                 430
Ile Gly Val Thr Pro Phe Ala Ser Ile Leu Asn Thr Leu Leu Asp Asp
        435                 440                 445
Trp Lys Pro Tyr Lys Leu Arg Arg Leu Tyr Phe Ile Trp Val Cys Arg
    450                 455                 460
Asp Ile Gln Ser Phe Arg Trp Phe Ala Asp Leu Leu Cys Met Leu His
465                 470                 475                 480
Asn Lys Phe Trp Gln Glu Asn Arg Pro Asp Tyr Val Asn Ile Gln Leu
                485                 490                 495
Tyr Leu Ser Gln Thr Asp Gly Ile Gln Lys Ile Gly Glu Lys Tyr
            500                 505                 510
His Ala Leu Asn Ser Arg Leu Phe Ile Gly Arg Pro Arg Trp Lys Leu
        515                 520                 525
Leu Phe Asp Glu Ile Ala Lys Tyr Asn Arg Gly Lys Thr Val Gly Val
    530                 535                 540
Phe Cys Cys Gly Pro Asn Ser Leu Ser Lys Thr Leu His Lys Leu Ser
545                 550                 555                 560
Asn Gln Asn Asn Ser Tyr Gly Thr Arg Phe Glu Tyr Asn Lys Glu Ser
                565                 570                 575
Phe Ser

<210> SEQ ID NO 9
```

<211> LENGTH: 2223
<212> TYPE: DNA
<213> ORGANISM: Homo sapiens
<220> FEATURE:
<221> NAME/KEY: CDS
<222> LOCATION: (73)..(1770)

<400> SEQUENCE: 9

```
gccgacgcgg acggcaacgg ggccatcacc ttcgaggagc tccgggacga gctgcagcgc      60
ttccccggag tc atg gag aac ctg acc atc agc act gcc cac tgg ctg acg     111
              Met Glu Asn Leu Thr Ile Ser Thr Ala His Trp Leu Thr
                1               5                  10 gcc ccc gcc ccc cgc cca cgc ccg cgc cgg ccg cgc cag ctg acc cgc       159
Ala Pro Ala Pro Arg Pro Arg Pro Arg Arg Pro Arg Gln Leu Thr Arg
 15              20                  25 gcc tac tgg cac aac cac cgc agc cag ctg ttc tgc ctg gcc acc tat       207
Ala Tyr Trp His Asn His Arg Ser Gln Leu Phe Cys Leu Ala Thr Tyr
 30              35                  40                  45 gca ggc ctc cac gtg ctg ctc ttc ggg ctg gcg gcc agc gcg cac cgg       255
Ala Gly Leu His Val Leu Leu Phe Gly Leu Ala Ala Ser Ala His Arg
             50                  55                  60 gac ctc ggc gcc agc gtc atg gtg gcc aag ggc tgt ggc cag tgc ctc       303
Asp Leu Gly Ala Ser Val Met Val Ala Lys Gly Cys Gly Gln Cys Leu
         65                  70                  75 aac ttc gac tgc agc ttc atc gcg gtg ctg atg ctc aga cgc tgc ctc       351
Asn Phe Asp Cys Ser Phe Ile Ala Val Leu Met Leu Arg Arg Cys Leu
     80                  85                  90 acc tgg ctg cgg gcc acg tgg ctg gct caa gtc cta cca ctg gac cag       399
Thr Trp Leu Arg Ala Thr Trp Leu Ala Gln Val Leu Pro Leu Asp Gln
 95                 100                 105 aac atc cag ttc cac cag ctt atg ggc tac gtg gta gtg ggg ctg tcc       447
Asn Ile Gln Phe His Gln Leu Met Gly Tyr Val Val Val Gly Leu Ser
110                 115                 120                 125 ctc gtg cac act gtg gct cac act gtg aac ttt gta ctc cag gct cag       495
Leu Val His Thr Val Ala His Thr Val Asn Phe Val Leu Gln Ala Gln
            130                 135                 140 gcg gag gcc agc cct ttc cag ttc tgg gag ctg ctc acc acg agg           543
Ala Glu Ala Ser Pro Phe Gln Phe Trp Glu Leu Leu Leu Thr Thr Arg
        145                 150                 155 cct ggc att ggc tgg gta cac ggt tcg gcc tcc ccg aca ggt gtc gct       591
Pro Gly Ile Gly Trp Val His Gly Ser Ala Ser Pro Thr Gly Val Ala
    160                 165                 170 ctg ctg ctg ctc ctc ctc atg ttc atc tgc tcc agt tcc tgc atc           639
Leu Leu Leu Leu Leu Leu Leu Met Phe Ile Cys Ser Ser Ser Cys Ile
175                 180                 185 cgc agg agt ggc cac ttt gag gtg ttc tat tgg act cac ctg tcc tac       687
Arg Arg Ser Gly His Phe Glu Val Phe Tyr Trp Thr His Leu Ser Tyr
190                 195                 200                 205 ctc ctc gtg tgg ctt ctg ctc atc ttt cat ggg ccc aac ttc tgg aag       735
Leu Leu Val Trp Leu Leu Leu Ile Phe His Gly Pro Asn Phe Trp Lys
            210                 215                 220 tgg ctg ctg gtg cct gga atc ttg ttt ttc ctg gag aag gcc atc gga       783
Trp Leu Leu Val Pro Gly Ile Leu Phe Phe Leu Glu Lys Ala Ile Gly
        225                 230                 235 ctg gca gtg tcc cgc atg gca gcc gtg tgc atc atg gaa gtc aac ctc       831
Leu Ala Val Ser Arg Met Ala Ala Val Cys Ile Met Glu Val Asn Leu
    240                 245                 250 ctc ccc tcc aag gtc act cat ctc ctc atc aag cgg ccc cct ttt ttt       879
Leu Pro Ser Lys Val Thr His Leu Leu Ile Lys Arg Pro Pro Phe Phe
255                 260                 265
```

-continued

| | |
|---|---|
| cac tat aga cct ggt gac tac ttg tat ctg aac atc ccc acc att gct<br>His Tyr Arg Pro Gly Asp Tyr Leu Tyr Leu Asn Ile Pro Thr Ile Ala<br>270                275              280              285 | 927 |
| cgc tat gag tgg cac ccc ttc acc atc agc agt gct cct gag cag aaa<br>Arg Tyr Glu Trp His Pro Phe Thr Ile Ser Ser Ala Pro Glu Gln Lys<br>              290              295              300 | 975 |
| gac act atc tgg ctg cac att cgg tcc caa ggc cag tgg aca aac agg<br>Asp Thr Ile Trp Leu His Ile Arg Ser Gln Gly Gln Trp Thr Asn Arg<br>305                310              315 | 1023 |
| ctg tat gag tcc ttc aag gca tca gac cca ctg ggc cgt ggt tct aag<br>Leu Tyr Glu Ser Phe Lys Ala Ser Asp Pro Leu Gly Arg Gly Ser Lys<br>        320              325              330 | 1071 |
| agg ctg tcg agg agt gtg aca atg aga aag agt caa agg tcg tcc aag<br>Arg Leu Ser Arg Ser Val Thr Met Arg Lys Ser Gln Arg Ser Ser Lys<br>335                340              345 | 1119 |
| ggc tct gag ata ctt ttg gag aaa cac aaa ttc tgt aac atc aag tgc<br>Gly Ser Glu Ile Leu Leu Glu Lys His Lys Phe Cys Asn Ile Lys Cys<br>350                355              360              365 | 1167 |
| tac atc gat ggg cct tat ggg acc ccc acc cgc agg atc ttt gcc tct<br>Tyr Ile Asp Gly Pro Tyr Gly Thr Pro Thr Arg Arg Ile Phe Ala Ser<br>              370              375              380 | 1215 |
| gag cat gcc gtg ctc atc ggg gca ggc atc ggc atc acc ccc ttt gct<br>Glu His Ala Val Leu Ile Gly Ala Gly Ile Gly Ile Thr Pro Phe Ala<br>              385              390              395 | 1263 |
| tcc att ctg cag agt atc atg tac agg cac cag aaa aga aag cat act<br>Ser Ile Leu Gln Ser Ile Met Tyr Arg His Gln Lys Arg Lys His Thr<br>400                405              410 | 1311 |
| tgc ccc agc tgc cag cac tcc tgg atc gaa ggt gtc caa gac aac atg<br>Cys Pro Ser Cys Gln His Ser Trp Ile Glu Gly Val Gln Asp Asn Met<br>415                420              425 | 1359 |
| aag ctc cat aag gtg gac ttt atc tgg atc aac aga gac cag cgg tct<br>Lys Leu His Lys Val Asp Phe Ile Trp Ile Asn Arg Asp Gln Arg Ser<br>430                435              440              445 | 1407 |
| ttc gag tgg ttt gtg agc ctg ctg act aaa ctg gag atg gac cag gcc<br>Phe Glu Trp Phe Val Ser Leu Leu Thr Lys Leu Glu Met Asp Gln Ala<br>              450              455              460 | 1455 |
| gag gag gct caa tac ggc cgc ttc ctg gag ctg cat atg tac atg aca<br>Glu Glu Ala Gln Tyr Gly Arg Phe Leu Glu Leu His Met Tyr Met Thr<br>              465              470              475 | 1503 |
| tct gca ctg ggc aag aat gac atg aag gcc att ggc ctg cag atg gcc<br>Ser Ala Leu Gly Lys Asn Asp Met Lys Ala Ile Gly Leu Gln Met Ala<br>        480              485              490 | 1551 |
| ctt gac ctc ctg gcc aac aag gag aag aaa gac tcc atc acg ggg ctg<br>Leu Asp Leu Leu Ala Asn Lys Glu Lys Lys Asp Ser Ile Thr Gly Leu<br>495                500              505 | 1599 |
| cag acg cgc acc cag cct ggg cgg cct gac tgg agc aag gtg ttc cag<br>Gln Thr Arg Thr Gln Pro Gly Arg Pro Asp Trp Ser Lys Val Phe Gln<br>510                515              520              525 | 1647 |
| aaa gtg gct gct gag aag aag ggc aag gtg cag gtc ttc ttc tgt ggc<br>Lys Val Ala Ala Glu Lys Lys Gly Lys Val Gln Val Phe Phe Cys Gly<br>              530              535              540 | 1695 |
| tcc cca gct ctg gcc aag gtg ctg aag ggc cat tgt gag aag ttc ggc<br>Ser Pro Ala Leu Ala Lys Val Leu Lys Gly His Cys Glu Lys Phe Gly<br>        545              550              555 | 1743 |
| ttc aga ttt ttc caa gag aat ttc tag cctcacctct ccaagctctg<br>Phe Arg Phe Phe Gln Glu Asn Phe<br>560                565 | 1790 |
| ccccaagtcc acaccatggg tctgcttcat cgcattagta taaatgcccc cacagggacc | 1850 |
| agcctcagat gacccaccca ataagacaaa gcctagggac ccctaatcc tgctcaacag | 1910 |

-continued

```
agagaacagg agaccccaag gggcagatga acttcctcta gaacccaggg gaaggggcag    1970
tgccttgttc agtctgctgt agattctggg gtttctgtga aagtgaggga accagaggct    2030
ggtcacggga gcttgggggt ggggttcgag ggggcagagg gcaaccactc ctccaaacat    2090
tttccgacgg agccttcccc cacatccatg gtcccaaacc tgcccaatca tcacagtcat    2150
ttggaagctt atttctccgg catcttataa aattgttcaa acctacagta aaaaaaaaa     2210 aaaaaaaaaa aaa                                                       2223
```

<210> SEQ ID NO 10
<211> LENGTH: 565
<212> TYPE: PRT
<213> ORGANISM: Homo sapiens

<400> SEQUENCE: 10

```
Met Glu Asn Leu Thr Ile Ser Thr Ala His Trp Leu Thr Ala Pro Ala
1               5                   10                  15

Pro Arg Pro Arg Pro Arg Pro Arg Gln Leu Thr Arg Ala Tyr Trp
            20                  25                  30

His Asn His Arg Ser Gln Leu Phe Cys Leu Ala Thr Tyr Ala Gly Leu
        35                  40                  45

His Val Leu Leu Phe Gly Leu Ala Ala Ser Ala His Arg Asp Leu Gly
    50                  55                  60

Ala Ser Val Met Val Ala Lys Gly Cys Gly Gln Cys Leu Asn Phe Asp
65                  70                  75                  80

Cys Ser Phe Ile Ala Val Leu Met Leu Arg Arg Cys Leu Thr Trp Leu
                85                  90                  95

Arg Ala Thr Trp Leu Ala Gln Val Leu Pro Leu Asp Gln Asn Ile Gln
            100                 105                 110

Phe His Gln Leu Met Gly Tyr Val Val Gly Leu Ser Leu Val His
        115                 120                 125

Thr Val Ala His Thr Val Asn Phe Val Leu Gln Ala Gln Ala Glu Ala
    130                 135                 140

Ser Pro Phe Gln Phe Trp Glu Leu Leu Leu Thr Thr Arg Pro Gly Ile
145                 150                 155                 160

Gly Trp Val His Gly Ser Ala Ser Pro Thr Gly Val Ala Leu Leu Leu
                165                 170                 175

Leu Leu Leu Leu Met Phe Ile Cys Ser Ser Cys Ile Arg Arg Ser
            180                 185                 190

Gly His Phe Glu Val Phe Tyr Trp Thr His Leu Ser Tyr Leu Leu Val
        195                 200                 205

Trp Leu Leu Leu Ile Phe His Gly Pro Asn Phe Trp Lys Trp Leu Leu
    210                 215                 220

Val Pro Gly Ile Leu Phe Phe Leu Glu Lys Ala Ile Gly Leu Ala Val
225                 230                 235                 240

Ser Arg Met Ala Ala Val Cys Ile Met Glu Val Asn Leu Leu Pro Ser
                245                 250                 255

Lys Val Thr His Leu Leu Ile Lys Pro Pro Phe Phe His Tyr Arg
            260                 265                 270

Pro Gly Asp Tyr Leu Tyr Leu Asn Ile Pro Thr Ile Ala Arg Tyr Glu
        275                 280                 285

Trp His Pro Phe Thr Ile Ser Ser Ala Pro Glu Gln Lys Asp Thr Ile
    290                 295                 300

Trp Leu His Ile Arg Ser Gln Gly Gln Trp Thr Asn Arg Leu Tyr Glu
```

```
                    305                 310                 315                 320
              Ser Phe Lys Ala Ser Asp Pro Leu Gly Arg Gly Ser Lys Arg Leu Ser
                          325                 330                 335

Arg Ser Val Thr Met Arg Lys Ser Gln Arg Ser Ser Lys Gly Ser Glu
                          340                 345                 350

Ile Leu Leu Glu Lys His Lys Phe Cys Asn Ile Lys Cys Tyr Ile Asp
                          355                 360                 365

Gly Pro Tyr Gly Thr Pro Thr Arg Arg Ile Phe Ala Ser Glu His Ala
                    370                 375                 380

Val Leu Ile Gly Ala Gly Ile Gly Ile Thr Pro Phe Ala Ser Ile Leu
              385                 390                 395                 400

Gln Ser Ile Met Tyr Arg His Gln Lys Arg Lys His Thr Cys Pro Ser
                          405                 410                 415

Cys Gln His Ser Trp Ile Glu Gly Val Gln Asp Asn Met Lys Leu His
                          420                 425                 430

Lys Val Asp Phe Ile Trp Ile Asn Arg Asp Gln Arg Ser Phe Glu Trp
                          435                 440                 445

Phe Val Ser Leu Leu Thr Lys Leu Glu Met Asp Gln Ala Glu Glu Ala
                    450                 455                 460

Gln Tyr Gly Arg Phe Leu Glu Leu His Met Tyr Met Thr Ser Ala Leu
              465                 470                 475                 480

Gly Lys Asn Asp Met Lys Ala Ile Gly Leu Gln Met Ala Leu Asp Leu
                          485                 490                 495

Leu Ala Asn Lys Glu Lys Asp Ser Ile Thr Gly Leu Gln Thr Arg
                          500                 505                 510

Thr Gln Pro Gly Arg Pro Asp Trp Ser Lys Val Phe Gln Lys Val Ala
                          515                 520                 525

Ala Glu Lys Lys Gly Lys Val Gln Val Phe Phe Cys Gly Ser Pro Ala
                    530                 535                 540

Leu Ala Lys Val Leu Lys Gly His Cys Glu Lys Phe Gly Phe Arg Phe
              545                 550                 555                 560

Phe Gln Glu Asn Phe
                          565

<210> SEQ ID NO 11
<211> LENGTH: 5693
<212> TYPE: DNA
<213> ORGANISM: Homo sapiens
<220> FEATURE:
<221> NAME/KEY: CDS
<222> LOCATION: (347)..(5002)

<400> SEQUENCE: 11
gcagagctgc agaggcaccg gacgagagag ggctccgcgg gcccagctgg cagccaggcc      60
ggagacaagt tgcagtcccg ggctctggtg acgccgtggc cgcagctgga agaggaaaac     120
aaggatcaga ttggagaagt gatttatcta agatcccaca gtggactggc agcagcactg     180
agacctcagc ctagtctcct gatccccaag cagggccctg cctaaggaac acactctgca     240
gagtgctggg ccaaagcagg gttttccaac taatcttaga aggtaaagtc catgaaggt     300 ctccattttg ggacattcta atccctgagc cctattatt tccatc atg ggc ttc        355
                                                   Met Gly Phe
                                                     1 tgc ctg gct cta gca tgg aca ctt ctg gtt ggg gca tgg acc cct ctg      403
Cys Leu Ala Leu Ala Trp Thr Leu Leu Val Gly Ala Trp Thr Pro Leu
  5                  10                  15
```

```
gga gct cag aac ccc att tcg tgg gag gtg cag cga ttt gat ggg tgg     451
Gly Ala Gln Asn Pro Ile Ser Trp Glu Val Gln Arg Phe Asp Gly Trp
 20              25                  30                  35 tac aac aac ctc atg gag cac aga tgg ggc agc aaa ggc tcc cgg ctg     499
Tyr Asn Asn Leu Met Glu His Arg Trp Gly Ser Lys Gly Ser Arg Leu
                 40                  45                  50 cag cgc ctg gtc cca gcc agc tat gca gat ggc gtg tac cag ccc ttg     547
Gln Arg Leu Val Pro Ala Ser Tyr Ala Asp Gly Val Tyr Gln Pro Leu
             55                  60                  65 gga gaa ccc cac ctg ccc aac ccc cga gac ctt agc aac acc atc tca     595
Gly Glu Pro His Leu Pro Asn Pro Arg Asp Leu Ser Asn Thr Ile Ser
         70                  75                  80 agg ggc cct gca ggg ctg gcc tcc ctg aga aac cgc aca gtg ttg ggg     643
Arg Gly Pro Ala Gly Leu Ala Ser Leu Arg Asn Arg Thr Val Leu Gly
 85                  90                  95 gtc ttc ttt ggc tat cac gtg ctt tca gac ctg gtg agc gtg gaa act     691
Val Phe Phe Gly Tyr His Val Leu Ser Asp Leu Val Ser Val Glu Thr
100                 105                 110                 115 ccc ggc tgc ccc gcc gag ttc ctc aac att cgc atc ccg ccc gga gac     739
Pro Gly Cys Pro Ala Glu Phe Leu Asn Ile Arg Ile Pro Pro Gly Asp
                120                 125                 130 ccc atg ttc gac ccc gac cag cgc ggg gac gtg gtg ctg ccc ttc cag     787
Pro Met Phe Asp Pro Asp Gln Arg Gly Asp Val Val Leu Pro Phe Gln
            135                 140                 145 aga agc cgc tgg gac ccc gag acc gga cgg agt ccc agc aat ccc cgg     835
Arg Ser Arg Trp Asp Pro Glu Thr Gly Arg Ser Pro Ser Asn Pro Arg
        150                 155                 160 gac ccg gcc aac cag gtg acg ggc tgg ctg gac ggc agc gcc atc tat     883
Asp Pro Ala Asn Gln Val Thr Gly Trp Leu Asp Gly Ser Ala Ile Tyr
    165                 170                 175 ggt tcc tcg cat tcc tgg agc gac gcg ctg cgg agc ttc tcc agg gga     931
Gly Ser Ser His Ser Trp Ser Asp Ala Leu Arg Ser Phe Ser Arg Gly
180                 185                 190                 195 cag ctg gcg tcg ggg ccc gac ccc gct ttt ccc cga gac tcg cag aac     979
Gln Leu Ala Ser Gly Pro Asp Pro Ala Phe Pro Arg Asp Ser Gln Asn
                200                 205                 210 ccc ctg ctc atg tgg gcg gcg ccc gac ccc gcc acc ggg cag aac ggg    1027
Pro Leu Leu Met Trp Ala Ala Pro Asp Pro Ala Thr Gly Gln Asn Gly
            215                 220                 225 ccc cgg ggg ctg tac gcc ttc ggg gca gag aga ggg aac cgg gaa ccc    1075
Pro Arg Gly Leu Tyr Ala Phe Gly Ala Glu Arg Gly Asn Arg Glu Pro
        230                 235                 240 ttc ctg cag gcg ctg ggc ctg ctc tgg ttc cgc tac cac aac ctg tgg    1123
Phe Leu Gln Ala Leu Gly Leu Leu Trp Phe Arg Tyr His Asn Leu Trp
    245                 250                 255 gcg cag agg ctg gcc cgc cag cac cca gac tgg gag gac gag gag ctg    1171
Ala Gln Arg Leu Ala Arg Gln His Pro Asp Trp Glu Asp Glu Glu Leu
260                 265                 270                 275 ttc cag cac gca cgc aag agg gtc atc gcc acc tac cag aac atc gct    1219
Phe Gln His Ala Arg Lys Arg Val Ile Ala Thr Tyr Gln Asn Ile Ala
                280                 285                 290 gtg tat gag tgg ctg ccc agc ttc ctg cag aaa aca ctc ccg gag tat    1267
Val Tyr Glu Trp Leu Pro Ser Phe Leu Gln Lys Thr Leu Pro Glu Tyr
            295                 300                 305 aca gga tac cgg cca ttt ctg gac ccc agc atc tcc tca gag ttc gtg    1315
Thr Gly Tyr Arg Pro Phe Leu Asp Pro Ser Ile Ser Ser Glu Phe Val
        310                 315                 320 gcg gcc tct gag cag ttc ctg tcc acc atg gtg ccc cct ggc gtc tac    1363
Ala Ala Ser Glu Gln Phe Leu Ser Thr Met Val Pro Pro Gly Val Tyr
    325                 330                 335
```

-continued

```
atg aga aat gcc agc tgc cac ttc cag ggg gtc atc aat cgg aac tca        1411
Met Arg Asn Ala Ser Cys His Phe Gln Gly Val Ile Asn Arg Asn Ser
340             345                 350                 355 agt gtc tcc aga gct ctc cgg gtc tgc aac agc tac tgg agc cgt gag        1459
Ser Val Ser Arg Ala Leu Arg Val Cys Asn Ser Tyr Trp Ser Arg Glu
        360                 365                 370 cac cca agc cta caa agt gct gaa gat gtg gat gca ctg ctg ctg ggc        1507
His Pro Ser Leu Gln Ser Ala Glu Asp Val Asp Ala Leu Leu Leu Gly
            375                 380                 385 atg gcc tcc cag atc gca gag cga gag gac cat gtg ttg gtt gaa gat        1555
Met Ala Ser Gln Ile Ala Glu Arg Glu Asp His Val Leu Val Glu Asp
                390                 395                 400 gtg cgg gat ttc tgg cct ggg cca ctg aag ttt tcc cgc aca gac cac        1603
Val Arg Asp Phe Trp Pro Gly Pro Leu Lys Phe Ser Arg Thr Asp His
405                 410                 415 ctg gcc agc tgc ctg cag cgg ggc cgg gat ctg ggc ctg ccc tct tac        1651
Leu Ala Ser Cys Leu Gln Arg Gly Arg Asp Leu Gly Leu Pro Ser Tyr
420                 425                 430                 435 acc aag gcc agg gca gca ctg ggc ttg tct ccc att acc cgc tgg cag        1699
Thr Lys Ala Arg Ala Ala Leu Gly Leu Ser Pro Ile Thr Arg Trp Gln
                440                 445                 450 gac atc aac cct gca ctc tcc cgg agc aat gac act gta ctg gag gcc        1747
Asp Ile Asn Pro Ala Leu Ser Arg Ser Asn Asp Thr Val Leu Glu Ala
                455                 460                 465 aca gct gcc ctg tac aac cag gac tta tcc tgg cta gag ctg ctc cct        1795
Thr Ala Ala Leu Tyr Asn Gln Asp Leu Ser Trp Leu Glu Leu Leu Pro
                470                 475                 480 ggg gga ctc ctg gag agc cac cgg gac cct gga cct ctg ttc agc acc        1843
Gly Gly Leu Leu Glu Ser His Arg Asp Pro Gly Pro Leu Phe Ser Thr
            485                 490                 495 atc gtc ctt gaa caa ttt gtg cgg cta cgg gat ggt gac cgc tac tgg        1891
Ile Val Leu Glu Gln Phe Val Arg Leu Arg Asp Gly Asp Arg Tyr Trp
500                 505                 510                 515 ttt gag aac acc agg aat ggg ctg ttc tcc aag aag gag att gaa gaa        1939
Phe Glu Asn Thr Arg Asn Gly Leu Phe Ser Lys Lys Glu Ile Glu Glu
                520                 525                 530 atc cga aat acc acc ctg cag gac gtg ctg gtc gct gtt atc aac att        1987
Ile Arg Asn Thr Thr Leu Gln Asp Val Leu Val Ala Val Ile Asn Ile
                535                 540                 545 gac ccc agt gct ctg cag ccc aat gtc ttt gtc tgg cat aaa gga gac        2035
Asp Pro Ser Ala Leu Gln Pro Asn Val Phe Val Trp His Lys Gly Asp
            550                 555                 560 ccc tgt ccg cag ccg aga cag ctc agc act gaa ggc ctg cca gcg tgt        2083
Pro Cys Pro Gln Pro Arg Gln Leu Ser Thr Glu Gly Leu Pro Ala Cys
565                 570                 575 gct ccc tct gtt gtt cgt gac tat ttt gag ggc agt gga ttt ggc ttc        2131
Ala Pro Ser Val Val Arg Asp Tyr Phe Glu Gly Ser Gly Phe Gly Phe
580                 585                 590                 595 ggg gtc acc atc ggg acc ctc tgt tgc ttc cct ttg gtg agc ctg ctc        2179
Gly Val Thr Ile Gly Thr Leu Cys Cys Phe Pro Leu Val Ser Leu Leu
                600                 605                 610 agt gcc tgg att gtt gcc cgg ctc cgg atg aga aat ttc aag agg ctc        2227
Ser Ala Trp Ile Val Ala Arg Leu Arg Met Arg Asn Phe Lys Arg Leu
            615                 620                 625 cag ggc cag gac cgc cag agc atc gtg tct gag aag ctc gtg gga ggc        2275
Gln Gly Gln Asp Arg Gln Ser Ile Val Ser Glu Lys Leu Val Gly Gly
            630                 635                 640 atg gaa gct ttg gaa tgg caa ggc cac aag gag ccc tgc cgg ccc gtg        2323
Met Glu Ala Leu Glu Trp Gln Gly His Lys Glu Pro Cys Arg Pro Val
```

-continued

```
              645                 650                 655
ctt gtg tac ctg cag ccc ggg cag atc cgt gtg gta gat ggc agg ctc      2371
Leu Val Tyr Leu Gln Pro Gly Gln Ile Arg Val Val Asp Gly Arg Leu
660                 665                 670                 675 acc gtg ctc cgc acc atc cag ctg cag cct cca cag aag gtc aac ttc      2419
Thr Val Leu Arg Thr Ile Gln Leu Gln Pro Pro Gln Lys Val Asn Phe
                680                 685                 690 gtc ctg tcc agc aac cgt gga cgc cgc act ctg ctc ctc aag atc ccc      2467
Val Leu Ser Ser Asn Arg Gly Arg Arg Thr Leu Leu Leu Lys Ile Pro
                    695                 700                 705 aag gag tat gac ctg gtg ctg ctg ttt aac ttg gag gaa gag cgg cag      2515
Lys Glu Tyr Asp Leu Val Leu Leu Phe Asn Leu Glu Glu Glu Arg Gln
        710                 715                 720 gcg ctg gtg gaa aat ctc cgg gga gct ctg aag gag agc ggg ttg agc      2563
Ala Leu Val Glu Asn Leu Arg Gly Ala Leu Lys Glu Ser Gly Leu Ser
            725                 730                 735 atc cag gag tgg gag ctg cgg gag cag gag ctg atg aga gca gct gtg      2611
Ile Gln Glu Trp Glu Leu Arg Glu Gln Glu Leu Met Arg Ala Ala Val
740                 745                 750                 755 aca cgg gag cag cgg agg cac ctc ctg gag acc ttt ttc agg cac ctt      2659
Thr Arg Glu Gln Arg Arg His Leu Leu Glu Thr Phe Phe Arg His Leu
                760                 765                 770 ttc tcc cag gtg ctg gac atc aac cag gcc gac gca ggg acc ctg ccc      2707
Phe Ser Gln Val Leu Asp Ile Asn Gln Ala Asp Ala Gly Thr Leu Pro
                    775                 780                 785 ctg gac tcc tcc cag aag gtg cgg gag gcc ctg acc tgt gag ctg agc      2755
Leu Asp Ser Ser Gln Lys Val Arg Glu Ala Leu Thr Cys Glu Leu Ser
        790                 795                 800 agg gcc gag ttt gcc gag tcc ctg ggc ctc aag ccc cag gac atg ttt      2803
Arg Ala Glu Phe Ala Glu Ser Leu Gly Leu Lys Pro Gln Asp Met Phe
805                 810                 815 gtg gag tcc atg ttc tct ctg gct gac aag gat ggc aat ggc tac ctg      2851
Val Glu Ser Met Phe Ser Leu Ala Asp Lys Asp Gly Asn Gly Tyr Leu
820                 825                 830                 835 tcc ttc cga gag ttc ctg gac atc ctg gtg gtc ttc atg aaa ggc tct      2899
Ser Phe Arg Glu Phe Leu Asp Ile Leu Val Val Phe Met Lys Gly Ser
                840                 845                 850 cct gag gaa aag tct cgc ctt atg ttc cgc atg tac gac ttt gat ggg      2947
Pro Glu Glu Lys Ser Arg Leu Met Phe Arg Met Tyr Asp Phe Asp Gly
                    855                 860                 865 aat ggc ctc att tcc aag gat gag ttc atc agg atg ctg aga tcc ttc      2995
Asn Gly Leu Ile Ser Lys Asp Glu Phe Ile Arg Met Leu Arg Ser Phe
        870                 875                 880 atc gag atc tcc aac aac tgc ctg tcc aag gcc cag ctg gct gag gtg      3043
Ile Glu Ile Ser Asn Asn Cys Leu Ser Lys Ala Gln Leu Ala Glu Val
885                 890                 895 gtg gag tcc atg ttc cgg gag tcg gga ttc cag gac aag gag gaa ctg      3091
Val Glu Ser Met Phe Arg Glu Ser Gly Phe Gln Asp Lys Glu Glu Leu
900                 905                 910                 915 aca tgg gaa gat ttt cac ttc atg ctg cgg gac cac aat agc gag ctc      3139
Thr Trp Glu Asp Phe His Phe Met Leu Arg Asp His Asn Ser Glu Leu
                920                 925                 930 cgc ttc acg cag ctc tgt gtc aaa ggg gtg gag gtg cct gaa gtc atc      3187
Arg Phe Thr Gln Leu Cys Val Lys Gly Val Glu Val Pro Glu Val Ile
                    935                 940                 945 aag gac ctc tgc cgg cga gcc tcc tac atc agc cag gat atg atc tgt      3235
Lys Asp Leu Cys Arg Arg Ala Ser Tyr Ile Ser Gln Asp Met Ile Cys
        950                 955                 960 ccc tct ccc aga gtg agt gcc cgc tgt tcc cgc agc gac att gag act      3283
```

-continued

| | | | | | | | | | | | | | | | |
|---|---|---|---|---|---|---|---|---|---|---|---|---|---|---|---|
|Pro|Ser|Pro|Arg|Val|Ser|Ala|Arg|Cys|Ser|Arg|Ser|Asp|Ile|Glu|Thr|
| |965| | | |970| | | |975| | | | | | |

| gag | ttg | aca | cct | cag | aga | ctg | cag | tgc | ccc | atg | gac | aca | gac | cct | ccc | 3331 |
|---|---|---|---|---|---|---|---|---|---|---|---|---|---|---|---|---|
| Glu | Leu | Thr | Pro | Gln | Arg | Leu | Gln | Cys | Pro | Met | Asp | Thr | Asp | Pro | Pro | |
| 980 | | | | 985 | | | | | 990 | | | | | 995 | | |

| cag | gag | att | cgg | cgg | agg | ttt | ggc | aag | aag | gta | acg | tca | ttc | cag | 3376 |
|---|---|---|---|---|---|---|---|---|---|---|---|---|---|---|---|
| Gln | Glu | Ile | Arg | Arg | Arg | Phe | Gly | Lys | Lys | Val | Thr | Ser | Phe | Gln | |
| | | 1000 | | | | | 1005 | | | | | 1010 | | | |

| ccc | ttg | ctg | ttc | act | gag | gcg | cac | cga | gag | aag | ttc | caa | cgc | agc | 3421 |
|---|---|---|---|---|---|---|---|---|---|---|---|---|---|---|---|
| Pro | Leu | Leu | Phe | Thr | Glu | Ala | His | Arg | Glu | Lys | Phe | Gln | Arg | Ser | |
| | | | | 1015 | | | | 1020 | | | | | 1025 | | |

| tgt | ctc | cac | cag | acg | gtg | caa | cag | ttc | aag | cgc | ttc | att | gag | aac | 3466 |
|---|---|---|---|---|---|---|---|---|---|---|---|---|---|---|---|
| Cys | Leu | His | Gln | Thr | Val | Gln | Gln | Phe | Lys | Arg | Phe | Ile | Glu | Asn | |
| | | | 1030 | | | | | 1035 | | | | | 1040 | | |

| tac | cgg | cgc | cac | atc | ggc | tgc | gtg | gcc | gtg | ttc | tac | gcc | atc | gct | 3511 |
|---|---|---|---|---|---|---|---|---|---|---|---|---|---|---|---|
| Tyr | Arg | Arg | His | Ile | Gly | Cys | Val | Ala | Val | Phe | Tyr | Ala | Ile | Ala | |
| | | | | 1045 | | | | 1050 | | | | | 1055 | | |

| ggg | ggg | ctt | ttc | ctg | gag | agg | gcc | tac | tac | tac | gcc | ttt | gcc | gca | 3556 |
|---|---|---|---|---|---|---|---|---|---|---|---|---|---|---|---|
| Gly | Gly | Leu | Phe | Leu | Glu | Arg | Ala | Tyr | Tyr | Tyr | Ala | Phe | Ala | Ala | |
| | | | | 1060 | | | | 1065 | | | | | 1070 | | |

| cat | cac | acg | ggc | atc | aca | gac | acc | acc | cgc | gtg | gga | atc | atc | ctg | 3601 |
|---|---|---|---|---|---|---|---|---|---|---|---|---|---|---|---|
| His | His | Thr | Gly | Ile | Thr | Asp | Thr | Thr | Arg | Val | Gly | Ile | Ile | Leu | |
| | | | | 1075 | | | | 1080 | | | | | 1085 | | |

| tcg | cgg | ggc | aca | gca | gcc | agc | atc | tct | ttc | atg | ttc | tcc | tac | atc | 3646 |
|---|---|---|---|---|---|---|---|---|---|---|---|---|---|---|---|
| Ser | Arg | Gly | Thr | Ala | Ala | Ser | Ile | Ser | Phe | Met | Phe | Ser | Tyr | Ile | |
| | | | | 1090 | | | | 1095 | | | | | 1100 | | |

| ttg | ctc | acc | atg | tgc | cgc | aac | ctc | atc | acc | ttc | ctg | cga | gaa | acc | 3691 |
|---|---|---|---|---|---|---|---|---|---|---|---|---|---|---|---|
| Leu | Leu | Thr | Met | Cys | Arg | Asn | Leu | Ile | Thr | Phe | Leu | Arg | Glu | Thr | |
| | | | | 1105 | | | | 1110 | | | | | 1115 | | |

| ttc | ctc | aac | cgc | tac | gtg | ccc | ttc | gac | gcc | gcc | gtg | gac | ttc | cat | 3736 |
|---|---|---|---|---|---|---|---|---|---|---|---|---|---|---|---|
| Phe | Leu | Asn | Arg | Tyr | Val | Pro | Phe | Asp | Ala | Ala | Val | Asp | Phe | His | |
| | | | | 1120 | | | | 1125 | | | | | 1130 | | |

| cgc | ctc | att | gcc | tcc | acc | gcc | atc | gtc | ctc | aca | gtc | tta | cac | agt | 3781 |
|---|---|---|---|---|---|---|---|---|---|---|---|---|---|---|---|
| Arg | Leu | Ile | Ala | Ser | Thr | Ala | Ile | Val | Leu | Thr | Val | Leu | His | Ser | |
| | | | | 1135 | | | | 1140 | | | | | 1145 | | |

| gtg | ggc | cat | gtg | gtg | aat | gtg | tac | ctg | ttc | tcc | atc | agc | ccc | ctc | 3826 |
|---|---|---|---|---|---|---|---|---|---|---|---|---|---|---|---|
| Val | Gly | His | Val | Val | Asn | Val | Tyr | Leu | Phe | Ser | Ile | Ser | Pro | Leu | |
| | | | | 1150 | | | | 1155 | | | | | 1160 | | |

| agc | gtc | ctc | tct | tgc | ctc | ttt | cct | ggc | ctc | ttc | cat | gat | gat | ggg | 3871 |
|---|---|---|---|---|---|---|---|---|---|---|---|---|---|---|---|
| Ser | Val | Leu | Ser | Cys | Leu | Phe | Pro | Gly | Leu | Phe | His | Asp | Asp | Gly | |
| | | | | 1165 | | | | 1170 | | | | | 1175 | | |

| tct | gag | ctc | ccc | cag | aag | tat | tac | tgg | tgg | ttc | ttc | cag | acc | gta | 3916 |
|---|---|---|---|---|---|---|---|---|---|---|---|---|---|---|---|
| Ser | Glu | Leu | Pro | Gln | Lys | Tyr | Tyr | Trp | Trp | Phe | Phe | Gln | Thr | Val | |
| | | | | 1180 | | | | 1185 | | | | | 1190 | | |

| cca | ggc | ctc | acg | ggg | gtt | gtg | ctg | ctc | ctg | atc | ctg | gcc | atc | atg | 3961 |
|---|---|---|---|---|---|---|---|---|---|---|---|---|---|---|---|
| Pro | Gly | Leu | Thr | Gly | Val | Val | Leu | Leu | Leu | Ile | Leu | Ala | Ile | Met | |
| | | | | 1195 | | | | 1200 | | | | | 1205 | | |

| tat | gtc | ttt | gcc | tcc | cac | cac | ttc | cgc | cgc | cgc | agt | ttc | cgg | ggc | 4006 |
|---|---|---|---|---|---|---|---|---|---|---|---|---|---|---|---|
| Tyr | Val | Phe | Ala | Ser | His | His | Phe | Arg | Arg | Arg | Ser | Phe | Arg | Gly | |
| | | | | 1210 | | | | 1215 | | | | | 1220 | | |

| ttc | tgg | ctg | acc | cac | cac | ctc | tac | atc | ctg | ctc | tat | gtc | ctg | ctc | 4051 |
|---|---|---|---|---|---|---|---|---|---|---|---|---|---|---|---|
| Phe | Trp | Leu | Thr | His | His | Leu | Tyr | Ile | Leu | Leu | Tyr | Val | Leu | Leu | |
| | | | | 1225 | | | | 1230 | | | | | 1235 | | |

| atc | atc | cat | ggt | agc | ttt | gcc | ctg | atc | cag | ctg | ccc | cgt | ttc | cac | 4096 |
|---|---|---|---|---|---|---|---|---|---|---|---|---|---|---|---|
| Ile | Ile | His | Gly | Ser | Phe | Ala | Leu | Ile | Gln | Leu | Pro | Arg | Phe | His | |
| | | | | 1240 | | | | 1245 | | | | | 1250 | | |

| atc | ttc | ttc | ctg | gtc | cca | gca | atc | atc | tat | ggg | ggc | gac | aag | ctg | 4141 |
|---|---|---|---|---|---|---|---|---|---|---|---|---|---|---|---|
| Ile | Phe | Phe | Leu | Val | Pro | Ala | Ile | Ile | Tyr | Gly | Gly | Asp | Lys | Leu | |
| | | | | 1255 | | | | 1260 | | | | | 1265 | | |

```
gtg agc ctg agc cgg aag aag gtg gag atc agc gtg gtg aag gcg         4186
Val Ser Leu Ser Arg Lys Lys Val Glu Ile Ser Val Val Lys Ala
            1270                1275                1280 gag ctg ctg ccc tca gga gtg acc cac ctg cgg ttc cag cgg ccc         4231
Glu Leu Leu Pro Ser Gly Val Thr His Leu Arg Phe Gln Arg Pro
        1285                1290                1295 cag ggc ttt gag tac aag tca ggg cag tgg gtg cgg atc gct tgc         4276
Gln Gly Phe Glu Tyr Lys Ser Gly Gln Trp Val Arg Ile Ala Cys
        1300                1305                1310 ctg gct ctg ggg acc acc gag tac cac ccc ttc aca ctg acc tct         4321
Leu Ala Leu Gly Thr Thr Glu Tyr His Pro Phe Thr Leu Thr Ser
        1315                1320                1325 gcg ccc cat gag gac acg ctt agc ctg cac atc cgg gca gca ggg         4366
Ala Pro His Glu Asp Thr Leu Ser Leu His Ile Arg Ala Ala Gly
        1330                1335                1340 ccc tgg acc act cgc ctc agg gag atc tac tca gcc ccg acg ggt         4411
Pro Trp Thr Thr Arg Leu Arg Glu Ile Tyr Ser Ala Pro Thr Gly
        1345                1350                1355 gac aga tgt gcc aga tac cca aag ctg tac ctt gat gga cca ttt         4456
Asp Arg Cys Ala Arg Tyr Pro Lys Leu Tyr Leu Asp Gly Pro Phe
        1360                1365                1370 gga gag ggc cac cag gag tgg cat aag ttt gag gtg tca gtg tta         4501
Gly Glu Gly His Gln Glu Trp His Lys Phe Glu Val Ser Val Leu
        1375                1380                1385 gtg gga ggg ggc att ggg gtc acc cct ttt gcc tcc atc ctc aaa         4546
Val Gly Gly Gly Ile Gly Val Thr Pro Phe Ala Ser Ile Leu Lys
        1390                1395                1400 gac ctg gtc ttc aag tca tcc gtc agc tgc caa gtg ttc tgt aag         4591
Asp Leu Val Phe Lys Ser Ser Val Ser Cys Gln Val Phe Cys Lys
        1405                1410                1415 aag atc tac ttc atc tgg gtg acg cgg acc cag cgt cag ttt gag         4636
Lys Ile Tyr Phe Ile Trp Val Thr Arg Thr Gln Arg Gln Phe Glu
        1420                1425                1430 tgg ctg gct gac atc atc cga gag gtg gag gag aat gac cac cag         4681
Trp Leu Ala Asp Ile Ile Arg Glu Val Glu Glu Asn Asp His Gln
        1435                1440                1445 gac ctg gtg tct gtg cac atc tac atc acc cag ctg gct gag aag         4726
Asp Leu Val Ser Val His Ile Tyr Ile Thr Gln Leu Ala Glu Lys
        1450                1455                1460 ttc gac ctc agg acc act atg ctg tac atc tgt gag cgg cac ttc         4771
Phe Asp Leu Arg Thr Thr Met Leu Tyr Ile Cys Glu Arg His Phe
        1465                1470                1475 cag aag gtt ctg aac cgg agt cta ttc aca ggc ctg cgc tcc atc         4816
Gln Lys Val Leu Asn Arg Ser Leu Phe Thr Gly Leu Arg Ser Ile
        1480                1485                1490 acc cac ttt ggc cgt ccc ccc ttt gag ccc ttc ttc aac tcc ctg         4861
Thr His Phe Gly Arg Pro Pro Phe Glu Pro Phe Phe Asn Ser Leu
        1495                1500                1505 cag gag gtc cac ccc cag gtc cgg aag atc ggg gtg ttt agc tgt         4906
Gln Glu Val His Pro Gln Val Arg Lys Ile Gly Val Phe Ser Cys
        1510                1515                1520 ggc ccc cct ggc atg acc aag aat gtg gaa aag gcc tgt cag ctc         4951
Gly Pro Pro Gly Met Thr Lys Asn Val Glu Lys Ala Cys Gln Leu
        1525                1530                1535 atc aac agg cag gac cgg act cac ttc tcc cac cat tat gag aac         4996
Ile Asn Arg Gln Asp Arg Thr His Phe Ser His His Tyr Glu Asn
        1540                1545                1550 ttc tag gccctgccc gggggttctg cccactgccc agttgagcag aggtttgagc       5052
Phe
```

| | | | | |
|---|---|---|---|---|
| ccacacctca | cctctgttct | tcctatttct | ggctgcctca | gccttctctg atttcccacc | 5112 |
| tcccaacctt | gttccaggtg | gccatagtca | gtcaccatgt | gtgggctcag ggaccccag | 5172 |
| gaccaggatg | tgtctcagcc | tggagaaatg | gtgggggggc | agtgtctagg gactagagtg | 5232 |
| agaagtaggg | gagctactga | tttggggcaa | agtgaaacct | ctgcttccag acttcagaaa | 5292 |
| caaatctcag | aagacaagct | gacctgacaa | gtactatgtg | tgtgcatgtc tgtatgtgtg | 5352 |
| ttggggcggt | gagtgtaagg | atgcagtggg | agcatggatg | ctggcatctt agaaccctcc | 5412 |
| ctactcccat | acctcctcct | cttctgggct | ccccactgtc | agacgggctg gcaaatgcct | 5472 |
| tgcaggaggt | agaggctgga | cccatggcaa | gccatttaca | gaaacccact cggcacccca | 5532 |
| gtctaacacc | acaactaatt | tcacccaagg | ttttaagcac | gttctttcat cagaccctgg | 5592 |
| cccaatacct | atgtatgcaa | tgctcctcag | ccctcttctc | cctgctccag tagtctccct | 5652 |
| tccaaataaa | tcacttttct | gccttaaaaa | aaaaaaaaa | a | 5693 |

<210> SEQ ID NO 12
<211> LENGTH: 1551
<212> TYPE: PRT
<213> ORGANISM: Homo sapiens

<400> SEQUENCE: 12

```
Met Gly Phe Cys Leu Ala Leu Ala Trp Thr Leu Leu Val Gly Ala Trp
1               5                   10                  15

Thr Pro Leu Gly Ala Gln Asn Pro Ile Ser Trp Glu Val Gln Arg Phe
            20                  25                  30

Asp Gly Trp Tyr Asn Asn Leu Met Glu His Arg Trp Gly Ser Lys Gly
        35                  40                  45

Ser Arg Leu Gln Arg Leu Val Pro Ala Ser Tyr Ala Asp Gly Val Tyr
    50                  55                  60

Gln Pro Leu Gly Glu Pro His Leu Pro Asn Pro Arg Asp Leu Ser Asn
65                  70                  75                  80

Thr Ile Ser Arg Gly Pro Ala Gly Leu Ala Ser Leu Arg Asn Arg Thr
                85                  90                  95

Val Leu Gly Val Phe Phe Gly Tyr His Val Leu Ser Asp Leu Val Ser
            100                 105                 110

Val Glu Thr Pro Gly Cys Pro Ala Glu Phe Leu Asn Ile Arg Ile Pro
        115                 120                 125

Pro Gly Asp Pro Met Phe Asp Pro Asp Gln Arg Gly Asp Val Val Leu
    130                 135                 140

Pro Phe Gln Arg Ser Arg Trp Asp Pro Glu Thr Gly Arg Ser Pro Ser
145                 150                 155                 160

Asn Pro Arg Asp Pro Ala Asn Gln Val Thr Gly Trp Leu Asp Gly Ser
                165                 170                 175

Ala Ile Tyr Gly Ser Ser His Ser Trp Ser Asp Ala Leu Arg Ser Phe
            180                 185                 190

Ser Arg Gly Gln Leu Ala Ser Gly Pro Asp Pro Ala Phe Pro Arg Asp
        195                 200                 205

Ser Gln Asn Pro Leu Leu Met Trp Ala Ala Pro Asp Pro Ala Thr Gly
    210                 215                 220

Gln Asn Gly Pro Arg Gly Leu Tyr Ala Phe Gly Ala Glu Arg Gly Asn
225                 230                 235                 240

Arg Glu Pro Phe Leu Gln Ala Leu Gly Leu Leu Trp Phe Arg Tyr His
                245                 250                 255

Asn Leu Trp Ala Gln Arg Leu Ala Arg Gln His Pro Asp Trp Glu Asp
```

-continued

```
                260                 265                 270
Glu Glu Leu Phe Gln His Ala Arg Lys Arg Val Ile Ala Thr Tyr Gln
            275                 280                 285
Asn Ile Ala Val Tyr Glu Trp Leu Pro Ser Phe Leu Gln Lys Thr Leu
        290                 295                 300
Pro Glu Tyr Thr Gly Tyr Arg Pro Phe Leu Asp Pro Ser Ile Ser Ser
305                 310                 315                 320
Glu Phe Val Ala Ala Ser Glu Gln Phe Leu Ser Thr Met Val Pro Pro
                325                 330                 335
Gly Val Tyr Met Arg Asn Ala Ser Cys His Phe Gln Gly Val Ile Asn
            340                 345                 350
Arg Asn Ser Ser Val Ser Arg Ala Leu Arg Val Cys Asn Ser Tyr Trp
        355                 360                 365
Ser Arg Glu His Pro Ser Leu Gln Ser Ala Glu Asp Val Asp Ala Leu
    370                 375                 380
Leu Leu Gly Met Ala Ser Gln Ile Ala Glu Arg Glu Asp His Val Leu
385                 390                 395                 400
Val Glu Asp Val Arg Asp Phe Trp Pro Gly Pro Leu Lys Phe Ser Arg
                405                 410                 415
Thr Asp His Leu Ala Ser Cys Leu Gln Arg Gly Arg Asp Leu Gly Leu
            420                 425                 430
Pro Ser Tyr Thr Lys Ala Arg Ala Leu Gly Leu Ser Pro Ile Thr
        435                 440                 445
Arg Trp Gln Asp Ile Asn Pro Ala Leu Ser Arg Ser Asn Asp Thr Val
    450                 455                 460
Leu Glu Ala Thr Ala Ala Leu Tyr Asn Gln Asp Leu Ser Trp Leu Glu
465                 470                 475                 480
Leu Leu Pro Gly Gly Leu Leu Glu Ser His Arg Asp Pro Gly Pro Leu
                485                 490                 495
Phe Ser Thr Ile Val Leu Glu Gln Phe Val Arg Leu Arg Asp Gly Asp
            500                 505                 510
Arg Tyr Trp Phe Glu Asn Thr Arg Asn Gly Leu Phe Ser Lys Lys Glu
        515                 520                 525
Ile Glu Glu Ile Arg Asn Thr Thr Leu Gln Asp Val Leu Val Ala Val
    530                 535                 540
Ile Asn Ile Asp Pro Ser Ala Leu Gln Pro Asn Val Phe Val Trp His
545                 550                 555                 560
Lys Gly Asp Pro Cys Pro Gln Pro Arg Gln Leu Ser Thr Glu Gly Leu
                565                 570                 575
Pro Ala Cys Ala Pro Ser Val Val Arg Asp Tyr Phe Glu Gly Ser Gly
            580                 585                 590
Phe Gly Phe Gly Val Thr Ile Gly Thr Leu Cys Cys Phe Pro Leu Val
        595                 600                 605
Ser Leu Leu Ser Ala Trp Ile Val Ala Arg Leu Arg Met Arg Asn Phe
    610                 615                 620
Lys Arg Leu Gln Gly Gln Asp Arg Gln Ser Ile Val Ser Glu Lys Leu
625                 630                 635                 640
Val Gly Gly Met Glu Ala Leu Glu Trp Gln Gly His Lys Glu Pro Cys
                645                 650                 655
Arg Pro Val Leu Val Tyr Leu Gln Pro Gly Gln Ile Arg Val Val Asp
            660                 665                 670
Gly Arg Leu Thr Val Leu Arg Thr Ile Gln Leu Gln Pro Pro Gln Lys
        675                 680                 685
```

-continued

```
Val Asn Phe Val Leu Ser Ser Asn Arg Gly Arg Thr Leu Leu Leu
    690                 695                 700
Lys Ile Pro Lys Glu Tyr Asp Leu Val Leu Phe Asn Leu Glu Glu
705                 710                 715                 720
Glu Arg Gln Ala Leu Val Glu Asn Leu Arg Gly Ala Leu Lys Glu Ser
                    725                 730                 735
Gly Leu Ser Ile Gln Glu Trp Glu Leu Arg Gln Glu Leu Met Arg
                740                 745                 750
Ala Ala Val Thr Arg Glu Gln Arg His Leu Leu Glu Thr Phe Phe
            755                 760                 765
Arg His Leu Phe Ser Gln Val Leu Asp Ile Asn Gln Ala Asp Ala Gly
        770                 775                 780
Thr Leu Pro Leu Asp Ser Gln Lys Val Arg Glu Ala Leu Thr Cys
785                 790                 795                 800
Glu Leu Ser Arg Ala Glu Phe Ala Glu Ser Leu Gly Leu Lys Pro Gln
                805                 810                 815
Asp Met Phe Val Glu Ser Met Phe Ser Leu Ala Asp Lys Asp Gly Asn
            820                 825                 830
Gly Tyr Leu Ser Phe Arg Glu Phe Leu Asp Ile Leu Val Val Phe Met
        835                 840                 845
Lys Gly Ser Pro Glu Glu Lys Ser Arg Leu Met Phe Arg Met Tyr Asp
850                 855                 860
Phe Asp Gly Asn Gly Leu Ile Ser Lys Asp Glu Phe Ile Arg Met Leu
865                 870                 875                 880
Arg Ser Phe Ile Glu Ile Ser Asn Asn Cys Leu Ser Lys Ala Gln Leu
                885                 890                 895
Ala Glu Val Val Glu Ser Met Phe Arg Glu Ser Gly Phe Gln Asp Lys
            900                 905                 910
Glu Glu Leu Thr Trp Glu Asp Phe His Phe Met Leu Arg Asp His Asn
        915                 920                 925
Ser Glu Leu Arg Phe Thr Gln Leu Cys Val Lys Gly Val Glu Val Pro
930                 935                 940
Glu Val Ile Lys Asp Leu Cys Arg Arg Ala Ser Tyr Ile Ser Gln Asp
945                 950                 955                 960
Met Ile Cys Pro Ser Pro Arg Val Ser Ala Arg Cys Ser Arg Ser Asp
                965                 970                 975
Ile Glu Thr Glu Leu Thr Pro Gln Arg Leu Gln Cys Pro Met Asp Thr
            980                 985                 990
Asp Pro Pro Gln Glu Ile Arg Arg  Arg Phe Gly Lys Lys  Val Thr Ser
        995                 1000                1005
Phe Gln  Pro Leu Leu Phe Thr  Glu Ala His Arg Glu  Lys Phe Gln
    1010                1015                1020
Arg Ser  Cys Leu His Gln Thr  Val Gln Gln Phe Lys  Arg Phe Ile
    1025                1030                1035
Glu Asn  Tyr Arg Arg His Ile  Gly Cys Val Ala Val  Phe Tyr Ala
    1040                1045                1050
Ile Ala  Gly Gly Leu Phe Leu  Glu Arg Ala Tyr Tyr  Tyr Ala Phe
    1055                1060                1065
Ala Ala  His His Thr Gly Ile  Thr Asp Thr Thr Arg  Val Gly Ile
    1070                1075                1080
Ile Leu  Ser Arg Gly Thr Ala  Ala Ser Ile Ser Phe  Met Phe Ser
    1085                1090                1095
```

-continued

| | | | | | | | | | | |
|---|---|---|---|---|---|---|---|---|---|---|
|Tyr|Ile|Leu|Leu|Thr|Met|Cys|Arg|Asn|Leu|Ile|Thr|Phe|Leu|Arg|
| |1100| | | |1105| | | |1110| | | | | |

Tyr Ile Leu Leu Thr Met Cys Arg Asn Leu Ile Thr Phe Leu Arg
    1100            1105            1110

Glu Thr Phe Leu Asn Arg Tyr Val Pro Phe Asp Ala Ala Val Asp
    1115            1120            1125

Phe His Arg Leu Ile Ala Ser Thr Ala Ile Val Leu Thr Val Leu
    1130            1135            1140

His Ser Val Gly His Val Val Asn Val Tyr Leu Phe Ser Ile Ser
    1145            1150            1155

Pro Leu Ser Val Leu Ser Cys Leu Phe Pro Gly Leu Phe His Asp
    1160            1165            1170

Asp Gly Ser Glu Leu Pro Gln Lys Tyr Tyr Trp Trp Phe Phe Gln
    1175            1180            1185

Thr Val Pro Gly Leu Thr Gly Val Val Leu Leu Ile Leu Ala
    1190            1195            1200

Ile Met Tyr Val Phe Ala Ser His His Phe Arg Arg Arg Ser Phe
    1205            1210            1215

Arg Gly Phe Trp Leu Thr His His Leu Tyr Ile Leu Leu Tyr Val
    1220            1225            1230

Leu Leu Ile Ile His Gly Ser Phe Ala Leu Ile Gln Leu Pro Arg
    1235            1240            1245

Phe His Ile Phe Phe Leu Val Pro Ala Ile Ile Tyr Gly Gly Asp
    1250            1255            1260

Lys Leu Val Ser Leu Ser Arg Lys Lys Val Glu Ile Ser Val Val
    1265            1270            1275

Lys Ala Glu Leu Leu Pro Ser Gly Val Thr His Leu Arg Phe Gln
    1280            1285            1290

Arg Pro Gln Gly Phe Glu Tyr Lys Ser Gly Gln Trp Val Arg Ile
    1295            1300            1305

Ala Cys Leu Ala Leu Gly Thr Thr Glu Tyr His Pro Phe Thr Leu
    1310            1315            1320

Thr Ser Ala Pro His Glu Asp Thr Leu Ser Leu His Ile Arg Ala
    1325            1330            1335

Ala Gly Pro Trp Thr Thr Arg Leu Arg Glu Ile Tyr Ser Ala Pro
    1340            1345            1350

Thr Gly Asp Arg Cys Ala Arg Tyr Pro Lys Leu Tyr Leu Asp Gly
    1355            1360            1365

Pro Phe Gly Glu Gly His Gln Glu Trp His Lys Phe Glu Val Ser
    1370            1375            1380

Val Leu Val Gly Gly Gly Ile Gly Val Thr Pro Phe Ala Ser Ile
    1385            1390            1395

Leu Lys Asp Leu Val Phe Lys Ser Ser Val Ser Cys Gln Val Phe
    1400            1405            1410

Cys Lys Lys Ile Tyr Phe Ile Trp Val Thr Arg Thr Gln Arg Gln
    1415            1420            1425

Phe Glu Trp Leu Ala Asp Ile Ile Arg Glu Val Glu Glu Asn Asp
    1430            1435            1440

His Gln Asp Leu Val Ser Val His Ile Tyr Ile Thr Gln Leu Ala
    1445            1450            1455

Glu Lys Phe Asp Leu Arg Thr Thr Met Leu Tyr Ile Cys Glu Arg
    1460            1465            1470

His Phe Gln Lys Val Leu Asn Arg Ser Leu Phe Thr Gly Leu Arg
    1475            1480            1485

Ser Ile Thr His Phe Gly Arg Pro Pro Phe Glu Pro Phe Phe Asn

```
                1490            1495            1500
   Ser Leu Gln Glu Val His Pro Gln Val Arg Lys Ile Gly Val Phe
       1505                1510                1515

Ser Cys Gly Pro Pro Gly Met Thr Lys Asn Val Glu Lys Ala Cys
       1520                1525                1530

Gln Leu Ile Asn Arg Gln Asp Arg Thr His Phe Ser His His Tyr
       1535                1540                1545

Glu Asn Phe
       1550

<210> SEQ ID NO 13
<211> LENGTH: 6376
<212> TYPE: DNA
<213> ORGANISM: Homo sapiens
<220> FEATURE:
<221> NAME/KEY: CDS
<222> LOCATION: (204)..(4850)

<400> SEQUENCE: 13
ggtctgtcct gagccgacac ctgcacagtg gcgagaccaa ggacccagag agaaaggtga       60
gagtgcagcc ggggaggctg aggatcggcg gagctggaag agtgagggtg aaggcaagaa      120
gtagagcaca gaagcaaaga ttttaagagg aaagaagaca tctgaaccca acaccaccct      180
aaaccacagg ctgcaggtt ggc atg ctc cgt gca aga cca gag gca ctg atg       233
                       Met Leu Arg Ala Arg Pro Glu Ala Leu Met
                         1               5                  10 ctc ctg gga gct ctt ctg act gga tcc ctg ggt cca tcg ggc agt cag        281
Leu Leu Gly Ala Leu Leu Thr Gly Ser Leu Gly Pro Ser Gly Ser Gln
             15                  20                  25 gac gca ctc tca ctg ccc tgg gaa gtg cag cgc tat gac ggc tgg ttt        329
Asp Ala Leu Ser Leu Pro Trp Glu Val Gln Arg Tyr Asp Gly Trp Phe
         30                  35                  40 aac aac ctg agg cac cac gag cgt ggt gct gtt ggc tgc cgg ttg cag        377
Asn Asn Leu Arg His His Glu Arg Gly Ala Val Gly Cys Arg Leu Gln
     45                  50                  55 cgc cgc gta cca gcc aat tac gcc gac ggt gtg tat cag gct ctg gag        425
Arg Arg Val Pro Ala Asn Tyr Ala Asp Gly Val Tyr Gln Ala Leu Glu
 60                  65                  70 gag ccg cag ctg ccc aac ccg cgc cgg ctc agc aac gca gcc acg cgg        473
Glu Pro Gln Leu Pro Asn Pro Arg Arg Leu Ser Asn Ala Ala Thr Arg
75                  80                  85                  90 ggc ata gcc ggc ctg ccg tcg ctc cac aac cgc acc gta ctg ggg gtc        521
Gly Ile Ala Gly Leu Pro Ser Leu His Asn Arg Thr Val Leu Gly Val
                 95                 100                 105 ttc ttt ggc tac cat gtt ctt tcc gac gtg gtg agc gtg gaa acg ccc        569
Phe Phe Gly Tyr His Val Leu Ser Asp Val Val Ser Val Glu Thr Pro
            110                 115                 120 ggt tgc ccc gcc gag ttc ctc aac atc cgc atc cca cct gga gac ccc        617
Gly Cys Pro Ala Glu Phe Leu Asn Ile Arg Ile Pro Pro Gly Asp Pro
        125                 130                 135 gtg ttc gac ccc gac cag cgc ggg gac gtg gtg ctg ccc ttc cag agg        665
Val Phe Asp Pro Asp Gln Arg Gly Asp Val Val Leu Pro Phe Gln Arg
    140                 145                 150 agc cgc tgg gac ccc gag acc gga cgg agt ccc agc aac ccc cgg gac        713
Ser Arg Trp Asp Pro Glu Thr Gly Arg Ser Pro Ser Asn Pro Arg Asp
155                 160                 165                 170 ctg gcc aac cag gtg acg ggc tgg ctg gac ggc agc gcc atc tat ggc        761
Leu Ala Asn Gln Val Thr Gly Trp Leu Asp Gly Ser Ala Ile Tyr Gly
                175                 180                 185
```

-continued

| | |
|---|---|
| tcc tcg cac tcc tgg agc gac gcg ctg cgg agc ttc tcg ggg gga cag<br>Ser Ser His Ser Trp Ser Asp Ala Leu Arg Ser Phe Ser Gly Gly Gln<br>190                       195                    200 | 809 |
| ctg gcg tcg ggg ccc gac ccc gct ttc ccc cga gac tcg cag aac ccc<br>Leu Ala Ser Gly Pro Asp Pro Ala Phe Pro Arg Asp Ser Gln Asn Pro<br>205                       210                    215 | 857 |
| ctg ctc atg tgg gcg gcg ccc gac ccc gcc acc ggg cag aac ggg ccc<br>Leu Leu Met Trp Ala Ala Pro Asp Pro Ala Thr Gly Gln Asn Gly Pro<br>220                       225                    230 | 905 |
| cgg ggg ctg tac gcc ttc ggg gca gag aga ggg aac cgg gaa ccc ttc<br>Arg Gly Leu Tyr Ala Phe Gly Ala Glu Arg Gly Asn Arg Glu Pro Phe<br>235                  240                   245                  250 | 953 |
| ctg cag gcg ctg ggc ctg ctc tgg ttc cgc tac cac aac ctg tgg gcg<br>Leu Gln Ala Leu Gly Leu Leu Trp Phe Arg Tyr His Asn Leu Trp Ala<br>                  255                    260                   265 | 1001 |
| cag agg ctg gcc cgc cag cac cca gac tgg gag gac gag gag ctg ttc<br>Gln Arg Leu Ala Arg Gln His Pro Asp Trp Glu Asp Glu Glu Leu Phe<br>                  270                    275                  280 | 1049 |
| cag cac gca cgc aag agg gtc atc gcc acc tac cag aac atc gct gtg<br>Gln His Ala Arg Lys Arg Val Ile Ala Thr Tyr Gln Asn Ile Ala Val<br>                  285                    290                  295 | 1097 |
| tat gag tgg ctg ccc agc ttc ctg cag aaa aca ctc ccg gag tat aca<br>Tyr Glu Trp Leu Pro Ser Phe Leu Gln Lys Thr Leu Pro Glu Tyr Thr<br>300                       305                    310 | 1145 |
| gga tac cgt cct ttc cta gac ccc agc atc tcc ccg gaa ttt gtg gtg<br>Gly Tyr Arg Pro Phe Leu Asp Pro Ser Ile Ser Pro Glu Phe Val Val<br>315                       320                    325                  330 | 1193 |
| gcc tct gag cag ttc ttc tct acc atg gtg ccc cct ggt gtc tac atg<br>Ala Ser Glu Gln Phe Phe Ser Thr Met Val Pro Pro Gly Val Tyr Met<br>                  335                    340                  345 | 1241 |
| aga aat gcc agc tgt cat ttc cgg aag gtc ctg aac aag ggt ttt caa<br>Arg Asn Ala Ser Cys His Phe Arg Lys Val Leu Asn Lys Gly Phe Gln<br>                  350                    355                  360 | 1289 |
| agc tcc caa gct ctc agg gtc tgc aac aac tac tgg att cgg gag aac<br>Ser Ser Gln Ala Leu Arg Val Cys Asn Asn Tyr Trp Ile Arg Glu Asn<br>                  365                    370                  375 | 1337 |
| ccc aat ctg aac agt acc cag gag gtg aat gag ctg ctg ctg gga atg<br>Pro Asn Leu Asn Ser Thr Gln Glu Val Asn Glu Leu Leu Leu Gly Met<br>380                       385                    390 | 1385 |
| gcc tcc cag att tcg gag ttg gag gac aac ata gtg gtt gaa gat ctg<br>Ala Ser Gln Ile Ser Glu Leu Glu Asp Asn Ile Val Val Glu Asp Leu<br>395                       400                    405                  410 | 1433 |
| agg gat tac tgg cct ggc cct ggc aaa ttc tcc cgt aca gac tat gtg<br>Arg Asp Tyr Trp Pro Gly Pro Gly Lys Phe Ser Arg Thr Asp Tyr Val<br>                  415                    420                  425 | 1481 |
| gcc agc agc atc caa cgt ggc cga gat atg ggg ctg ccc agc tat agc<br>Ala Ser Ser Ile Gln Arg Gly Arg Asp Met Gly Leu Pro Ser Tyr Ser<br>                  430                    435                  440 | 1529 |
| cag gcc ctg ctg gcc ttt ggg ctg gac atc cca agg aac tgg agt gat<br>Gln Ala Leu Leu Ala Phe Gly Leu Asp Ile Pro Arg Asn Trp Ser Asp<br>                  445                    450                  455 | 1577 |
| ctc aac cct aat gtg gac ccc cag gtg ctg gag gcc aca gct gcc ctg<br>Leu Asn Pro Asn Val Asp Pro Gln Val Leu Glu Ala Thr Ala Ala Leu<br>460                       465                    470 | 1625 |
| tac aac cag gac cta tcc cag cta gag ctg ctc ctt ggg ggc ctc ctg<br>Tyr Asn Gln Asp Leu Ser Gln Leu Glu Leu Leu Leu Gly Gly Leu Leu<br>475                       480                    485                  490 | 1673 |
| gag agc cat ggg gac cct gga ccc ctg ttc agt gcc att gtc ctc gac<br>Glu Ser His Gly Asp Pro Gly Pro Leu Phe Ser Ala Ile Val Leu Asp<br>                  495                    500                  505 | 1721 |

-continued

| | |
|---|---|
| cag ttt gta cgg ctg cgg gat ggt gac cgc tac tgg ttt gag aac acc<br>Gln Phe Val Arg Leu Arg Asp Gly Asp Arg Tyr Trp Phe Glu Asn Thr<br>510                            515                     520 | 1769 |
| agg aat ggg ctg ttc tcc aag aag gag att gaa gac atc cga aat acc<br>Arg Asn Gly Leu Phe Ser Lys Lys Glu Ile Glu Asp Ile Arg Asn Thr<br>525                          530                     535 | 1817 |
| acc ctg cgg gac gtg ctg gtc gct gtt atc aac att gac ccc agt gcc<br>Thr Leu Arg Asp Val Leu Val Ala Val Ile Asn Ile Asp Pro Ser Ala<br>540                          545                     550 | 1865 |
| ctg cag ccc aat gtc ttt gtc tgg cat aaa ggt gca ccc tgc cct caa<br>Leu Gln Pro Asn Val Phe Val Trp His Lys Gly Ala Pro Cys Pro Gln<br>555                   560                     565                     570 | 1913 |
| cct aag cag ctc aca act gac ggc ctg ccc cag tgt gca ccc ctg act<br>Pro Lys Gln Leu Thr Thr Asp Gly Leu Pro Gln Cys Ala Pro Leu Thr<br>                     575                          580                     585 | 1961 |
| gtg ctt gac ttc ttt gaa ggc agc agc cct ggt ttt gcc atc acc atc<br>Val Leu Asp Phe Phe Glu Gly Ser Ser Pro Gly Phe Ala Ile Thr Ile<br>590                          595                     600 | 2009 |
| att gct ctc tgc tgc ctt ccc tta gtg agt ctg ctt ctc tct gga gtg<br>Ile Ala Leu Cys Cys Leu Pro Leu Val Ser Leu Leu Leu Ser Gly Val<br>605                          610                     615 | 2057 |
| gtg gcc tat ttc cgg ggc cga gaa cac aag aag cta caa aag aaa ctc<br>Val Ala Tyr Phe Arg Gly Arg Glu His Lys Lys Leu Gln Lys Lys Leu<br>620                          625                     630 | 2105 |
| aaa gag agc gtg aag aag gaa gca gcc aaa gat gga gtg cca gcg atg<br>Lys Glu Ser Val Lys Lys Glu Ala Ala Lys Asp Gly Val Pro Ala Met<br>635                          640                     645                     650 | 2153 |
| gag tgg cca ggc ccc aag gag agg agc agt ccc atc atc atc cag ctg<br>Glu Trp Pro Gly Pro Lys Glu Arg Ser Ser Pro Ile Ile Ile Gln Leu<br>                     655                          660                     665 | 2201 |
| ctg tca gac agg tgt ctg cag gtc ctg aac agg cat ctc act gtg ctc<br>Leu Ser Asp Arg Cys Leu Gln Val Leu Asn Arg His Leu Thr Val Leu<br>                     670                          675                     680 | 2249 |
| cgt gtg gtc cag ctg cag cct ctg cag cag gtc aac ctc atc ctg tcc<br>Arg Val Val Gln Leu Gln Pro Leu Gln Gln Val Asn Leu Ile Leu Ser<br>685                          690                     695 | 2297 |
| aac aac cga gga tgc cgc acc ctg ctg ctc aag atc cct aag gag tat<br>Asn Asn Arg Gly Cys Arg Thr Leu Leu Leu Lys Ile Pro Lys Glu Tyr<br>700                          705                     710 | 2345 |
| gac ctg gtg ctg ctg ttt agt tct gaa gag gaa cgg ggc gcc ttt gtg<br>Asp Leu Val Leu Leu Phe Ser Ser Glu Glu Glu Arg Gly Ala Phe Val<br>715                          720                     725                     730 | 2393 |
| cag cag cta tgg gac ttc tgc gtg cgc tgg gct ctg ggc ctc cat gtg<br>Gln Gln Leu Trp Asp Phe Cys Val Arg Trp Ala Leu Gly Leu His Val<br>                     735                          740                     745 | 2441 |
| gct gag atg agc gag aag gag cta ttt agg aag gct gtg aca aag cag<br>Ala Glu Met Ser Glu Lys Glu Leu Phe Arg Lys Ala Val Thr Lys Gln<br>                     750                          755                     760 | 2489 |
| cag cgg gaa cgc atc ctg gag atc ttc ttc aga cac ctt ttt gct cag<br>Gln Arg Glu Arg Ile Leu Glu Ile Phe Phe Arg His Leu Phe Ala Gln<br>765                          770                     775 | 2537 |
| gtg ctg gac atc aac cag gcc gac gca ggg acc ctg ccc ctg gac tcc<br>Val Leu Asp Ile Asn Gln Ala Asp Ala Gly Thr Leu Pro Leu Asp Ser<br>780                          785                     790 | 2585 |
| tcc cag aag gtg cgg gag gcc ctg acc tgc gag ctg agc agg gcc gag<br>Ser Gln Lys Val Arg Glu Ala Leu Thr Cys Glu Leu Ser Arg Ala Glu<br>795                          800                     805                     810 | 2633 |
| ttt gcc gag tcc ctg ggc ctc aag ccc cag gac atg ttt gtg gag tcc<br>Phe Ala Glu Ser Leu Gly Leu Lys Pro Gln Asp Met Phe Val Glu Ser | 2681 |

-continued

| | | | |
|---|---|---|---|
| | 815 | 820 | 825 |
| atg ttc tct ctg gct gac aag gat ggc aat ggc tac ctg tcc ttc cga<br>Met Phe Ser Leu Ala Asp Lys Asp Gly Asn Gly Tyr Leu Ser Phe Arg<br>830 835 840 | | | 2729 |
| gag ttc ctg gac atc ctg gtg gtc ttc atg aaa ggc tcc cca gag gat<br>Glu Phe Leu Asp Ile Leu Val Val Phe Met Lys Gly Ser Pro Glu Asp<br>845 850 855 | | | 2777 |
| aag tcc cgt cta atg ttt acc atg tat gac ctg gat gag aat ggc ttc<br>Lys Ser Arg Leu Met Phe Thr Met Tyr Asp Leu Asp Glu Asn Gly Phe<br>860 865 870 | | | 2825 |
| ctc tcc aag gac gaa ttc ttc acc atg atg cga tcc ttc atc gag atc<br>Leu Ser Lys Asp Glu Phe Phe Thr Met Met Arg Ser Phe Ile Glu Ile<br>875 880 885 890 | | | 2873 |
| tcc aac aac tgc ctg tcc aag gcc cag ctg gcc gag gtg gtg gag tct<br>Ser Asn Asn Cys Leu Ser Lys Ala Gln Leu Ala Glu Val Val Glu Ser<br>895 900 905 | | | 2921 |
| atg ttc cgg gag tcg gga ttc cag gac aag gag gag ctg aca tgg gag<br>Met Phe Arg Glu Ser Gly Phe Gln Asp Lys Glu Glu Leu Thr Trp Glu<br>910 915 920 | | | 2969 |
| gat ttt cac ttc atg ctg cgg gac cat gac agc gag ctc cgc ttc acg<br>Asp Phe His Phe Met Leu Arg Asp His Asp Ser Glu Leu Arg Phe Thr<br>925 930 935 | | | 3017 |
| cag ctc tgt gtc aaa ggt gga ggt gga ggt gga aat ggt att aga gat<br>Gln Leu Cys Val Lys Gly Gly Gly Gly Gly Asn Gly Ile Arg Asp<br>940 945 950 | | | 3065 |
| atc ttt aaa caa aac atc agc tgt cga gtc tcg ttc atc act cgg aca<br>Ile Phe Lys Gln Asn Ile Ser Cys Arg Val Ser Phe Ile Thr Arg Thr<br>955 960 965 970 | | | 3113 |
| cct ggg gag cgc tcc cac ccc cag gga ctg ggg ccc cct gcc cca gaa<br>Pro Gly Glu Arg Ser His Pro Gln Gly Leu Gly Pro Pro Ala Pro Glu<br>975 980 985 | | | 3161 |
| gcc cca gag ctg gga ggc cct gga ctg aag aag agg ttt ggc aaa aag<br>Ala Pro Glu Leu Gly Gly Pro Gly Leu Lys Lys Arg Phe Gly Lys Lys<br>990 995 1000 | | | 3209 |
| gca gca gtg ccc act ccc cgg ctg tac aca gag gcg ctg caa gag<br>Ala Ala Val Pro Thr Pro Arg Leu Tyr Thr Glu Ala Leu Gln Glu<br>1005 1010 1015 | | | 3254 |
| aag atg cag cga ggc ttc cta gcc caa aag ctg cag cag tac aag<br>Lys Met Gln Arg Gly Phe Leu Ala Gln Lys Leu Gln Gln Tyr Lys<br>1020 1025 1030 | | | 3299 |
| cgc ttc gtg gag aac tac cgg agg cac atc gtg tgt gtg gca atc<br>Arg Phe Val Glu Asn Tyr Arg Arg His Ile Val Cys Val Ala Ile<br>1035 1040 1045 | | | 3344 |
| ttc tcg gcc atc tgt gtt ggc gtg ttt gca gat cgt gct tac tac<br>Phe Ser Ala Ile Cys Val Gly Val Phe Ala Asp Arg Ala Tyr Tyr<br>1050 1055 1060 | | | 3389 |
| tat ggc ttt gcc tcg cca ccc tcg gac att gca cag acc acc ctc<br>Tyr Gly Phe Ala Ser Pro Pro Ser Asp Ile Ala Gln Thr Thr Leu<br>1065 1070 1075 | | | 3434 |
| gtg ggc atc atc ctg tca cga ggc acg gcg gcc agc gtc tcc ttc<br>Val Gly Ile Ile Leu Ser Arg Gly Thr Ala Ala Ser Val Ser Phe<br>1080 1085 1090 | | | 3479 |
| atg ttc tct tat atc ttg ctc acc atg tgc cgc aac ctc ata acc<br>Met Phe Ser Tyr Ile Leu Leu Thr Met Cys Arg Asn Leu Ile Thr<br>1095 1100 1105 | | | 3524 |
| ttc ctg cga gag act ttc ctc aac cgc tat gtg cct ttt gat gcc<br>Phe Leu Arg Glu Thr Phe Leu Asn Arg Tyr Val Pro Phe Asp Ala<br>1110 1115 1120 | | | 3569 |
| gca gtg gac ttc cac cgc tgg atc gcc atg gct gct gtt gtc ctg | | | 3614 |

-continued

| | | | | | | | | | | | | |
|---|---|---|---|---|---|---|---|---|---|---|---|---|
| Ala | Val | Asp<br>1125 | Phe | His | Arg<br>1130 | Trp | Ile | Ala | Met<br>1135 | Ala | Val | Val Leu |
| gcc | att | ttg | cac | agt | gct | ggc | cac | gca | gtc | aat | gtc | tac atc ttc | 3659
| Ala | Ile | Leu<br>1140 | His | Ser | Ala | Gly | His<br>1145 | Ala | Val | Asn | Val | Tyr Ile Phe<br>1150 |
| tca | gtc | agc | cca | ctc | agc | ctg | ctg | gcc | tgc | ata | ttc | ccc aac gtc | 3704
| Ser | Val | Ser<br>1155 | Pro | Leu | Ser | Leu | Leu<br>1160 | Ala | Cys | Ile | Phe | Pro Asn Val<br>1165 |
| ttt | gtg | aat | gat | ggg | tcc | aag | ctt | ccc | cag | aag | ttc | tat tgg tgg | 3749
| Phe | Val | Asn<br>1170 | Asp | Gly | Ser | Lys | Leu<br>1175 | Pro | Gln | Lys | Phe | Tyr Trp Trp<br>1180 |
| ttc | ttc | cag | acc | gtc | cca | ggt | atg | aca | ggt | gtg | ctt | ctc ctg | 3794
| Phe | Phe | Gln<br>1185 | Thr | Val | Pro | Gly | Met<br>1190 | Thr | Gly | Val | Leu | Leu Leu<br>1195 |
| gtc | ctg | gcc | atc | atg | tat | gtc | ttc | gcc | tcc | cac | cac | ttc cgc cgc | 3839
| Val | Leu | Ala<br>1200 | Ile | Met | Tyr | Val | Phe<br>1205 | Ala | Ser | His | His | Phe Arg Arg<br>1210 |
| cgc | agc | ttc | cgg | ggc | ttc | tgg | ctg | acc | cac | cac | ctc | tac atc ctg | 3884
| Arg | Ser | Phe<br>1215 | Arg | Gly | Phe | Trp | Leu<br>1220 | Thr | His | His | Leu | Tyr Ile Leu<br>1225 |
| ctc | tat | gcc | ctg | ctc | atc | atc | cat | ggc | agc | tat | gct | ctg atc cag | 3929
| Leu | Tyr | Ala<br>1230 | Leu | Leu | Ile | Ile | His<br>1235 | Gly | Ser | Tyr | Ala | Leu Ile Gln<br>1240 |
| ctg | ccc | act | ttc | cac | atc | tac | ttc | ctg | gtc | ccg | gca | atc atc tat | 3974
| Leu | Pro | Thr<br>1245 | Phe | His | Ile | Tyr | Phe<br>1250 | Leu | Val | Pro | Ala | Ile Ile Tyr<br>1255 |
| gga | ggt | gac | aag | ctg | gtg | agc | ctg | agc | cgg | aag | aag | gtg gag atc | 4019
| Gly | Gly | Asp<br>1260 | Lys | Leu | Val | Ser | Leu<br>1265 | Ser | Arg | Lys | Lys | Val Glu Ile<br>1270 |
| agc | gtg | gtg | aag | gcg | gag | ctg | ctg | ccc | tca | gga | gtg | acc tac ctg | 4064
| Ser | Val | Val<br>1275 | Lys | Ala | Glu | Leu | Leu<br>1280 | Pro | Ser | Gly | Val | Thr Tyr Leu<br>1285 |
| caa | ttc | cag | agg | ccc | caa | ggc | ttt | gag | tac | aag | tca | gga cag tgg | 4109
| Gln | Phe | Gln<br>1290 | Arg | Pro | Gln | Gly | Phe<br>1295 | Glu | Tyr | Lys | Ser | Gly Gln Trp<br>1300 |
| gtg | cgg | atc | gcc | tgc | ctg | gct | ctg | ggg | acc | acc | gag | tac cac ccc | 4154
| Val | Arg | Ile<br>1305 | Ala | Cys | Leu | Ala | Leu<br>1310 | Gly | Thr | Thr | Glu | Tyr His Pro<br>1315 |
| ttc | aca | ctg | acc | tcc | gcg | ccc | cat | gag | gac | aca | ctc | agc ctg cac | 4199
| Phe | Thr | Leu<br>1320 | Thr | Ser | Ala | Pro | His<br>1325 | Glu | Asp | Thr | Leu | Ser Leu His<br>1330 |
| atc | cgg | gca | gtg | ggg | ccc | tgg | acc | act | cgc | ctc | agg | gag atc tac | 4244
| Ile | Arg | Ala<br>1335 | Val | Gly | Pro | Trp | Thr<br>1340 | Thr | Arg | Leu | Arg | Glu Ile Tyr<br>1345 |
| tca | tcc | cca | aag | ggc | aat | ggc | tgt | gct | gga | tac | cca | aag ctg tac | 4289
| Ser | Ser | Pro<br>1350 | Lys | Gly | Asn | Gly | Cys<br>1355 | Ala | Gly | Tyr | Pro | Lys Leu Tyr<br>1360 |
| ctt | gat | gga | ccg | ttt | gga | gag | ggc | cat | cag | gag | tgg | cat aaa ttt | 4334
| Leu | Asp | Gly<br>1365 | Pro | Phe | Gly | Glu | Gly<br>1370 | His | Gln | Glu | Trp | His Lys Phe<br>1375 |
| gag | gtg | tca | gtg | ttg | gtg | gga | ggg | ggc | att | ggg | gtc | acc ccc ttt | 4379
| Glu | Val | Ser<br>1380 | Val | Leu | Val | Gly | Gly<br>1385 | Gly | Ile | Gly | Val | Thr Pro Phe<br>1390 |
| gcc | tcc | atc | ctc | aaa | gac | ctg | gtc | ttc | aag | tca | tcc | ttg ggc agc | 4424
| Ala | Ser | Ile<br>1395 | Leu | Lys | Asp | Leu | Val<br>1400 | Phe | Lys | Ser | Ser | Leu Gly Ser<br>1405 |
| caa | atg | ctg | tgt | aag | aag | atc | tac | ttc | atc | tgg | gtg | aca cgg acc | 4469
| Gln | Met | Leu<br>1410 | Cys | Lys | Lys | Ile | Tyr<br>1415 | Phe | Ile | Trp | Val | Thr Arg Thr<br>1420 |

```
                                                            -continued
cag cgt cag ttt gag tgg ctg gct gac atc atc caa gag gtg gag      4514
Gln Arg Gln Phe Glu Trp Leu Ala Asp Ile Ile Gln Glu Val Glu
        1425                1430                1435 gag aac gac cac cag gac ctg gtg tct gtg cac att tat gtc acc      4559
Glu Asn Asp His Gln Asp Leu Val Ser Val His Ile Tyr Val Thr
    1440                1445                1450 cag ctg gct gag aag ttc gac ctc agg acc acc atg cta tac atc      4604
Gln Leu Ala Glu Lys Phe Asp Leu Arg Thr Thr Met Leu Tyr Ile
        1455                1460                1465 tgc gag cgg cac ttc cag aaa gtg ctg aac cgg agt ctg ttc acg      4649
Cys Glu Arg His Phe Gln Lys Val Leu Asn Arg Ser Leu Phe Thr
        1470                1475                1480 ggc ctg cgc tcc atc acc cac ttt ggc cgt ccc ccc ttc gag ccc      4694
Gly Leu Arg Ser Ile Thr His Phe Gly Arg Pro Pro Phe Glu Pro
        1485                1490                1495 ttc ttc aac tcc ctg cag gag gtc cac cca cag gtg cgc aag atc      4739
Phe Phe Asn Ser Leu Gln Glu Val His Pro Gln Val Arg Lys Ile
        1500                1505                1510 ggg gtg ttc agc tgc ggc cct cca gga atg acc aag aat gta gag      4784
Gly Val Phe Ser Cys Gly Pro Pro Gly Met Thr Lys Asn Val Glu
        1515                1520                1525 aag gcc tgt cag ctc gtc aac agg cag gac cga gcc cac ttc atg      4829
Lys Ala Cys Gln Leu Val Asn Arg Gln Asp Arg Ala His Phe Met
        1530                1535                1540 cac cac tat gag aac ttc tga gcctgtcctc cctggctgct gcttccagta     4880
His His Tyr Glu Asn Phe
        1545 tcctgccttc tcttctgtgc acctaagttg cccagccctg ctggcaatct ctccatcaga    4940 atccaccttz ggcctcagct ggagggctgc agagcccctc ccaatattgg gagaatattg    5000 acccagacaa ttatacaaat gagaaaaggc aggagactat gttctacaat tgcagtgcat    5060 gatgattata agtccacctg tttatcaacg gcaccattcc tgcagccctc cagacttcct    5120 gcccttagca agtgcgcaac cagtcaggat ctcccaaaga agataaagac cactcctcac    5180 cccagctcaa gccatggcag gcgtggcaag caaagtgggg aggagacagt ccctgcttgt    5240 gacaagtgtg gaggtgaaaa ggtacaatag tgcttgtctc cgatagctcc ccacatctct    5300 aattgacttc cacaaaatcg atgcgttgct ttggtatttg cttggactga catttgaggg    5360 aggaggaggc tgggatcctc tggctgagaa tctcctcaga gcccagtgca gaagctgtga    5420 tgcttagaac ctggacagcc cgactgcctc aactctgtct ccaggtctat tccctccagc    5480 tccaaaagga gcagccctac ttctacccct cccgtcccc aaagtgtcag caactttgag     5540 gagggcacca ggaaacaaag atgcctcccc agccctgata ttcttgatgt caccagtgat    5600 acccactgcc ctgaccctg gcaggcccc tctctgcatc tactggagtg gtccctgggc      5660 tctgggctg aaggattcca gcctctctgc cagatattca gtactcgatc tcaattcccc     5720 tcttccacaa gagttgggtg accagctgtc ctagtttgcc caggactctc cctgttttag    5780 cactgaaagt ctcttgcccc aggaaacccc atcagtccca ggcagattgg gacagctggt    5840 caccttacgc aagagccagg ctgaaacatc ccctccatac tcagtctttt aacttttctt    5900 ttccttttc atcgggctct ttcctaaaaa gctgagctgt aaaatatttt acatcgaggt     5960 ataataaata atcatgtaca tgttttacca ccacccaggt caagacatag aatgtttcaa    6020 catttccatc accccagaaa ctccccttgt accccttcc acttcgtctc ccctagctcc     6080 tagaagcaac cactgatgtg atttctacca aatccagttt tggtcctact aaatatactc    6140 ttttgagact ggcctctttt actcaccata atgcctttgt aattcatcca tgctgttgtg    6200
```

-continued

```
tgtatcagca gtttgttcct tttcattgct gagtagtatt ctattgtaga gatgtaccac    6260
agtttgttta ttcttctgtt gatggacgtt tgggttgttt ctaattttga atgattataa    6320
ataaaaattc tgtgagtgtt cttgtaaaaa aaaaaaaaaa aaaaaaaaaa aaaaaa        6376

<210> SEQ ID NO 14
<211> LENGTH: 1548
<212> TYPE: PRT
<213> ORGANISM: Homo sapiens

<400> SEQUENCE: 14

Met Leu Arg Ala Arg Pro Glu Ala Leu Met Leu Leu Gly Ala Leu Leu
1               5                   10                  15

Thr Gly Ser Leu Gly Pro Ser Gly Ser Gln Asp Ala Leu Ser Leu Pro
            20                  25                  30

Trp Glu Val Gln Arg Tyr Asp Gly Trp Phe Asn Asn Leu Arg His His
        35                  40                  45

Glu Arg Gly Ala Val Gly Cys Arg Leu Gln Arg Val Pro Ala Asn
    50                  55                  60

Tyr Ala Asp Gly Val Tyr Gln Ala Leu Glu Glu Pro Gln Leu Pro Asn
65                  70                  75                  80

Pro Arg Arg Leu Ser Asn Ala Ala Thr Arg Gly Ile Ala Gly Leu Pro
                85                  90                  95

Ser Leu His Asn Arg Thr Val Leu Gly Val Phe Phe Gly Tyr His Val
            100                 105                 110

Leu Ser Asp Val Val Ser Val Glu Thr Pro Gly Cys Pro Ala Glu Phe
        115                 120                 125

Leu Asn Ile Arg Ile Pro Pro Gly Asp Pro Val Phe Asp Pro Asp Gln
    130                 135                 140

Arg Gly Asp Val Val Leu Pro Phe Gln Arg Ser Arg Trp Asp Pro Glu
145                 150                 155                 160

Thr Gly Arg Ser Pro Ser Asn Pro Arg Asp Leu Ala Asn Gln Val Thr
                165                 170                 175

Gly Trp Leu Asp Gly Ser Ala Ile Tyr Gly Ser Ser His Ser Trp Ser
            180                 185                 190

Asp Ala Leu Arg Ser Phe Ser Gly Gln Leu Ala Ser Gly Pro Asp
        195                 200                 205

Pro Ala Phe Pro Arg Asp Ser Gln Asn Pro Leu Leu Met Trp Ala Ala
    210                 215                 220

Pro Asp Pro Ala Thr Gly Gln Asn Gly Pro Arg Gly Leu Tyr Ala Phe
225                 230                 235                 240

Gly Ala Glu Arg Gly Asn Arg Glu Pro Phe Leu Gln Ala Leu Gly Leu
                245                 250                 255

Leu Trp Phe Arg Tyr His Asn Leu Trp Ala Gln Arg Leu Ala Arg Gln
            260                 265                 270

His Pro Asp Trp Glu Asp Glu Leu Phe Gln His Ala Arg Lys Arg
        275                 280                 285

Val Ile Ala Thr Tyr Gln Asn Ile Ala Val Tyr Glu Trp Leu Pro Ser
    290                 295                 300

Phe Leu Gln Lys Thr Leu Pro Gly Tyr Thr Gly Tyr Arg Pro Phe Leu
305                 310                 315                 320

Asp Pro Ser Ile Ser Pro Glu Phe Val Val Ala Ser Glu Gln Phe Phe
                325                 330                 335

Ser Thr Met Val Pro Pro Gly Val Tyr Met Arg Asn Ala Ser Cys His
```

-continued

```
                    340                 345                 350
        Phe Arg Lys Val Leu Asn Lys Gly Phe Gln Ser Ser Gln Ala Leu Arg
                    355                 360                 365
        Val Cys Asn Asn Tyr Trp Ile Arg Glu Asn Pro Asn Leu Asn Ser Thr
                    370                 375                 380
        Gln Glu Val Asn Glu Leu Leu Leu Gly Met Ala Ser Gln Ile Ser Glu
        385                 390                 395                 400
        Leu Glu Asp Asn Ile Val Val Glu Asp Leu Arg Asp Tyr Trp Pro Gly
                            405                 410                 415
        Pro Gly Lys Phe Ser Arg Thr Asp Tyr Val Ala Ser Ser Ile Gln Arg
                    420                 425                 430
        Gly Arg Asp Met Gly Leu Pro Ser Tyr Ser Gln Ala Leu Leu Ala Phe
                    435                 440                 445
        Gly Leu Asp Ile Pro Arg Asn Trp Ser Asp Leu Asn Pro Asn Val Asp
                    450                 455                 460
        Pro Gln Val Leu Glu Ala Thr Ala Leu Tyr Asn Gln Asp Leu Ser
        465                 470                 475                 480
        Gln Leu Glu Leu Leu Gly Leu Leu Glu Ser His Gly Asp Pro
                            485                 490                 495
        Gly Pro Leu Phe Ser Ala Ile Val Leu Asp Gln Phe Val Arg Leu Arg
                    500                 505                 510
        Asp Gly Asp Arg Tyr Trp Phe Glu Asn Thr Arg Asn Gly Leu Phe Ser
                    515                 520                 525
        Lys Lys Glu Ile Glu Asp Ile Arg Asn Thr Thr Leu Arg Asp Val Leu
                    530                 535                 540
        Val Ala Val Ile Asn Ile Asp Pro Ser Ala Leu Gln Pro Asn Val Phe
        545                 550                 555                 560
        Val Trp His Lys Gly Ala Pro Cys Pro Gln Pro Lys Gln Leu Thr Thr
                            565                 570                 575
        Asp Gly Leu Pro Gln Cys Ala Pro Leu Thr Val Leu Asp Phe Phe Glu
                    580                 585                 590
        Gly Ser Ser Pro Gly Phe Ala Ile Thr Ile Ile Ala Leu Cys Cys Leu
                    595                 600                 605
        Pro Leu Val Ser Leu Leu Ser Gly Val Val Ala Tyr Phe Arg Gly
                    610                 615                 620
        Arg Glu His Lys Lys Leu Gln Lys Leu Lys Glu Ser Val Lys Lys
        625                 630                 635                 640
        Glu Ala Ala Lys Asp Gly Val Pro Ala Met Glu Trp Pro Gly Pro Lys
                            645                 650                 655
        Glu Arg Ser Ser Pro Ile Ile Ile Gln Leu Leu Ser Asp Arg Cys Leu
                    660                 665                 670
        Gln Val Leu Asn Arg His Leu Thr Val Leu Arg Val Gln Leu Gln
                    675                 680                 685
        Pro Leu Gln Gln Val Asn Leu Ile Leu Ser Asn Asn Arg Gly Cys Arg
                    690                 695                 700
        Thr Leu Leu Leu Lys Ile Pro Lys Glu Tyr Asp Leu Val Leu Leu Phe
        705                 710                 715                 720
        Ser Ser Glu Glu Glu Arg Gly Ala Phe Val Gln Gln Leu Trp Asp Phe
                            725                 730                 735
        Cys Val Arg Trp Ala Leu Gly Leu His Val Ala Glu Met Ser Glu Lys
                    740                 745                 750
        Glu Leu Phe Arg Lys Ala Val Thr Lys Gln Gln Arg Glu Arg Ile Leu
                    755                 760                 765
```

-continued

```
Glu Ile Phe Phe Arg His Leu Phe Ala Gln Val Leu Asp Ile Asn Gln
    770                 775                 780
Ala Asp Ala Gly Thr Leu Pro Leu Asp Ser Ser Gln Lys Val Arg Glu
785                 790                 795                 800
Ala Leu Thr Cys Glu Leu Ser Arg Ala Glu Phe Ala Glu Ser Leu Gly
                805                 810                 815
Leu Lys Pro Gln Asp Met Phe Val Glu Ser Met Phe Ser Leu Ala Asp
                820                 825                 830
Lys Asp Gly Asn Gly Tyr Leu Ser Phe Arg Glu Phe Leu Asp Ile Leu
                835                 840                 845
Val Val Phe Met Lys Gly Ser Pro Glu Asp Lys Ser Arg Leu Met Phe
850                 855                 860
Thr Met Tyr Asp Leu Asp Glu Asn Gly Phe Leu Ser Lys Asp Glu Phe
865                 870                 875                 880
Phe Thr Met Met Arg Ser Phe Ile Glu Ile Ser Asn Asn Cys Leu Ser
                885                 890                 895
Lys Ala Gln Leu Ala Glu Val Val Glu Ser Met Phe Arg Glu Ser Gly
                900                 905                 910
Phe Gln Asp Lys Glu Glu Leu Thr Trp Glu Asp Phe His Phe Met Leu
                915                 920                 925
Arg Asp His Asp Ser Glu Leu Arg Phe Thr Gln Leu Cys Val Lys Gly
    930                 935                 940
Gly Gly Gly Gly Gly Asn Gly Ile Arg Asp Ile Phe Lys Gln Asn Ile
945                 950                 955                 960
Ser Cys Arg Val Ser Phe Ile Thr Arg Thr Pro Gly Glu Arg Ser His
                965                 970                 975
Pro Gln Gly Leu Gly Pro Pro Ala Pro Glu Ala Pro Glu Leu Gly Gly
                980                 985                 990
Pro Gly Leu Lys Lys Arg Phe Gly Lys Lys Ala Ala Val Pro Thr Pro
    995                 1000                1005
Arg Leu Tyr Thr Glu Ala Leu Gln Glu Lys Met Gln Arg Gly Phe
    1010                1015                1020
Leu Ala Gln Lys Leu Gln Gln Tyr Lys Arg Phe Val Glu Asn Tyr
    1025                1030                1035
Arg Arg His Ile Val Cys Val Ala Ile Phe Ser Ala Ile Cys Val
    1040                1045                1050
Gly Val Phe Ala Asp Arg Ala Tyr Tyr Tyr Gly Phe Ala Ser Pro
    1055                1060                1065
Pro Ser Asp Ile Ala Gln Thr Thr Leu Val Gly Ile Ile Leu Ser
    1070                1075                1080
Arg Gly Thr Ala Ala Ser Val Ser Phe Met Phe Ser Tyr Ile Leu
    1085                1090                1095
Leu Thr Met Cys Arg Asn Leu Ile Thr Phe Leu Arg Glu Thr Phe
    1100                1105                1110
Leu Asn Arg Tyr Val Pro Phe Asp Ala Ala Val Asp Phe His Arg
    1115                1120                1125
Trp Ile Ala Met Ala Ala Val Val Leu Ala Ile Leu His Ser Ala
    1130                1135                1140
Gly His Ala Val Asn Val Tyr Ile Phe Ser Val Ser Pro Leu Ser
    1145                1150                1155
Leu Leu Ala Cys Ile Phe Pro Asn Val Phe Val Asn Asp Gly Ser
    1160                1165                1170
```

-continued

| | | | | | | | | | | | | |
|---|---|---|---|---|---|---|---|---|---|---|---|---|
| Lys | Leu | Pro | Gln | Lys | Phe | Tyr | Trp | Trp | Phe | Gln | Thr | Val | Pro |
| 1175 | | | | | 1180 | | | | | 1185 | | | |
| Gly | Met | Thr | Gly | Val | Leu | Leu | Leu | Val | Leu | Ala | Ile | Met | Tyr |
| 1190 | | | | | 1195 | | | | | 1200 | | | |
| Val | Phe | Ala | Ser | His | His | Phe | Arg | Arg | Arg | Ser | Phe | Arg | Gly | Phe |
| 1205 | | | | | 1210 | | | | | 1215 | | | |
| Trp | Leu | Thr | His | His | Leu | Tyr | Ile | Leu | Leu | Tyr | Ala | Leu | Leu | Ile |
| 1220 | | | | | 1225 | | | | | 1230 | | | |
| Ile | His | Gly | Ser | Tyr | Ala | Leu | Ile | Gln | Leu | Pro | Thr | Phe | His | Ile |
| 1235 | | | | | 1240 | | | | | 1245 | | | |
| Tyr | Phe | Leu | Val | Pro | Ala | Ile | Ile | Tyr | Gly | Gly | Asp | Lys | Leu | Val |
| 1250 | | | | | 1255 | | | | | 1260 | | | |
| Ser | Leu | Ser | Arg | Lys | Lys | Val | Glu | Ile | Ser | Val | Val | Lys | Ala | Glu |
| 1265 | | | | | 1270 | | | | | 1275 | | | |
| Leu | Leu | Pro | Ser | Gly | Val | Thr | Tyr | Leu | Gln | Phe | Gln | Arg | Pro | Gln |
| 1280 | | | | | 1285 | | | | | 1290 | | | |
| Gly | Phe | Glu | Tyr | Lys | Ser | Gly | Gln | Trp | Val | Arg | Ile | Ala | Cys | Leu |
| 1295 | | | | | 1300 | | | | | 1305 | | | |
| Ala | Leu | Gly | Thr | Thr | Glu | Tyr | His | Pro | Phe | Thr | Leu | Thr | Ser | Ala |
| 1310 | | | | | 1315 | | | | | 1320 | | | |
| Pro | His | Glu | Asp | Thr | Leu | Ser | Leu | His | Ile | Arg | Ala | Val | Gly | Pro |
| 1325 | | | | | 1330 | | | | | 1335 | | | |
| Trp | Thr | Thr | Arg | Leu | Arg | Glu | Ile | Tyr | Ser | Ser | Pro | Lys | Gly | Asn |
| 1340 | | | | | 1345 | | | | | 1350 | | | |
| Gly | Cys | Ala | Gly | Tyr | Pro | Lys | Leu | Tyr | Leu | Asp | Gly | Pro | Phe | Gly |
| 1355 | | | | | 1360 | | | | | 1365 | | | |
| Glu | Gly | His | Gln | Glu | Trp | His | Lys | Phe | Glu | Val | Ser | Val | Leu | Val |
| 1370 | | | | | 1375 | | | | | 1380 | | | |
| Gly | Gly | Gly | Ile | Gly | Val | Thr | Pro | Phe | Ala | Ser | Ile | Leu | Lys | Asp |
| 1385 | | | | | 1390 | | | | | 1395 | | | |
| Leu | Val | Phe | Lys | Ser | Ser | Leu | Gly | Ser | Gln | Met | Leu | Cys | Lys | Lys |
| 1400 | | | | | 1405 | | | | | 1410 | | | |
| Ile | Tyr | Phe | Ile | Trp | Val | Thr | Arg | Thr | Gln | Arg | Gln | Phe | Glu | Trp |
| 1415 | | | | | 1420 | | | | | 1425 | | | |
| Leu | Ala | Asp | Ile | Ile | Gln | Glu | Val | Glu | Glu | Asn | Asp | His | Gln | Asp |
| 1430 | | | | | 1435 | | | | | 1440 | | | |
| Leu | Val | Ser | Val | His | Ile | Tyr | Val | Thr | Gln | Leu | Ala | Glu | Lys | Phe |
| 1445 | | | | | 1450 | | | | | 1455 | | | |
| Asp | Leu | Arg | Thr | Thr | Met | Leu | Tyr | Ile | Cys | Glu | Arg | His | Phe | Gln |
| 1460 | | | | | 1465 | | | | | 1470 | | | |
| Lys | Val | Leu | Asn | Arg | Ser | Leu | Phe | Thr | Gly | Leu | Arg | Ser | Ile | Thr |
| 1475 | | | | | 1480 | | | | | 1485 | | | |
| His | Phe | Gly | Arg | Pro | Pro | Phe | Glu | Pro | Phe | Phe | Asn | Ser | Leu | Gln |
| 1490 | | | | | 1495 | | | | | 1500 | | | |
| Glu | Val | His | Pro | Gln | Val | Arg | Lys | Ile | Gly | Val | Phe | Ser | Cys | Gly |
| 1505 | | | | | 1510 | | | | | 1515 | | | |
| Pro | Pro | Gly | Met | Thr | Lys | Asn | Val | Glu | Lys | Ala | Cys | Gln | Leu | Val |
| 1520 | | | | | 1525 | | | | | 1530 | | | |
| Asn | Arg | Gln | Asp | Arg | Ala | His | Phe | Met | His | His | Tyr | Glu | Asn | Phe |
| 1535 | | | | | 1540 | | | | | 1545 | | | |

<210> SEQ ID NO 15
<211> LENGTH: 797
<212> TYPE: DNA

<213> ORGANISM: Artificial Sequence
<220> FEATURE:
<223> OTHER INFORMATION: Synthetic primer

<400> SEQUENCE: 15

```
cggttttacc gctcccagca gaaggttgtg attaccaagg ttgttatgca cccatccaaa     60
gttttggaat tgcagatgaa caagcgtggc ttcagcatgg aagtggggca gtatatcttt    120
gttaattgcc cctcaatctc tctcctggaa tggcatcctt ttactttgac ctctgctcca    180
gaggaagatt tcttctccat tcatatccga gcagcagggg actggacaga aaatctcata    240
agggctttcg aacaacaata ttcaccaatt cccaggattg aagtggatgg tcccttggc    300
acagccagtg aggatgtttt ccagtatgaa gtggctgtgc tggttggagc aggaattggg    360
gtcacccccct ttgcttctat cttgaaatcc atctggtaca aattccagtg tgcagaccac    420
aacctcaaaa caaaaaagat ctatttctac tggatctgca gggagacagg tgcctttttcc    480
tggttcaaca acctgttgac ttccctggaa caggagatgg aggaattagg caaagtgggt    540
tttctaaact accgtctctt cctcaccgga tgggacagca atattgttgg tcatgcagca    600
ttaaactttg acaaggccac tgacatcgtg acaggtctga acagaaaac ctcctttggg    660
agaccaatgt gggacaatga gttttctaca atagctacct cccacccaa gtctgtagtg    720
ggagttttct tatgtggccc tcggactttg gcaaagagcc tgcgcaaatg ctgtcaccga    780
tattccagtc tggatcc                                                  797
```

<210> SEQ ID NO 16
<211> LENGTH: 24
<212> TYPE: DNA
<213> ORGANISM: Artificial Sequence
<220> FEATURE:
<223> OTHER INFORMATION: Synthetic primer

<400> SEQUENCE: 16

```
gtgaggatgt tttccagtat gaag                                           24
```

<210> SEQ ID NO 17
<211> LENGTH: 26
<212> TYPE: DNA
<213> ORGANISM: Artificial Sequence
<220> FEATURE:
<223> OTHER INFORMATION: Synthetic primer

<400> SEQUENCE: 17

```
tgtcaaagtt taatgctgca tgacca                                         26
```

<210> SEQ ID NO 18
<211> LENGTH: 24
<212> TYPE: DNA
<213> ORGANISM: Artificial Sequence
<220> FEATURE:
<223> OTHER INFORMATION: Synthetic primer

<400> SEQUENCE: 18

```
aactgaagat gttcgcgatt atct                                           24
```

<210> SEQ ID NO 19
<211> LENGTH: 23
<212> TYPE: DNA

-continued

```
<213> ORGANISM: Artificial Sequence
<220> FEATURE:
<223> OTHER INFORMATION: Synthetic primer

<400> SEQUENCE: 19
accgtcagta cgtgagatat ctt                                              23
```

METHODS AND TRANSGENIC MOUSE MODEL FOR IDENTIFYING AND MODULATING FACTORS INVOLVED IN THE PRODUCTION OF REACTIVE OXYGEN INTERMEDIATES

CROSS-REFERENCE TO RELATED APPLICATIONS

This application claims benefit of U.S. Provisional Patent Application Ser. No. 60/395,498 filed Jul. 12, 2002.

FIELD OF THE INVENTION

The present invention relates generally to the field of cellular proliferation and more specifically to a non-human animal model for overexpression of the gp91phox homologue family of nicotinamide adenine dinucleotide phosphate-reduced form (NADPH) oxidase (NOX) and dual oxidase (Duox) enzymes and generation of reactive oxygen intermediates.

BACKGROUND OF THE INVENTION

Reactive oxygen intermediates (ROI), which include the superoxide anion ($O_2^-$) and hydrogen peroxide ($H_2O_2$), result from the stepwise, monovalent reduction of oxygen: $O_2^-$ results from the addition of a single electron to $O_2$, and $H_2O_2$ results from the addition of a single electron to $O_2^-$. ROI are cytotoxic and mutagenic, with high levels of ROI causing damage to biomolecules such as DNA, proteins, and biomembranes. However, recent data indicate that lower levels of ROI may function in signal transduction as intracellular mediators of cell growth, cell proliferation, angiogenesis, apoptosis, and senescence.

Several biological systems generate ROI. For example, within the phagocytic-based immune defense against invading microbes, cells such as neutrophils produce large quantities of ROI via the nicotinamide adenine dinucleotide phosphate-reduced form (NADPH) oxidase (also known as the respiratory burst oxidase). The catalytic subunit of this enzyme, gp91phox, oxidizes NADPH and reduces oxygen to form $O_2^-$.

In many non-phagocytic cell types including cells in the colon, lung, brain and kidney, the gp91phox homologue family of NADPH oxidase (NOX) and dual oxidase (Duox) enzymes is responsible for producing low levels of ROI. At present, six human homologues of gp91phox have been identified, with additional homologs present in rat, mouse, *Caenorhabditis elegans*, and *Drosophila*.

Although the functions of NOX and Duox-derived ROI are unclear, several studies suggest that the non-phagocytic generation of ROI modulates cellular proliferation and activation of growth-related signaling pathways. For example, both fibroblasts and endothelial cells produce increased levels of superoxide in response to cytokines such as interleukin-1 and tumor necrosis factor (TNF). In rat vascular smooth muscle cells, exposure to platelet-derived growth factor (PDGF) increases the release of $H_2O_2$ while concomitantly increasing cell proliferation (Meier et al., Biochem. J. 263:539–45 (1989); Matsubara et al., J. Immun., 137:3295–98 (1986)). Additionally, data show that low levels of ROI elicit downstream effects on the redox-sensitive transcription factor nuclear factor kappa-B ($NF_\kappa$-B) and activator protein-1 (AP-I) (Schreck et al., EMBO J., 10:2247–58 (1991); Schmidt et al., Chemistry & Biology, 2:13–22(1995)).

Non-phagocytic ROI appear to have a direct role in regulating cell division, and may function as mitogenic signals in pathologic conditions related to cell growth, such as cancer and cardiovascular disease. For example, cytokine-mediated endothelial production of $O_2^-$ may play a role in angiogenesis (Matasubara et al., J. Immun., 137:3295–98 (1986)). Matasubara et al. have proposed that $O_2^-$ and $H_2O_2$ function as "life signals", preventing cells from undergoing apoptosis. (Matasubara et al., J. Immun., 137:3295–98 (1986)). Other data suggest that ROI mediate both pro-apoptotic and pro-survival signals. (Garg & Aggarwal, Mol. Immunol., 39:509–17 (2002)).

NOX Enzymes

A series of overexpression studies using the NOX1 enzyme of the NOX family of proteins indicates a specific role for NOX1-derived ROI in pathological conditions related to cell growth and proliferation. For example, overexpression of NOX1 in fibroblasts induces an $H_2O_2$-dependant malignant transformation, resulting in a highly tumorigenic phenotype (Arnold et al., Proc. Natl. Acad. Sci. USA, 89:5550–55 (2001); Suh et al., Nature (London), 401:79–82 (1999)). Consistent with these findings, overexpression of NOXI in prostate epithelial cells has been found to increase tumorigenicity. This increased epithelial cell tumorigenicity is also associated with increased tumor vascularity and increased expression of vascular endothelial growth factor (VEGF), indicating a specific role for NOX1 in angiogenesis. (Arbiser et al, Proc. Natl. Acad. Sci. USA, 99:715–20 (2002)).

One specific pathophysiological condition that may involve ROI is colorectal cancer (CRC), a form of cancer highly prevalent in the Western world. Sporadic colorectal cancer, which accounts for approximately 85% of diagnosed CRC, is linked to somatic mutations in the tumor suppressor gene adenomatous polyposis coli (APC). Genetic analyses of adenoma-carcinoma sequences for CRC indicate that mutations in APC are common, and may be the triggering event for the disease. The identification of a role for APC in CRC arises from the discovery of germline mutations in APC that result in the rare inherited form of colorectal cancer, familial adenomatous polyposis (FAP). Even though APC mutations may serve as a trigger for CRC, the fact that families carrying identical mutations in APC often exhibit varying degrees of colorectal cancer, both in severity and onset, suggests that other factors influence the function of APC. In other words, although a mutational loss of APC function may predispose an individual to colon cancer, other factors, such as ROI, may ultimately determine the onset and severity of CRC.

Duox Enzymes

Dual oxidases, or Duox, have both a peroxidase-homology domain and a gp91phox domain. It is currently believed that Duox enzymes have dual enzymatic functions, catalyzing both the generation of superoxide and peroxidative type reactions. The latter class of reactions utilizes hydrogen peroxide as a substrate. Since hydrogen peroxide is generated spontaneously from the dismutation of superoxide, it is believed that the NAD(P)H oxidase domain generates the superoxide and/or hydrogen peroxide which can then be used as a substrate for the peroxidase domain. The peroxidase domain is likely to confer additional biological functions. Depending upon the co-substrate, peroxidases can participate in a variety of reactions including halogenation such as the generation of hypochlorous acid (HOCl) by myeloperoxidase and the iodination of tyrosine to form thyroxin by thyroid peroxidase. Peroxidases have also been documented to participate in the metabolism of polyunsaturated fatty acids, and in the chemical modification of tyrosine in collagen. Duox is also theorized to function in the formation or modification of extracellular matrix or basement membrane. Since the extracellular matrix plays an important role in tumor cell growth, invasion and metastasis, it is believed that the Duox type enzymes play a pathogenic role in such conditions.

Although a strong link exists between NOX and Duox enzymes and ROI function in a multitude of different physiological and pathophysiological conditions, in vivo models to study this link in a tissue-specific fashion are lacking. Without such models, the extent to which NOX or Duox-generated ROI participate in cellular proliferation and activation of growth-related signaling pathways in different tissue types is difficult to ascertain. Similarly, the identification of NOX or Duox enzyme regulatory molecules is difficult in the absence of such models.

Accordingly, what is needed are in vivo and in vitro models to examine the effect of NOX and Duox-derived ROI on cell proliferation and activation of growth-related signaling pathways. Additionally, what is needed are in vivo and in vitro models to examine the effect of NOX and Duox-derived ROI on cell proliferation and activation of growth-related signaling pathways in a tissue specific manner. Also needed are in vivo and in vitro models to identify the regulators of NOX and Duox activity, including models to test the ability of different compounds to modulate the function of NOX and Duox and the effect of NOX and Duox-derived ROI on cellular proliferation and activation of growth-related signaling pathways.

SUMMARY

The present invention provides a transgenic non-human mammal, in particular a transgenic mouse, comprising a transgene encoding a member of the gp91phox homologue family of nicotinamide adenine dinucleotide phosphate-reduced form (NADPH) oxidase (NOX) and dual oxidase (Duox) proteins. The present invention also provides useful in vivo and in vitro models to examine the role of NOX and Duox proteins in the modulation of diseases and pathological conditions related to cell growth and proliferation.

The NOX and Duox family of proteins comprises NOX1 (SEQ ID NO:2), NOX2 (same as gp91phox) (SEQ ID NO:4), NOX3 (SEQ ID NO:6), NOX4 (SEQ ID NO:8), NOX5 (SEQ ID NO:10), Duox1 (SEQ ID NO:12) and Duox2 (SEQ ID NO:14) or modifications thereof. This family of proteins participates in the generation of reactive oxygen intermediates (ROI) and plays a role in several pathological conditions related to cell growth and proliferation, including, but not limited to, cancer, psoriasis, prostatic hypertrophy, benign prostatic hypertrophy, cardiovascular disease, proliferation of vessels, including but not limited to, blood vessels and lymphatic vessels, arteriovenous malformation, vascular problems associated with the eye, atherosclerosis, hypertension, and restenosis following angioplasty.

The present invention additionally provides DNA constructs comprising polynucleotides encoding a NOX or Duox polypeptide. In addition to NOX or Duox polypeptides, the invention also provides DNA constructs comprising polynucleotides encoding human NOX or Duox polypeptides and also NOX or Duox polypeptides from other species. DNA constructs containing the polypeptides can be incorporated into vectors for propagation or transfection into appropriate cells to generate NOX or Duox mutant non-human animals. The vectors may contain regulatory elements that provide for tissue specific or inducible expression of the nucleic acids and for expression of selectable markers for identification of the transfected cells. The present invention also comprises cells transfected with these DNA constructs, either in culture or integrated into the genome of the transgenic animal.

The present invention further provides methods for in vivo and in vitro identification of therapeutic agents, for example by screening chemical and drug libraries for compounds that alter the activity of the NOX or Duox enzymes. Such chemicals and drugs would likely be useful as treatments for the cellular proliferative disorders and diseases described above.

Accordingly it is an object of the invention to provide a transgenic non-human animal, which expresses NOX or Duox enzymes.

A further object of the invention is to provide a transgenic mouse which expresses NOX or Duox enzymes.

It is another object of the invention to provide DNA constructs encoding for NOX or Duox enzymes.

It is a further object of the invention to provide a non-human animal model system expressing NOX or Duox enzymes.

Yet another object of the invention is to provide a transgenic non-human animal comprising a transgene which encodes for NOX or Duox enzymes.

A further object of the invention is to provide a transgene comprising SEQ ID NO:1, SEQ ID NO:3, SEQ ID NO:5, SEQ ID NO:7, SEQ ID NO:9, SEQ ID NO:11 or SEQ ID NO:13.

Yet another object of the invention is to provide a transgene that encodes for SEQ ID NO:2, SEQ ID NO:4, SEQ ID NO:6, SEQ ID NO:8, SEQ ID NO:10, SEQ ID NO:12 or SEQ ID NO:14.

It is an additional object of the invention to provide a non-human animal model system to study the in vivo and in vitro regulation and effects of NOX and Duox enzymes in specific tissue types.

It is a further object of the invention to provide a non-human animal model system to examine the role of NOX and Duox proteins in the generation of ROI in specific tissues.

Yet another object of the invention is to provide a non-human animal model system to examine the role of Nox proteins, particularly NOX1 in colon tissue.

A further object of the invention is to provide a non-human animal model system which has a propensity for the development of pathological conditions related to cell growth and proliferation.

Another object of the present invention is to provide a non-human animal model system wherein the role of NOX and Duox-derived ROI on cell signaling in human and non-human animals may be examined in a tissue-specific manner.

It is yet another object of the invention to provide a transgenic animal useful for developing therapies for pathophysiological conditions characterized by abnormal cellular proliferation.

It is another object of the present invention to provide a method for screening compounds for use in treating and preventing cellular proliferation disorders, particularly cancer.

Other objects, advantages and features of the invention will become apparent upon consideration of the following detailed description of the invention.

BRIEF DESCRIPTION OF THE FIGURES

This patent contains at least one color photograph. The U.S. Patent and Trademark Office will provide copies of this patent with the color photographs upon request and payment of the necessary fee.

DETAILED DESCRIPTION OF INVENTION

Figure 1:
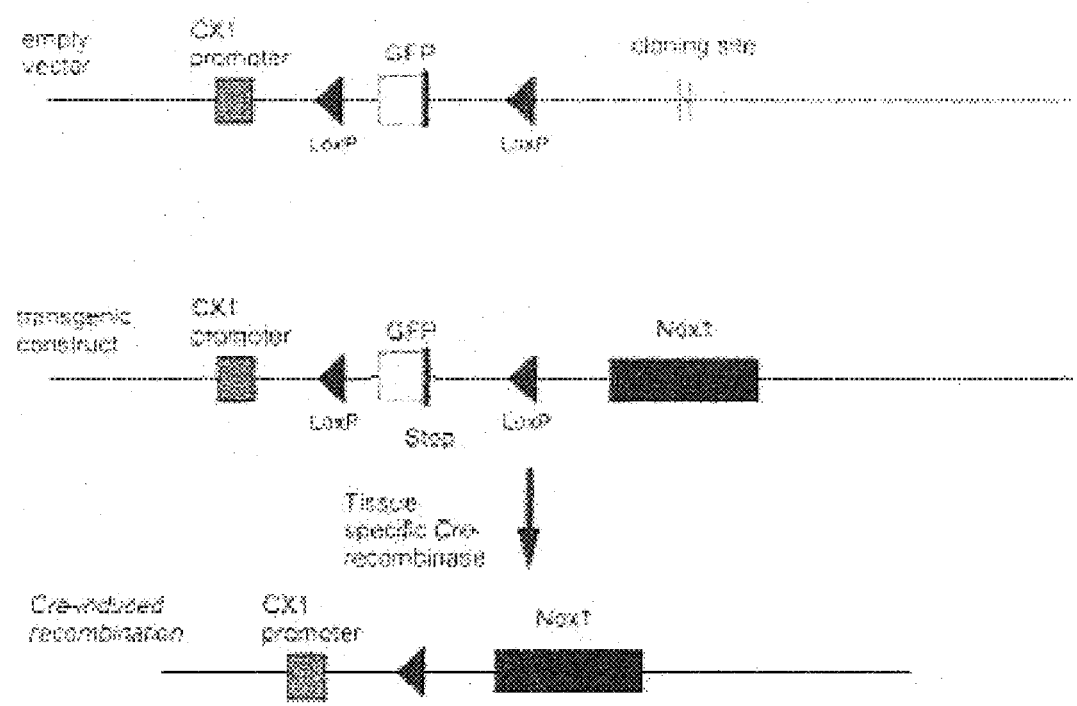
FIG. 1 is a diagram of the vector design for the development of conditional, tissue-specific NOX1 overexpressing transgenic mice.

The present invention provides a transgenic non-human animal, in particular a transgenic mouse, comprising a transgene encoding for a member of the NOX and Duox family of proteins. The present invention further comprises methods and compositions for evaluating regulators of abnormal cell growth. The present invention additionally comprises methods and compositions for the development of compounds, such as drugs or other therapies, for the treatment of conditions associated with abnormal cell growth, including, but not limited to, cancer, psoriasis, prostatic hypertrophy, benign prostatic hypertrophy, inflammatory bowel disease, cardiovascular disease, proliferation of vessels, including but not limited to blood vessels and lymphatic vessels, arteriovenous malformation, vascular problems associated with the eye, atherosclerosis, hypertension, and restenosis following angioplasty.

Reactive oxygen intermediates (ROI) generated in many non-phagocytic cells are now thought to originate from NOX or Duox enzymes. These enzymes are homologs of gp91phox, the catalytic subunit of the phagocyte NADPH oxidase. The NOX/Duox family consists, in humans, of 7 unique proteins NOX1 (SEQ ID NO:2), NOX2 (same as gp91phox) (SEQ ID NO:4), NOX3 (SEQ ID NO:6), NOX4 (SEQ ID NO:8), NOX5 (SEQ ID NO:10), Duox1 (SEQ ID NO:12) and Duox2 (SEQ ID NO:14). The sequences for the NOX and Duox family have been previously disclosed in WO/0028031, WO/0187957, and WO/02081703, each of which is incorporated by reference in its entirety.

Each of the NOX or Duox enzymes has a specific expression profile in different tissues. For example, NOX1 is highly expressed in colonic epithelium, while NOX4 is highly expressed in kidney epithelium. While not wishing to be bound to any particular theory, it is believed that the proteins related to gp91phox and involved in ROI generation in cells have been located in the NOX and Duox family of proteins. (Lambeth et al. (2001) *Gene* May 16; 269 (1–2):131–40; Edens et al (2001) *J. Cell Biol*. August 20: 154(4):879–91; Lambeth et al. (2000) *Trends Biochem Sci*. October 25, (10); 459–61).

Transgenes

A transgene is a segment of DNA that has been incorporated into a host genome or is capable of autonomous replication in a host cell and is capable of causing the expression of one or more cellular products. Exemplary transgenes provide the host cell, or animals developed therefrom, with a novel phenotype relative to the corresponding non-transformed cell or animal. The NOX or Duox polynucleotides comprising the transgene of the present invention include NOX or Duox cDNA and can also include modified NOX or Duox cDNA. As used herein, a "modification" of a nucleic acid can include one or several nucleotide additions, deletions, or substitutions with respect to a reference sequence. A modification of a nucleic acid can include substitutions that do not change the encoded amino acid sequence due to the degeneracy of the genetic code, or which result in a conservative substitution. Such modifications to the nucleic acids can correspond to variations that are made deliberately, such as the addition of a poly A tail, or variations which occur as mutations during nucleic acid replication.

Exemplary modifications of the NOX or Duox nucleotide sequences include sequences that correspond to homologs of the nucleotide sequences for NOX1 (SEQ ID NO:1), NOX2 (SEQ ID NO:3), NOX3 (SEQ ID NO:5), NOX4 (SEQ ID NO:7), NOX5 (SEQ ID NO:9), Duox 1 (SEQ ID NO:11), Duox 2 (SEQ ID NO:13), such as homologs of other species, including mammalian species such as mice, primates, including monkey and baboon, rats, rabbits, bovine, porcine, ovine, canine, feline, or other animal species. The corresponding NOX or Duox sequences of non-human species including, but not limited to, *C. elegans* and *Drosophila* can be determined by methods known in the art, such as by PCR or by screening genomic, cDNA or expression libraries.

As employed herein, the term "substantially the same nucleotide sequence" refers to DNA having sufficient identity to the reference polynucleotide, such that it will hybridize to the reference nucleotide under moderately stringent, or higher stringency, hybridization conditions. DNA having "substantially the same nucleotide sequence" as the reference nucleotide sequence can have at least 60%, at least 70%, at least 80%, at least 90%, or at least 95% identity with respect to the reference nucleotide sequence.

The phrase "moderately stringent hybridization" refers to conditions that permit a target-nucleic acid to bind a complementary nucleic acid. The hybridized nucleic acids will generally have at least about 60% identity, at least about 70% identity, at least about 80% identity, at least about 90% identity, or at least about 95% identity. Moderately stringent conditions are conditions equivalent to hybridization in 50% formamide, 5× Denhart's solution, 5× saline sodium phosphate EDTA buffer (SSPE), 0.2% SDS (Aldrich) at about 42° C., followed by washing in 0.2× SSPE, 0.2% SDS (Aldrich), at about 42° C.

High stringency hybridization refers to conditions that permit hybridization of only those nucleic acid sequences that form stable hybrids in 0.018M NaCl at about 65° C. For example, if a hybrid is not stable in 0.018M NaCl at about 65° C., it will not be stable under high stringency conditions, as contemplated herein. High stringency conditions can be provided, for example, by hybridization in 50% formamide, 5× Denhart's solution, 5× SSPE, 0.2% SDS at about 42° C., followed by washing in 0.1× SSPE, and 0.1% SDS at about 65° C.

Other suitable moderate stringency and high stringency hybridization buffers and conditions are well known to those of skill in the art and are described, for example, in Sambrook et al., Molecular Cloning: A Laboratory Manual, 2nd ed., Cold Spring Harbor Press, Plainview, N.Y. (1989); and Ausubel et al. (Current Protocols in Molecular Biology (Supplement 47), John Wiley & Sons, New York (1999)).

The amino acid sequences encoded by the transgenes of the present invention can be a NOX or Duox sequence, such as NOX1 (SEQ ID NO:2), NOX2 (same as gp91phox) (SEQ ID NO:4), NOX3 (SEQ ID NO:6), NOX4 (SEQ ID NO:8), NOX5 (SEQ ID NO:10), Duox1 (SEQ ID NO:12) and Duox2 (SEQ ID NO:14) or the NOX or Duox homologue from any species. The protein polypeptide sequence encoded by the transgene of the present invention can also be a fragment of the NOX or Duox amino acid sequence, so long as the fragment retains some or all of the function of the full-length NOX or Duox sequence. The sequence may also be a modified NOX or Duox sequence. Individual substitutions, deletions or additions, which alter, add or delete a single amino acid or a small percentage of amino acids (typically less than 10%, more typically less than 5%, more typically less than 1%). A "modification" of the amino acid sequence encompasses conservative substitutions of the amino acid sequence. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (O);
4) Arginine (R), Lysine (K);
5) Isoleucine (I), Leucine (L), Methionine (M), Valine (V); and
6) Phenylalanine (F), Tyrosine (Y), Tryptophan (W).

Other minor modifications are included within the sequence so long as the polypeptide retains some or all of the structural and/or functional characteristics of a NOX or Duox polypeptide. Exemplary structural or functional characteristics include sequence identity or substantial similarity, antibody reactivity, the presence of conserved structural domains such as RNA binding domains or acidic domains, and the ability to generate ROI.

DNA Constructs and Vectors

The invention further provides a DNA construct comprising the NOX transgene or Duox transgene as described above. As used herein, the term "DNA construct" refers to a specific arrangement of genetic elements in a DNA molecule. In addition to human NOX or Duox, or mutant forms thereof, the invention also provides DNA constructs comprising NOX or Duox polypeptides from other species, as well as NOX or Duox mutant non-human mammals expressing NOX or Duox from non-human species. The constructs further comprise a promoter or other regulatory element such as lox-P, and may additionally comprise a reporter or marker element such as green enhanced fluorescent protein (EGFP).

If desired, the DNA constructs can be engineered to be operably linked to appropriate expression elements such as promoters or enhancers to allow expression of a genetic element in the DNA construct in an appropriate cell or tissue, for example, a colon epithelial cell-specific promoter or a prostate epithelial cell-specific promoter. Cell and tissue specific promoters are known to one of skill in the art. In one embodiment, the DNA construct may comprise a NOX or Duox polynucleotide sequence located upstream from two LoxP sites that comprise a "flox stop cassette." Specific, non-limiting examples of loxP include, but are not limited to, the sequence listed as Genbank accession No. M10494.1; LOX P (Genbank Accession No. U51223, herein incorporated by reference); LOX 511 (Bethke and Sauer, Nuc. Acid. Res. 25:282–34, 1997); ψLOXh7q21 (Thyagarajan et al., Gene, 244:47–54, 2000), ψCoreh7q21 (Thyagarajan et al., Gene, 244:47–54, 2000) as well as the Lox sites disclosed in Table 1 of Thyagarajan et al. (Gene, 244:47–54, 2000). Each loxP site corresponds to a 34 bp sequence, consisting of two 13-bp palindromic sequences with an 8 bp central core.

Within the "flox stop cassette" is located an EGFP gene sequence or other markers. Located upstream from the "flox stop cassette" is a tissue-specific promoter (such as a CX1 promoter). The use of the "flox stop cassette" and similar expression control mechanisms allows for the targeted delivery and expression of the gene of interest.

The DNA constructs described herein may be incorporated into vectors for propagation, or transfection into appropriate cells to generate NOX or Duox mutant non-human mammals. The DNA constructs may also be incorporated into vectors for transfection into appropriate cells for the development of cell cultures. One skilled in the art can select a vector based on desired properties, for example, for production of a vector in a particular cell such as a mammalian cell or a bacterial cell.

The invention also provides vectors containing a NOX or Duox encoding polynucleotide sequence. Suitable expression vectors are well-known in the art and include vectors capable of expressing nucleic acids operably linked to a regulatory sequence or element, such as a promoter region or enhancer region, that is capable of regulating expression of such nucleic acids. Appropriate expression vectors include those that are replicable in eukaryotic cells and/or prokaryotic cells and those that remain episomal or those that integrate into the host cell genome and are known to one of ordinary skill in the art. For example, NOX1 with SV40 poly A can be subcloned into the HindII and Sac I sites of a vector containing a CX1 promoter.

Vectors can contain a regulatory element that provides tissue specific or inducible expression of an operably linked nucleic acid. One of ordinary skill in the art can readily determine an appropriate tissue-specific promotor or enhancer that allows expression of NOX or Duox polypeptides in a desired tissue. It should be noted that tissue-specific expression as described herein does not require a complete absence of expression in tissues other than the preferred tissue. Instead, "cell-specific" or "tissue-specific" expression refers to a majority of the expression of a particular gene of interest in the preferred cell type or tissue.

Any of a variety of inducible promoters or enhancers can also be included in the vector for expression of a NOX or Duox polypeptide or nucleic acid that can be regulated. Such inducible systems are known to one of ordinary skill in the art and include, for example, a tetracycline inducible system (Gossen & Bizard, Proc. Natl. Acad. Sci. USA, 89:5547–5551 (1992); Gossen et al., Science, 268:1766–1769 (1995); Clontech, Palo Alto, Calif.); metalothionein promoter induced by heavy metals; insect steroid hormone systems responsive to ecdysone or related steroids such as muristerone (No et al., Proc. Natl. Acad. Sci. USA, 93:3346–3351 (1996); Yao et al., Nature, 366:476–479 (1993); Invitrogen, Carlsbad, Calif.); mouse mammary tumor virus (MMTV) induced by steroids such as glucocorticoid and estrogen (Lee et al., Nature, 294:228–232 (1981); and, heat shock promoters inducible by temperature changes.

Regulatory elements, including promoters or enhancers, can be constitutive or regulated, depending upon the nature of the regulation, and can be regulated in a variety of tissues, a few specific types of tissues, or a single tissue type. The regulatory sequences or regulatory elements are operably linked to one of the polynucleotide sequences of the invention such that the physical and functional relationship between the polynucleotide sequence and the regulatory sequence allows transcription of the polynucleotide sequence. Vectors useful for expression in eukaryotic cells can include, for example, regulatory elements including the SV40 early promoter, the cytomegalovirus (CMV) promoter, the mouse mammary tumor virus (MMTV) steroid-inducible promoter, Moloney murine leukemia virus (MMLV) promoter, CX1 promoter and the like.

If desired, the vector can contain a selectable marker. As used herein, a "selectable marker" refers to a genetic element that provides a selectable phenotype to a cell in which the selectable marker has been introduced, such as the fluorescence of the EGFP protein. A selectable marker is generally a gene whose gene product provides resistance to an agent that inhibits cell growth or kills a cell. A variety of selectable markers, generally known to one of ordinary skill in the art, can be used in the DNA constructs of the invention, including, for example, Neo, Hyg, hisD, Gpt and Ble genes, as described, for example in Ausubel et al. (Current Protocols in Molecular Biology (Supplement 47), John Wiley & Sons, New York (1999)) and U.S. Pat. No. 5,981,830. Drugs useful for selecting for the presence of a selectable marker include, for example, G418 for Neo, hygromycin for Hyg, histidinol for hisD, xanthine for Gpt, and bleomycin for Ble (see Ausubel et al., supra, (1999); U.S. Pat. No. 5,981,830). DNA constructs of the invention can incorporate a positive selectable marker, a negative selectable marker, or both (see, for example, U.S. Pat. No. 5,981,830).

Non-Human Transgenic Animals

The present invention provides a nonhuman transgenic animal whose genome comprises a transgene encoding a NOX or Duox polypeptide. The transgene can be integrated into the genome of a transgenic animal by any method known to those skilled in the art. The transgene containing the desired gene sequence can be introduced into pluripotent cells, such as embryonic stem (ES) cells, by any method that will permit the introduced molecule to undergo recombination at its regions of homology. Techniques that can be used include, but are not limited to, calcium phosphate/DNA co-precipitates, microinjection of DNA into the nucleus, electroporation, bacterial protoplast fusion with intact cells, transfection, and polycations, (e.g., polybrene, polyornithine, etc.) The DNA can be single or double stranded DNA, linear or circular. (See for example, Hogan et al., Manipulating the Mouse Embryo: A Laboratory Manual Cold Spring Harbor Laboratory (1986); Hogan et al., Manipulating the Mouse Embryo: A Laboratory Manual, second ed., Cold Spring Harbor Laboratory (1994), U.S. Pat. Nos. 5,602,299; 5,175,384; 6,066,778; 4,873,191 and 6,037,521; retrovirus mediated gene transfer into germ lines (Van der Putten et al., Proc. Natl. Acad. Sci. USA 82:6148–6152 (1985)); gene targeting in embryonic stem cells (Thompson et al., Cell 56:313–321 (1989)); electroporation of embryos (Lo, Mol Cell. Biol. 3:1803–1814 (1983)); and sperm-mediated gene transfer (Lavitrano et al., Cell 57:717–723 (1989))).

For example, the zygote is a good target for microinjection, and methods of microinjecting zygotes are well known to those of skill in the art (see U.S. Pat. No. 4,873,191). In the mouse, the male pronucleus reaches the size of approximately 20 micrometers in diameter, which allows reproducible injection of 1–2 picoliters (pl) of DNA solution. The use of zygotes as a target for gene transfer has a major advantage in that in most cases the injected DNA will be incorporated into the host genome before the first cleavage (Brinster, et al, Proc. Natl. Acad. Sci. USA 82:4438–4442 (1985)). As a consequence, all somatic cells of the transgenic non-human animal will carry the incorporated transgene. This will in general, also be reflected in the efficient transmission of the transgene to offspring of the founder since 50% of the germ cells will harbor the transgene. The injected zygotes are transplanted to the oviducts/uteri of pseudopregnant females and finally transgenic animals are obtained.

Embryonal cells at various developmental stages can be used to introduce transgenes for the production of transgenic animals. Different methods are used depending on the stage of development of the embryonal cell. Such transfected embryonic stem (ES) cells can thereafter colonize an embryo following their introduction into the blastocoele of a blastocyst-stage embryo and contribute to the germ line of the resulting chimeric animal (reviewed in Jaenisch, Science 240:1468–1474 (1988)). Prior to the introduction of transfected ES cells into the blastocoele, the transfected ES cells can be subjected to various selection protocols to enrich the proportion of ES cells that have integrated the transgene if the transgene provides a means for such selection. Alternatively, PCR can be used to screen for ES cells that have integrated the transgene.

Retroviral infection can also be used to introduce transgenes into a non-human animal. The developing non-human embryo can be cultured in vitro to the blastocyst stage. During this time, the blastomeres can be targets for retroviral infection (Janenich, Proc. Natl. Acad. Sci. USA 73:1260–1264 (1976)). Efficient infection of the blastomeres is obtained by enzymatic treatment to remove the zona pellucida (Hogan et al., supra, 1986). The viral vector system used to introduce the transgene is typically a replication-defective retrovirus carrying the transgene (Jahner et al., Proc. Natl. Acad. Sci. USA 82:6927–6931 (1985); Van der Putten et al., Proc. Natl. Acad. Sci. USA 82:6148–6152 (1985)). Transfection is easily and efficiently obtained by culturing the blastomeres on a monolayer of virus-producing cells (Van der Putten, supra, 1985; Stewart et al., EMBO J. 6:383–388 (1987)). Alternatively, infection can be performed at a later stage. Virus or virus-producing cells can be injected into the blastocoele (Jahner D. et al., Nature 298:623–628 (1982)). Most of the founders will be mosaic for the transgene since incorporation occurs only in a subset of cells which form the transgenic animal. Further, the founder can contain various retroviral insertions of the transgene at different positions in the genome, which generally will segregate in the offspring. In addition, transgenes may be introduced into the germline by intrauterine retroviral infection of the midgestation embryo (Jahner et al., supra, 1982). Additional means of using retroviruses or retroviral vectors to create transgenic animals known to those of skill in the art involves the microinjection of retroviral particles or mitomycin C-treated cells producing retrovirus into the perivitelline space of fertilized eggs or early embryos (WO 90/08832 (1990); Haskell and Bowen, Mol. Reprod. Dev. 40:386 (1995)).

Once the founder animals are produced, they can be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic mice to produce mice homozygous for a given integration site in order to both augment expression and eliminate the need for screening of animals by DNA analysis; crossing of separate homozygous lines to produce compound heterozygous or homozygous lines; breeding animals to different inbred genetic backgrounds so as to examine effects of modifying alleles on expression of the transgene and the effects of expression.

Crossbreeding of the transgenic mice can also allow for tissue specific expression of the transgene. Thus, while the NOX1 gene would exist in all somatic cells of the transgenic animal, expression of the NOX1 protein could be localized to, for example, the colon.

An example of a crossbreeding strategy for effecting tissue specific expression of NOX or Duox is through the use of the target recombining site sequence recognized by the bacterial Cre recombinase (Cre) which is available in mouse lines which have been previously developed to express Cre in a tissue specific manner. Homologous recombination is used to insert loxP DNA sites into inactive regions of DNA flanking a marker EGFP gene and its associated stop sequence in the empty vector. NOX or Duox is then cloned into the empty vector upstream of the 3' loxP site to create a transgenic construct which is used to create a transgenic mouse. The resulting NOX or Duox mice are then crossed with Fabp14× at −132/Cre-mice hemizygous for Fabp14× at −132/Cre (Cre mice) (Saam, J. Biological Chemistry, 274:38071–38082 1999)(a gift from Jeffery I. Gordon (Washington University School of Medicine)). The Cre mice contain: (i) Fabp14× at −132 (nucleotides −596 to +21 of the rat Fabpl gene, with four additional tandem repeats of its nucleotides −172 to −133 added at nucleotide −132) linked to (ii) a 1.0 kb fragment, containing the Cre recombinase gene with a nuclear localization signal from SV40 large T antigen (from Gail Martin, University of California, San Francisco), and (iii) nucleotides +3 to +2150 of the human growth hormone gene (hGH). The P1 bacteriophage derived enzyme, Cre recombinase, then catalyzes recombination between the two loxP sites, resulting in the excision of the reporter EGFP and its associated stop sequence. The loss of EGFP and its corresponding fluorescence in the transgenic offspring serves to verify Cre-mediated excision of the EGFP stop sequence; the excision of the stop sequence allows NOX or Duox to be expressed in the tissues of the transgenic mice. When the two mouse lines are crossed, offspring are generated in which the gene of interest is overexpressed when the promoter of the gene used to confer expression is normally activated.

Figure 3A:
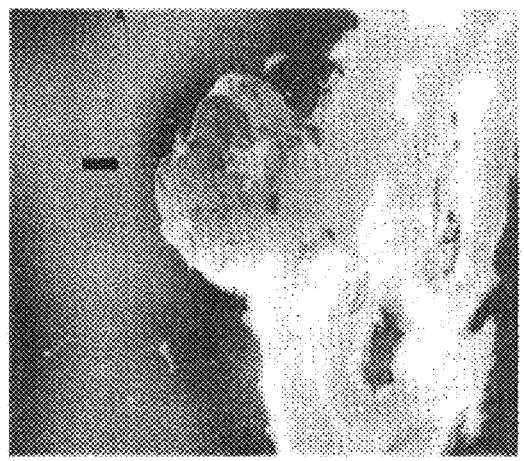
FIG. 3: (A) is a photograph of one of two tumors found in the colon of an $Apc^{min}$/h-NOX1 mouse; (B–D) are photographs of histological analyses of the tumor shown in (A) by hematoxylin and eosin staining; (E) is a photograph of the adjacent section of normal colon.
Figure 3B:
Figure 3C:
Figure 3D:
Figure 3E:
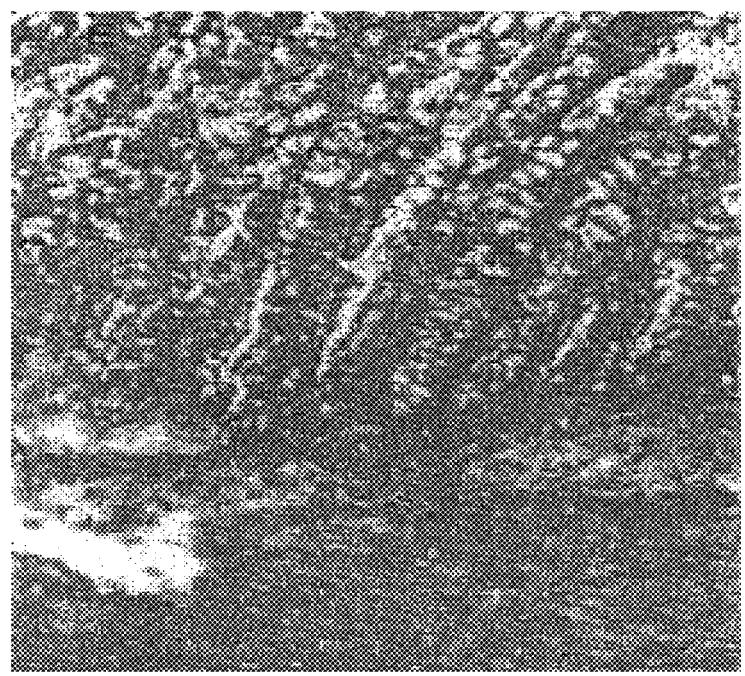

To increase expression, or development of a particular disease or condition, a mouse overexpressing Nox1, such as the offspring of two crossed mouse lines such as the Cre/NOX1 mouse described above, can be further crossed with mice that have a proclivity to particular disease states. For example, the NOX overexpressing mice of the present invention were crossed with the multiple intestinal neoplasia (Min) mouse. The Min mouse is available commercially from Jackson Labs, Bar Harbor, Me. Heterozygous Min mice show multiple gastrointestinal neoplasias, mainly small flat polyps in the small intestine. The mutation in the Min mouse is a nonsense mutation in codon 850 of the murine adenomatous polyposis coli (APC) tumor suppressor gene. The Min and Cre/NOX1 cross produced mice that developed colon tumors by 100 days. The Cre/NOX1/Min crossed mouse produced several large (0.5 cm) carcinomas protruding into the lumen of the colon (See FIGS. 3 and 3A). The Min/Cre/NOX1 cross is therefore a novel model for colon cancer. Other suitable mice lines specific for particular diseases or conditions are known to those of skill in the art. The present invention provides transgenic non-human mammals that carry the transgene in all their cells, as well as animals that carry the transgene in some, but not all their cells, that is, mosaic animals.

Figure 2A:
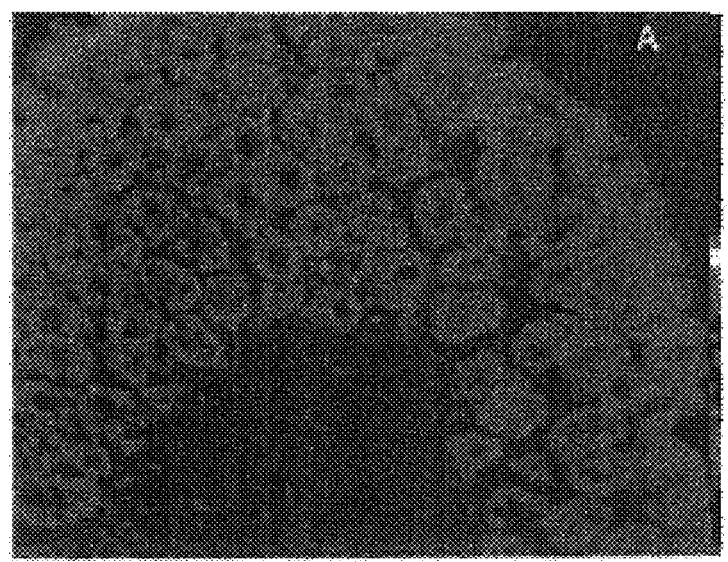
FIG. 2: (A) is a photograph of dihydroethidium fluorescence in a cross-section of the colon of a wild type Black/6 mouse; (B) is a photograph of dihydroethidium fluorescence in a cross-section of the colon of a hNOX1 expressing B1/6 mouse.
Figure 2B:
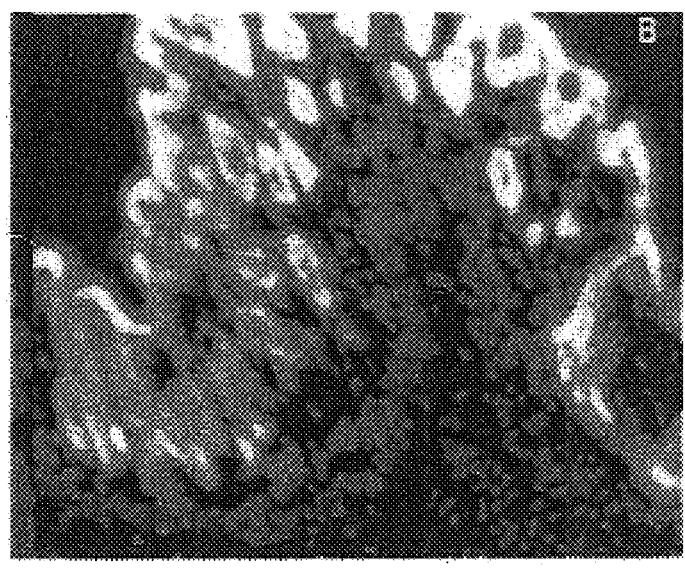

The transgenic animals are screened and evaluated to select those animals having the phenotype of interest. Initial screening can be performed using, for example, Southern blot analysis or PCR techniques to analyze animal tissues to verify that integration of the transgene has taken place. The level of mRNA expression of the transgene in the tissues of the transgenic animals can also be assessed using techniques which include, but are not limited to, Northern blot analysis of tissue samples obtained from the animal, in situ hybridization analysis, and reverse transcriptase-PCR (rt-PCR). Samples of the suitable tissues can be evaluated immunocytochemically using antibodies specific for a NOX or Duox as appropriate, or with a tag such as EGFP. The transgenic non-human mammals can be further characterized to identify those animals having a phenotype useful in methods of the invention. In particular, transgenic non-human mammals overexpressing NOX or Duox can be screened using the methods disclosed herein. For example, tissue sections can be viewed under a fluorescence microscope for the present of fluorescence, indicating the presence of the reporter gene. (See FIGS. 2A and 2B).

Another method for affecting tissue specific expression of the NOX or Duox proteins is through the use of tissue-specific promoters. Non-limiting examples of suitable tissue-specific promoters include the albumin promoter (liver-specific; Pinkert et al., (1987) Genes Dev. 1:268–277), lymphoid-specific promoters (Calame and Eaton (1988) Adv. Immunol. 43:235–275), in particular promoters of T cell receptors (Winoto and Baltimore (1989) EMBO J. 8:729–733) and immunoglobulins (Banerji et al., (1983) Cell 33:729–740; Queen and Baltimore (1983) Cell 33:741–748), neuron-specific promoters (e.g., the neurofilament promoter; Byrne and Ruddle (1989) PNAS 86:5473–5477), pancreas-specific promoters (Edlund et al., (1985) Science 230:912–916), cardiac specific expression (alpha myosin heavy chain promoter, Subramaniam, et al., J Biol Chem 266: 24613–24620, 1991), and mammary gland-specific promoters (e.g., milk whey promoter; U.S. Pat. No. 4,873,316 and European Patent Application Publication No. 264,166).

The invention further provides an isolated cell containing a DNA construct of the invention. The DNA construct can be introduced into a cell by any of the well-known transfection methods (Sambrook et al., Molecular Cloning: A Laboratory Manual, 2nd ed., Cold Spring Harbor Press, Plainview, N.Y. (1989); Ausubel.et al., supra, (1999)). Alternatively, the cell can be obtained by isolating a cell from a mutant non-human mammal created as described herein. Thus, the invention provides a transfected cell or a cell isolated from a NOX or Duox mutant non-human mammal of the invention, in particular, a NOX or Duox mutant mouse. The cells can be obtained from a homozygous NOX or Duox mutant mouse or a heterozygous NOX or Duox mutant non-human mammal such as a mouse.

Assays and Identification of Therapeutic Agents

The methods and compositions of the present invention are particularly useful in the evaluation of regulators of NOX or Duox enzymes and for the development of drugs and therapeutic agents for the treatment and prevention of cancer, particularly in blocking the progression of polyps to a cancerous stage. The methods and composition of the present invention are particularly useful for the development of drugs and therapeutic agents for the treatment of colon cancer.

Compounds useful as potential therapeutic agents can be generated by methods well known to those skilled in the art, for example, well known methods for producing pluralities of compounds, including chemical or biological molecules such as simple or complex organic molecules, metal-containing compounds, carbohydrates, peptides, proteins, peptidomimetics, glycoproteins, lipoproteins, nucleic acids, antibodies, and the like, are well known in the art and are described, for example, in U.S. Pat. No. 5,264,563; Francis et al., Curr. Opin. Chem. Biol. 2:422–428 (1998); Tietze et al., Curr. Biol., 2:363–371 (1998); Sofia, Mol. Divers. 3:75–94 (1998); Eichler et al., Med. Res. Rev. 15:481–496 (1995); the National Cancer Institute Database, and the like. Libraries containing large numbers of natural and synthetic compounds also can be obtained from commercial sources. Combinatorial libraries of molecules can be prepared using well known combinatorial chemistry methods (Gordon et al., J. Med. Chem. 37: 1233–1251 (1994); Gordon et al., J. Med. Chem. 37: 1385–1401 (1994); Gordon et al., Acc. Chem. Res. 29:144–154 (1996); Wilson and Czarnik, eds., Combinatorial Chemistry: Synthesis and Application, John Wiley & Sons, New York (1997)).

The transgenic animal, cells from the transgenic animal, or cells transfected in vitro with the transgenes of the present invention can be used in a variety of screening assays. For example, any of a variety of potential agents suspected of causing or contributing to cellular proliferation, hyperplasia and inflammation, as well as the appropriate antagonists and blocking therapeutic agents, can be evaluated by administration to the transgenic animal, cells of the transgenic animal, or transfected cells, and assessing the effect of these agents upon the function and phenotype of the cells. The compounds can increase, decrease or fail to alter the cellular proliferation, hyperplasia or inflammation.

The methods of the invention advantageously use cells isolated from a homozygous or heterozygous NOX or Duox mutant non-human mammal, for example, endothelial cells, epithelial cells, or muscle cells to study the regulatory mechanisms of ROI production and cellular proliferation, and to test potential therapeutic compounds. The methods of the invention are also used with cells expressing NOX or Duox such as a transfected cell line.

A cell overexpressing NOX or Duox can be used in an in vitro method to screen compounds as potential therapeutic agents for treating cellular proliferative disorders or other disorders involved in ROI production. In such a method, a compound is contacted with a cell overexpressing NOX or Duox, either a transfected cell or a cell derived from a NOX or Duox mutant non-human animal, and screened for alterations in a phenotype associated with expression of NOX or Duox. For example, the administration of the compound at a dose or level known to one of skill in the art, can increase cellular proliferation, decrease cellular proliferation or leave it unchanged. The compound can additionally specifically increase ROI production, decrease ROI production or have no effect. The changes in ROI production and cellular proliferation in the cellular assay and the transgenic animal can be assessed by methods well known to those skilled in the art.

A NOX or Duox fusion polypeptide such as NOX1-EGFP is particularly useful for such screening methods since the expression of NOX or Duox can be monitored by fluorescence intensity. Other exemplary fusion polypeptides include other fluorescent proteins, or modifications thereof, glutathione S transferase (GST), maltose binding protein, poly His, and the like, or any type of epitope tag. Such fusion polypeptides are detected, for example, using antibodies specific to the fusion polypeptides. The fusion polypeptides can be an entire polypeptide or a functional portion thereof so long as the functional portion retains desired properties, for example, antibody binding activity or fluorescence activity.

Additionally, the level or activity of the NOX or Duox proteins expressed by the transgenes of the present invention, including the activity of the proteins in response to the addition of potential therapeutic agents, are measured by methods which include, but are not limited to, cytochrome c reduction, Nitroblue tetrazolium reduction, and luminesence.

The invention further provides a method of identifying a potential therapeutic agent for use in treating cellular proliferative disorders such as cancer, particularly colon cancer. The method includes the steps of contacting a cell containing a DNA construct comprising polynucleotides encoding a NOX or Duox polypeptide with the potential therapeutic agent and screening the cell for decreased NOX or Duox production or enzymatic activity, thereby identifying a potential therapeutic agent for use in treating a cellular proliferative disease. The cell can be isolated from a transgenic non-human animal having nucleated cells containing the NOX or Duox DNA construct. The cell can also contain a DNA construct comprising a nucleic acid encoding a green fluorescent protein fusion, or other fusion polypeptide, with a NOX or Duox polypeptide.

Additionally, cells expressing a NOX or Duox polypeptide can be used in a preliminary evaluation to identify compounds as potential therapeutic agents having activity that alters a phenotype associated with NOX or Duox expression. As with in vivo screens using NOX or Duox mutant non-human mammals, an appropriate control cell is used to compare the results of the evaluation. The effectiveness of compounds identified by an initial in vitro evaluation using cells expressing NOX or Duox is further tested in vivo using the NOX or Duox mutant non-human mammals of the present invention, if desired. Thus, the invention provides methods of screening a large number of compounds using a cell-based assay, for example, using high throughput screening, as well as methods of further testing compounds as therapeutic agents in an animal model of cellular proliferative disorders. Additionally, the cellular proliferative conditions being treated can be aggravated, for example, by the addition of an inflammatory agent such as *C. rodentium* to further analyze the effectiveness of the potential therapeutic agents.

Compounds identified as therapeutic agents by methods of the invention are administered to an individual, for example, to prevent, inhibit or reverse cellular proliferation. One skilled in the art will know or can readily determine the alleviation of a sign or symptom associated with cellular proliferative disorders such as cancer.

For use as a therapeutic agent, the compound is formulated with a pharmaceutically acceptable carrier to produce a pharmaceutical composition, which is administered to a human or other animal. Pharmaceutically acceptable carriers are known to one of ordinary skill in the art and include, but are not limited to, water, sodium phosphate buffer, phosphate buffered saline, normal saline, physiological buffer, Ringer's solution or other physiologically buffered saline, another solvent or vehicle such as a glycol or glycerol, an oil such as olive oil, or an injectable organic ester. A pharmaceutically acceptable carrier can also contain physiologically acceptable compounds that act, for example, to stabilize or increase the absorption of the therapeutic agent. One skilled in the art knows that the choice of a pharmaceutically acceptable carrier, including a physiologically acceptable compound, depends, for example, on the route of administration of the composition.

All publications and patents mentioned herein are incorporated by reference in their entireties for the purpose of describing and disclosing, the constructs and methodologies which might be used in connection with the present invention. The above disclosure generally describes the present invention. A more complete understanding can be obtained by reference to the following examples. These examples are described solely for purposes of illustration and are not intended to limit the scope of the invention. Although specific terms have been employed herein, such terms are intended in a descriptive sense and not for purposes of limitation.

EXAMPLE 1

Construction of Transgenic Mice

The NOX1 transgenic plasmid, human full-length cDNA of NOX1 (SEQ ID NO: 1) with SV40 poly A, was subcloned into HindIII and SacI sites of a vector containing a CX1 promoter, and LoxP-flanked enhanced green fluorescent protein (EGFP) gene cassette (a gift of Dr. Kathy Griendling). In this construct, NOX1 cDNA is located at the 3' end of the LoxP-flanked EGFP cassette. Before pronuclear injection, the NOX1 transgenic plasmid was digested with XhoI to release the cassette containing the CX1 promoter, the LoxP-flanked enhanced green fluorescent protein (EGFP) gene, and NOX1 cDNA. Pronuclear injection was conducted at the Transgenic Mice Core Facility at Emory University. Two lines of C57BL/6J mice containing the NOX1 transgene were created and verified by Southern Blot and PCR (see following).

EXAMPLE 2

Verification of Mouse Pedigree Using a $P^{32}$-labeled 792 bp fragment of NOX1 cggttttaccgctcccagcagaaggt-tgtgattaccaaggttgttatgcacccatccaaagttttggaattgcagat gaa-caagcgtggcttcagcatg-gaagtggggcagtatatctttgttaattgccctcaatctctctcctggaatgg catccttttactttgacctctgctcca-gaggaagatttcttctccattcatatccgagcagcaggggactggacaga aaatctcataagggctttcgaacaa-caatattcaccaattcccaggattgaagtggatggtccctttggcacagcc agt-gaggatgttttccagtatgaagtggct-gtgctggttggagcaggaattggggtcaccccctttgcttctatctt gaaatccatctggtacaaattccagtgt-gcagaccacaacctcaaaacaaaaaagatctatttctactggatctgc agggaga-caggtgccttttcctggttcaacaacct-gttgacttccctggaacaggagatggaggaattaggcaa agtgggttttctaaactaccgtctcttc-ctcaccggatgggacagcaatattgttggtcatgcagcattaaactttga caaggc-cactgacatcgtgacaggtctgaaaca-gaaaacctcctttgggagaccaatgtgggacaatgagtttt ctacaatagctacctcccacoc-caagtctgtagtgggagttttcttatgtggccctcggactttggcaaagagcct gcgcaaatgctgtcaccgatattccagtctggatcc (SEQ ID NO: 15) Southern Blot was carried out using standard procedures to determine the copy numbers of trans-NOX1 gene. (See, e.g., Sambrook, J., Fritsch, E. F.; Maniatis, T.; "Molecular Cloning: a laboratory manual"; Cold Spring Harbor Laboratory Press). Briefly, 30 μg of genomic DNA from tail bits were digested overnight with 400 units of BamHI. In addition, 2 μg of the transgenic vector containing Nox1 DNA (SEQ ID NO:1) was digested with 40 units of BamHI and amounts containing 1, 5, 10, 20, and 100 copies of Nox1 (SEQ ID NO: 1) were loaded along with 10 ug of carrier wildtype mouse DNA onto the same gel as the Nox1 transgenic mice DNA. The resultant fragments were then separated on a 0.7% agarose gel by means of overnight electrophoresis and then transferred overnight by means of a capillary blot to nitrocellulose. To ensure efficient transfer of the DNA fragments to the nitrocellulose, the gel was stained with 10 mg/ml ethidium bromide following the transfer. 2 μg of the transgenic vector containing Nox1 DNA was digested with 40 units of BamHI and amounts containing 1, 5, 10, 20, and 100 copies of Nox1 were loaded along with 10 ug of carrier wildtype mouse DNA. Hybridization was performed using the $P^{32}$-labeled 792 bp fragment of NOX1 as a probe. Following hybridization, the membrane was washed once with 500 ml 2× SSPE, 1% SDS for 25 minutes at room temperature and then three times with pre-heated 0.2× SSPE, 0.2% SDS for 20 minutes at 65° C. to 68° C. before exposure to X-ray film. One NOX1 transgenic mouse contained one copy while another contained 20 copies.

EXAMPLE 3

Cross Breeding of NOX1 Mice and Cre Mice

Fabp14× at −132/Cre-CX1/(loxP)-hNOX1-Bi-transgenic mice were produced by crossing hemizygous C57BL/6J CX1/(loxP)EGFP(loxP)-hNOX1 mice with hemizygous FVB/N Fabp14× at −132/Cre mice. Two pedigrees of Fabp14× at −132/Cre/CX1/(loxP)-hNOX1 were used.

EXAMPLE 4

Maintenance of Transgenic Mice

All mice used in these examples were housed in microisolator cages under a strict light cycle (lights on at 0700 h and off at 1900 h). Mice were given a standard irradiated chow diet (Rodent diet 5001, Labdiet® Richmond, Ind.) ad libitum. Animals were maintained in a specified pathogen-free state. All C57BL/6J and FVB/N mice were hemizygous for their respective transgenes.

EXAMPLE 5

Identification of Transgenic Mice

Genomic DNA was extracted from tail bits of 21 day old mice and used to identify the crossbred mice positive or negative for hNOX1 and or Fabp1-Cre using PCR. hNOX1 DNA sequences were identified using primer 1,5'-GTG AGG ATG TTT TCC AGT ATG AAG (SEQ ID NO:16) and primer 2,5'-TGT CAA AGT TTA ATG CTG CAT GAC CA (SEQ ID NO:17). Cycle conditions were 95.0° C. for 1 min 30 sec, 35 cycles of 95.0° C. for 30 sec, 62.0° C. for 20 sec, 72.0° C. for 45 sec, and a final extension of 72.0° C. for 3 min. These primers produce a 300 bp amplicon. The amplicons were visualized on a 1.5% agarose gel.

Fabp1-Cre was detected using forward and reverse primers CreF (5'-AAC TGA AGA TGT TCG CGA TTA TCT (SEQ ID NO:18) and CreR (5'-ACC GTC AGT ACG TGA GAT ATC TT (SEQ ID NO:19) Cycle conditions were: 94.0° C. for 6 min, 40 cycles of 94.0° C. for 1 min, 54.0° C for 30 sec, 72.0° C. for 30 sec, and a final extension of 72.0° C. for 7 min. These primers produce a 350 bp amplicon in Fabp1-cre transgenic mice. The amplicons were visualized on a 1.5% agarose gel.

EXAMPLE 6

EGFP Reporter Gene Assay

Sections (6 μm) from colon, spleen, brain, liver, kidney, small intestine, and muscle from wildtype mice and mice identified in Example 5 as positive for the hNOX1 transgene were viewed on a Nikon eclipse TS-100 fluorescent microscope using a Nikon (FITC) filter (B-2E/C). Wildype tissue sections and their respective hNOX1 transgene sections were compared for the presence of fluorescence. (See FIGS. 2A and 2B)

EXAMPLE 7

Immunohistochemistry

Figure 4:
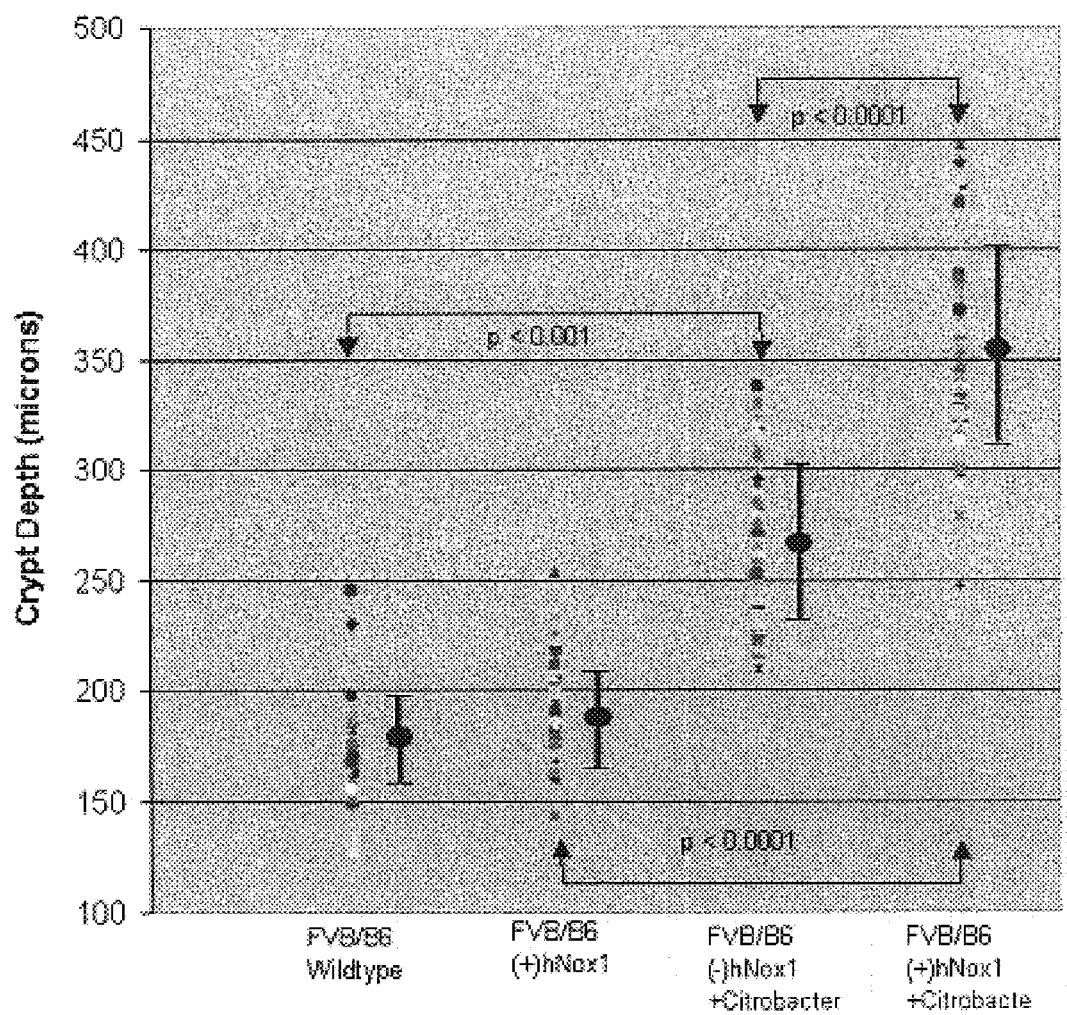
FIG. 4 is a graph of colon crypt pit to tip depth of NOX1 overexpressing mice exposed to *Citrobacter rodentium* (*C. Rodentium*).

Freshly harvested tissue was embedded in TBS (Triangle Biomedical Sciences, Durham, N.C.) tissue freezing medium. A cyrostat was then used to make semi-thin (5–10

μm) sections of the embeded tissue. The tissue sections were fixed in 2% paraformaldehyde in 1× PBS and placed at 4° C. for 30 min. The sections were then washed 2 times in 1× PBS. (5 min/wash). Wet paper towels were layered in the base of moist chamber and the slides were placed in the chamber and allowed to reach room temperature. Before the slides dried, they were layered with 50 μl 1× PBS. Blocking was performed using 1% normal goat serum or 2% BSA and 0.1% Triton in PBS for 1 hour. The primary antibody (a polyclonal antibody raised in rabbit against hNOX1, Lampire Biological Laboratories, Inc.) was centrifuged for 2 min at 13,500 rpm at 4° C. and diluted in wash buffer (0.1% Triton in 1× PBS) at 1:100. The PBS was removed by aspirating at one end of the section and introducing antibody solution at the opposite end. The slides were then incubated for 1–2 hr, at room temperature. The slides were washed 3 times in 1× PBS (5 min/wash). The secondary antibody (goat anti-rabbit IgG Alexa Fluor 555 fluorescent antibody, Molecular Probes) was centrifuged for 2 min; 13,500 rpm at 4° C. and diluted in wash buffer at 1:1000. 50 μl of the antibody/wash buffer solution was used to cover the sections on each slide. The slides were then incubated in a moist chamber for 1 hr at room temperature. Next, the slides were washed 3 times in 1× PBS (5 min/wash). The slides were mounted with Gelvatol and allowed to dry before viewing on a confocal microscope. Crypt depth (from base of crypt to tip of crypt) was measured by micrometry on sections of the distal-rectal region of mouse colon stained with H&E. The measures of ten well-oriented crypts per animal were recorded prior to and after exposure to cryptobacter as detailed in Example 10, below. Measurements were taken before genotyping of the animal. (See FIG. 4)

EXAMPLE 8
RNA extraction and RT-PCR

Freshly dissected tissues were taken and RNA was isolated using TRIzol Reagent Total RNA Isolation Reagent (GibcoBRL; Protocols outlined in http://microarray.mbg.jhmi.edu/Trizol.pdf). For RT-PCR, cDNA was synthesized using Advantage RT-for-PCR Kit (Clontech). A 20 μl reaction mixture containing Moloney-Murine Leukemia Virus, recombinant (MMLV) reverse transcriptase (Clontech, Palo Alto, Calif.) and random hexamer primer mix (Clontech, Palo Alto, Calif.) was used for the synthesis reaction. PCR was performed using 1 μl of the above synthetic cDNA with primer 1 (SEQ ID NO:16) and primer 2 (SEQ ID NO:17). The thermocyler program was: 95.0° C. for 1 min 30 sec, 35 cycles of 95.0° C. for 30 sec, 62.0° C. for 20 sec, 72.0° C. for 45 sec, and a final extension of 72.0° C. for 3 min. PCR products were visualized on a 1.5% agarose gel.

EXAMPLE 9
Detection of Expressed Reactive Oxygen Species

Fresh mouse colons were frozen in Tissue-Tek® O.C.T. (Optimal Cutting Temperature) Compound from Fisher Scientific International, Inc. and sectioned in a cryostat at a thickness of 6–10 μm. Sections were kept at −80° C. until use. The sections were then brought to room temperature, and in the dark were covered with 200–1000 μL of 10 μM dihydroethidium (DHE) in HANKS buffer. Following a 15–30 min incubation at 37° C. at 5% $CO_2$, the slices were washed twice in HANKS buffer then mounted in Fluoromount G. DHE staining was immediately visualized using a fluorescence/confocal microscope. The Kolmogorov-Smirnov test was used to determine the significance of differences between data sets.

EXAMPLE 10

Challenge of Mice with Bacterial Strain

Bacteria (*Citrobacter rodentium*; Genomospecies 9, Schaver, DB J. Clin. Microbiol. 33:2064–2068 1995) were grown overnight in five 5 ml cultures. The *C. rodentium* was then pelleted from the five pooled overnight cultures and 100 ml of 20% sucrose was added to the pellet. On the morning of day 1, chow was removed and the water was replaced with the 100 ml *C. rodentium* 20% sucrose solution. Groups of five mice of two different genotypes, the Cre/NOX1/Min crosses and a control group, were allowed to drink for 24 hrs. On day 2 the amount of bacteria/sucrose solution was measured and the amount consumed by each mouse calculated. Dilutions of the bacteria/sucrose solution were plated out on agar and incubated overnight and counted to determine colony-forming units/mouse. A daily record of each mouse's weight was recorded. All mice were sacrificed on day 10 by $CO_2$. Four cm of the colon, measured from the rectum, was cleaned with 1×PBS, allowed to drain, weighed, frozen in O.C.T., and stored at −80° C. until use.

EXAMPLE 11

Measurement of Colon Crypt Depth

Colon crypt depth was measured from pit to tip (See FIG. 4) In the figure, each point represents a separate measurement, on 5 animals in each group. The four groups of mice were wild type, mice with the transgene for NOX1, as controls and mice with and without NOX1 exposed to *Citrobacter*. This depth is a measure of hyperplasia (or overgrowth of the colonic epithelial cells). Hyperplasia is a response that happens normally upon exposure of mice to pathogenic bacteria, in this case *Citrobacter* in the drinking water (compare first set of points to third). This demonstrates that over-expression of NOX1 in colonic epithelium alone does not have much effect on hyperplasia (first 2 groups). However, upon exposure to pathogenic bacteria, there is a marked increase in the hyperplastic response (last 2 groups). Therefore, reactive oxygen by itself is not sufficient for growth. However, in combination with another stimulus, such as *Citrobacter*, it has an amplifying effect, resulting in marked growth.

All patents, publications and abstracts cited above are incorporated herein by reference in their entirety. It should be understood that the foregoing relates only to preferred embodiments of the present invention and that numerous modifications or alterations may be made therein without departing from the spirit and the scope of the present invention as defined in the following claims.

We claim:

1. A transgenic mouse, whose genome comprises a transgene encoding NOX1, wherein the transgene comprises a nucleic acid encoding SEQ ID NO: 2 operatively linked to a CX1 promoter, and wherein the mouse exhibits an increased overgrowth of colonic epithelial cells upon exposure to pathogenic bacteria.

2. The transgenic mouse of claim 1, wherein the mouse is heterozygous for the transgene.

3. The transgenic mouse of claim 1, wherein the mouse is homozygous for the transgene.

4. The mouse of claim 1, wherein the transgene comprises SEQ ID NO: 1.

5. The transgenic mouse of claim 1, wherein the transgene comprises a LoxP flox stop cassette.

6. The transgenic mouse of claim 5, wherein the LoxP flox stop cassette encodes a marker protein.

7. The transgenic mouse of claim 6, wherein the marker protein is green enhanced fluorescent protein.

8. A method for identifying a therapeutic agent for use in treating hyperplasia of colonic epithelial cells, comprising administering a test compound to the transgenic mouse of claim 1;

exposing the transgenic mouse to a pathogenic bacteria; and assessing the amount of hyperplasia of colonic epithelial cells of the transgenic mouse;

wherein a decrease in the amount of hyperplasia of colonic epithelial cells in the transgenic mouse as compared to a control mouse identifies the agent as being of use in treating hyperplasia of colonic epithelial cells.

9. The method of claim 8, wherein the transgenic mouse is heterozygous for the transgene.

10. The method claim 8, wherein the transgenic mouse is homozygous for the transgene.

11. A cell or cell line isolated from the transgenic mouse of claim 1.

* * * * *